United States Patent
Lengyel et al.

(10) Patent No.: US 8,748,470 B2
(45) Date of Patent: Jun. 10, 2014

(54) METHODS FOR TREATING OVARIAN CANCER BY INHIBITING FATTY ACID BINDING PROTEINS

(75) Inventors: Ernst Lengyel, Chicago, IL (US); Kristin Nieman, Westchester, IL (US); Hilary Kenny, Chicago, IL (US)

(73) Assignee: The University of Chicago, Chicago, IL (US)

( * ) Notice: Subject to any disclaimer, the term of this patent is extended or adjusted under 35 U.S.C. 154(b) by 0 days.

(21) Appl. No.: 13/422,712

(22) Filed: Mar. 16, 2012

(65) Prior Publication Data

US 2012/0289570 A1    Nov. 15, 2012

Related U.S. Application Data

(60) Provisional application No. 61/453,685, filed on Mar. 17, 2011.

(51) Int. Cl.
| | |
|---|---|
| A61K 31/415 | (2006.01) |
| A61P 35/00 | (2006.01) |
| A61K 31/381 | (2006.01) |
| A61P 35/04 | (2006.01) |

(52) U.S. Cl.
USPC ......... 514/406; 514/444; 514/19.3; 514/19.2; 514/340; 514/422

(58) Field of Classification Search
CPC . A61K 2121/00; A61K 31/35; A61K 31/353; A61K 31/415; A61K 31/428; A61K 31/635; A61K 31/7105; C07D 209/86; C07D 233/64; C07D 233/70; C07D 261/08; C07D 263/32; C07D 277/24; C07D 473/00
USPC ................ 514/406, 444, 49.3, 19.2, 340, 422
See application file for complete search history.

(56) References Cited

U.S. PATENT DOCUMENTS

| | | | |
|---|---|---|---|
| 6,670,380 B2 | 12/2003 | Sulsky et al. | 514/345 |
| 7,390,824 B1 | 6/2008 | Robl et al. | 514/374 |
| 2009/0170783 A1* | 7/2009 | Schuster et al. | 514/18 |

FOREIGN PATENT DOCUMENTS

| | | |
|---|---|---|
| WO | WO 01/54694 | 8/2001 |
| WO | WO 03/006023 | 1/2003 |
| WO | WO 03/043624 | 5/2003 |
| WO | WO 2004/063156 | 7/2004 |
| WO | WO 2010/056630 | 5/2010 |

OTHER PUBLICATIONS

Ayers et al., "Continuous nucleocytoplasmic shuttling underlies transcriptional activation of PPARgamma by FABP4," *Biochemistry*, 46:6744-6752, 2007.

Balendiran et al., "Crystal structure and thermodynamic analysis of human brain fatty acid-binding protein," *J. Biol. Chem.*, 275:27045-27054, 2000.

Barf et al., "N-Benzyl-indolo carboxylic acids: Design and synthesis of potent and selective adipocyte fatty-acid binding protein (A-FABP) inhibitors," *Bioorg. Med. Chem. Lett.*, 19(6):1745-1748, 2009.

(Continued)

*Primary Examiner* — Savitha Rao
(74) *Attorney, Agent, or Firm* — Fulbright & Jaworski LLP

(57) ABSTRACT

The present invention concerns methods and compositions for the inhibition or reduction of the primary tumor and metastasis by inhibition of fatty acid binding proteins.

13 Claims, 35 Drawing Sheets a b

(56) References Cited

OTHER PUBLICATIONS

Brasamele et al., "Perilipin A and the control of triacylglycerol metabolism," *Mol. Cell. Biochem.*, 326:15-21, 2009.
Carey et al., "Functional proteomic analysis of advanced serous ovarian cancer using reverse phase protein array: TGF-b pathway signaling indicates reponse to primary chemotherapy," *Clin. Cancer Res.*, 16(10):2852-2860, 2010.
Cataltepe et al., "Fatty acid binding protein 4 is expressed in distinct endothelial and non-endothelial cell populations in glioblastoma," *Neuropathol Appl Neurobiol.*, Nov. 17, 2011. Accepted Article. Doi: 10.1111/j.1365-2990.2011.01237.x. [Epub ahead of print].
Chmurzynska, "The multigene family of fatty acid-binding proteins (FABPs): function, structure and polymorphism," *J. Appl. Genet.*, 47(1):39-48, 2006.
Cho and Shih, "Ovarian cancer," *Annu. Rev. Pathol.*, 4:287-313, 2009.
Coe and Bernlohr, "Physiological properties and functions of intracellular fatty acid-binding proteins," *Biochim. Biophys. Acta*, 1391:287-306, 1998.
DeBernardis, "The biology of cancer: Metaoblic programming fuels cell growth and proliferation," *Cell Metabolism*, 7(1):11-20, 2008.
Dirat et al., "Cancer-associated adipocytes exhibit an activated phenotype and contribute to breast cancer invasion," *Cancer Res.*, 71(7):2455-2465, 2011.
Drew et al., "Correlation of tumor- and stromal-derived MTI-MMP expression with progression of human ovarian tumors in SCID mice," *Gynecologic Oncology*, 95:437-448, 2004.
Elliott et al., "Capacity of adipose tissue to promote growth and metastasis of a murine mammary carcinoma: Effect of estrogen and progesterone," *Int. J. Cancer*, 519(3):416-424, 1992.
Flower et al., "Structure and sequence relationships in the lipocalins and related proteins," *Protein Sci.*, 2(5):753-761, 1993.
Folkins et al., "Precursor to pelvic serous carcinoma and their clinical implications," *Gynecol. Oncol.*, 113(3):391-396, 2009.
Furuhashi and Hotamisligil, "Fatty acid binding proteins: Role in metabolic diseases and potential as drug targets," *Nature Reviews Drug Discovery*, 79(6):489-503, 2008.
Furuhashi et al., "Treatment of diabetes and atherosclerosis by inhibiting fatty-acid-binding protein aP2," *Nature*, 447(7147):959-965, 2007.
Gagnon et al., "Thyroid-stimulating hormose stimulates lipolysis in adipocytes in culture and raises serum free fatty acid levels in vivo," *Metabolism Clinical and Experimental*, 59(4):547-553, 2010.
Gazi et al., "Direct evidence of lipid translocation between adipocytes and prostate cancer cells with imaging FTIR microspectroscopy," *Journal of Lipid Research*, 48(8):1846-56, 2007.
Gillian et al., "Structural basis for activation of fatty acid-binding protein 4," *J. Mol. Biol.*, 372(5):1246-1260, 2007.
Gonzalez-Yanes et al., "Signalling mechanisms regulating lipolysis," *Cellular Signaling*, 18(4):401-408, 2006.
Greenaway et al., "Epithelial-stromal interaction increases cell proliferation, survival and tumorigenicity in a mouse model of human epithelial ovarian cancer," *Gynecologic Oncology*, 108:385-394, 2008.
Hardy et al., "Oleate promotes the proliferation of breast cancer cells via the G protein-coupled receptor GPR40," *J. Biol. Chem.*, 280:13285-13291, 2005.
Haunderland and Spencer, "Fatty acid-binding proteins—insights from genetic manipulations," Prog. Lipid Res., 43(4):328-349, 2004.
Hernlund et al., "Potentiation of chemotherapeutic drugs by energy metabolism inhibitors 2-deoxyglucose and etomoxir," *Int. J. Cancer*, 123(2):476-483, 2008.
Hertzel et al., "Identification and characterization of a small molecule inhibitor of fatty acid binding proteins," *J. Med. Chem.*, 52(19):6024-6031, 2009.
Hotamisiligil et al., "Uncoupling of obesity from insulin resistance through a targeted mutation in aP2, the adipocyte fatty acid binding protein," *Science*, 274(5291):1377-1379, 1996.
Hunt et al., "Adipocyte P2 gene: developmental expression and homology of 5'-flanking sequences among fat cell-specific genes," *Proc. Natl. Acad. Sci.*, 83(11):3786-3790, 1986.
Kaur et al., "b3-integrin expression on tumor cells inhibits tumor progression, reduces metastasis, and is associated with a favorable prognosis in patients with ovarian cancer," *Am. J. Pathol.*, 175(5):2184-2196, 2009.
Kenney et al., "Use of a novel 3D culture model to elucidate the role of mesothelial cells, fibroblasts and extra-cellular matrices on adhesion and invasion of ovarian cancer cells," *Int. J. Cancer*, 121:1463-1472, 2007.
Landen et al., "Early events in the pathogensis of epithelial ovarian cancer," *J. Clin. Oncol.*, 26:995-1005, 2008.
Lehmann et al., "Discovery of inhibitors of human adipocyte fatty acid-binding protein, a potential type 2 diabetes target," *Bioorg. Med. Chem. Lett.*, 14:4445-4448, 2004.
Lengyel, "Ovarian cancer development and metastasis," *Am. J. Pathol.*, 177(3):1053-64, 2010.
Levine and Puzio-Kuter, "The control of the metabolic switch in cancers by oncogenes and tumor suppressor genes," *Science*, 330(6009):1340-1344, 2010.
Liu et al., "Fatty acid oxidation is a dominant bioenergetic pathway in prostate cancer," *Prostate Cancer Prostatic Dis.*, 9(3):230-234, 2006.
Makowski and Hotamisligil, "The role of fatty acid binding proteins in metabolic syndrome and atherosclerosis," *Curr. Opin. Lipidol.*, 16(5):543-548, 2005.
Manabe et al., "Mature adipocytes, but not preadipocytes, promote the growth of breast carcinoma cells in collagen gel matrix culture through cancer-stromal cell interactions," *J. Pathology*, 201(2):221-228, 2003.
Martinez-Outschoorn et al., "The autophagic tumor stroma model of cancer or "battery-operated tumor growth" a simple solution to the autophagy paradox," *Cell Cycle*, 9(21):4297-4306, 2010.
Merritt et al., "Effect of interleukin-8 gene silencing with liposome-encapsulated small interfering RNA on ovarian cancer cell growth," *J. Natl. Cancer Inst.*, 100(5):359-372, 2008.
Moon and Rhead, "Complementation analysis of fatty acid oxidation disorders," *J. Clin. Invest.*, 79(1):59-64, 1987.
Munday et al., "Identification by amino acid sequencing of three major phosphorylation sites on rat acetyl-CoA carboxylase," *Eur. J. Biochem.*, 175(2):331-338, 1998.
Nieman et al., "Adipocytes promote ovarian cancer metastasis and provide energy for rapid tumor growth," *Nat. Med.*, 17(11):1498-1503, 2011.
Nilsson et al., "Interleukin-6 secreted by human ovarian carcinoma cells is a potent proangiogenic cytokine," *Cancer Res.*, 65(23):10794-10800, 2005.
Okada et al., "Synthesis of BMS-309403-related compounds, including [$^{14}$C]BMS-309403, a radioligand for adipocyte fatty acid binding protein," *Chem. Pharm. Bull.*, 60(1):164-168, 2012.
Pavlides et al., "The reverse Warburg effect: aerobic glycolysis in cancer associated fibroblasts and the tumor stroma," *Cell Cycle*, 8:3984-4001, 2009.
Pike et al., "Inhibition of fatty acid oxidation by etomoxir impairs NADPH production and increases reactive oxygen species resulting in ATP depletion and cell death in human glioblastoma cells," *Biochim. Biophys. Acta*, 1807:726-734, 2011.
Ringom et al., "Substituted benzylamino-6-(trifluoromethyl)pyrimidin-4(1H)-ones: a novel class of selective human A-FABP inhibitors," *Bioorg. Med. Chem. Lett.*, 14(17):4449-4452, 2004.
Robinson-Smith et al., "Macrophages mediate inflammation-enhanced metastasis of ovarian tumors in mice," *Cancer Research*, 37(12):5708-16, 2007. (p. 51—ID8 mouse OvCa cells).
Roby et al., "Development of syngeneric mouse model for events related to ovarian cancer," *Carcinogenesis*, 21(4):585-591, 2000.
Scheja et al., "Altered insulin secretion associated with reduced lipolytic efficiency in a P2-/-mice," *Diabetes*, 48(10):1987-1994, 1999.

(56) References Cited

OTHER PUBLICATIONS

Sengenès et al., "Involvement of a cGMP pathway in a natriuretic peptide-mediated hormone sensitive lipase phosphorylation in human adipocytes," *J. Biol. Chem.*, 278(49):48617-18626, 2003.

Smith et al., "Interaction of the adipocyte fatty acid-binding protein with the hormone-sensitive lipase: regulation by fatty acids and phophorylation," *J. Biol. Chem.*, 282:32424-23432, 2007.

Spiegelman et al., "Molecular cloning of mRNA from 3T3 adipocytes. Regulation of mRNA content for glycerophosphate dehydrogenase and other differentiation-dependent proteins during adipocyte development," *J. Biol. Chem.*, 258(16):10083-10089, 1983.

Suhre et al., "Identification of a potential biomarker for FABP4 inhibition: The power of lipidomics in preclinical drug testing," *Journal of Biomolecular Screening*, 16(5):467-75, 2011. Epub. May 4, 2011.

Sultsky et al., "Potent and selective biphenyl azole inhibitors of adipocyte fatty acid binding protein (aFABP)," *Bioorg. Med. Chem. Lett.*, 17:3511-3515, 2007.

Tokuda et al., "Prostate cancer cell growth is modulated by adipocyte-cancer cell interaction," *BJU Internatnional*, 91(7):716-720, 2003.

Uysal et al., "Improved glucose and lipid metabolism in generically obese mice lacking aP2," *Endocrinology*, 141(9):3388-3396, 2000.

Wakil and Abu-Elheiga, "Fatty acid metabolism: Target for metabolic syndrome," *Journal of Lipid Research*, 50:S138-S143, 2009.

Wang and Gaum, "AMP-activated protein kinase and cancer," *Acta Physiol.*, 196(1):55-63, 2009.

Zaugg et al., "Carnitine palmitoyltransferase IC promotes cell survival and tumor growth under conditions of metabolic stress," *Genes Dev.*, 25(10):1041-1051, 2011.

Zhou et al., "An orally available small-molecule inhibitor of c-Met PF-2341066, exhibits cytoreductive antitumor efficacy through antiporliferative and antiangiogenic mechanisms," *Cancer Res.*, 67(9): 4408-4417, 2007.

Zillhardt et al., "An orally available small molecule inhibitor of c-Met PF-2341066, reduces tumor burden in a pre-clinical model of ovarian cancer metastasis," *Neoplasia*, 12(1);1-10, 2010.

* cited by examiner

FAPB4 deficiency prevents lipid accumulation in mouse ovarian cancer cells

ID8 + FABP4⁻/⁻ adipocytes    ID8 + WT adipocytes

*In vitro*

ID8 tumor in FABP4⁻/⁻ mice    ID8 tumor in WT mice

*In vivo*

METHODS FOR TREATING OVARIAN CANCER BY INHIBITING FATTY ACID BINDING PROTEINS

This application claims priority to U.S. Provisional Patent Application 61/453,685 filed on Mar. 17, 2011, which is hereby incorporated by reference in its entirety.

This invention was made with government support under RO1CA111882 awarded by the National Cancer Institute. The government has certain rights in the invention.

FIELD OF THE INVENTION

The present invention relates generally to the fields of medicine, oncology, and biology. More particularly, it concerns methods and compositions related to inhibition of metastasis by inhibiting fatty acid binding proteins.

BACKGROUND

Metastasis is the primary cause of cancer mortality and is a complex process with multiple steps that include tumor cell invasion, intravasation, extravasation, and establishment of secondary tumors in distant organs. Clinical observations indicate the most common site of ovarian cancer (OvCa) metastasis is the omentum. The omentum, primarily composed of adipocytes, provides energy storage and functions as an endocrine organ secreting adipokines and participating in lipid metabolism. A growing body of evidence supports dysregulation of metabolism, including lipid metabolism, as a hallmark of cancer. In addition, cancer cell malignancy is highly dependent on the surrounding environment. In breast tumor cells, adipocytes constitute one of the most prominent cell types and have been indicated in disease progression. Adipocyte fatty acid binding protein 4 (FABP4), functions in transport, uptake, and metabolism of fatty acids. FABP4 plays a role in the integration of metabolic and inflammatory signaling and has been indicated in many aspects of metabolic syndrome.

There is a need for additional methods and compositions for treating metastatic disease. Accordingly, methods and compositions for preventing and treating cancer, including suppressing or inhibiting metastasis, are provided by inhibition of a FABP protein.

SUMMARY OF THE INVENTION

Embodiments include methods and compositions for reducing or inhibiting cancer, including suppressing or inhibiting the primary tumor and metastasis. In certain aspects the interaction between adipocytes and cancer cells is interrupted, thus reducing or inhibiting the establishment of metastasis in or around a tissue or organ having adipocytes. In certain aspects the methods and compositions inhibit or reduce metastasis to the omentum, kidney, liver, gastrointestinal tract, peritoneum, bladder, uterus, ovary, fallopium tube, skin, lung, lymph nodes, brain, bone or breast. In certain aspects the cancer is inhibited by reducing the growth of the cancer cell, increasing death of the cancer cell or reducing the invasion or extravasation of the cancer cell.

Embodiments include methods of inhibiting a primary tumor or cancer cell metastasis comprising administering to a subject having or suspected of having cancer an effective amount of a fatty acid binding protein (FABP) inhibitor. In certain embodiments the subject has been determined to have cancer. In additional embodiments, the patient has had a biopsy that indicates the patient has cancer. In a further aspect the FABP inhibitor is administered to a cancer patient for the treatment of cancer. It is contemplated that other conditions and diseases such as diabetes can be specifically excluded from the scope of the methods described herein. A subject may also be identified as having a particular grade of cancer or condition (e.g., poor prognosis or good prognosis) that is at a higher probability for metastasis or more predicted to have a more favorable outcome for certain treatments. In certain aspects the method of inhibiting cancer cell metastasis includes administering to a cancer patient or a subject suspected of having cancer or a subject determined to be at risk of developing cancer an effective amount of a fatty acid binding protein (FABP) inhibitor. The FABP inhibitor can be a FABP4 and/or a FABP5 inhibitor. The FABP4 inhibitor can be a carbazole butanoic acid, aryl sulfonamide, sulfonylthiophene derivative, 4-hydroxypyrimidine, tetrahydrocarbazole derivative, 2,3-dimethylindole derivative, benzoylbenzene, biphenyl-alkanoic acid derivative, 2-oxazole-alkanoic acid derivative, tetrahydropyrimidone, pyridone, pyrazinone, aryl carboxylic acid, tetrazole, triazolopyrimidinone, and indole derivative. In certain aspects the FABP4 inhibitor is BMS309403; pyrazole, 4-{[2-(methoxycarbonyl)-5-(2-thienyl)-3-thienyl]amino}-4-oxo-2-butenoic acid or ((2'-(5-ethyl-3,4-diphenyl-1H-pyrazol-1-yl)(1,1'-biphenyl)-3-yl) oxy)-acetic acid. In certain embodiments, the FABP4 inhibitor can be a small interference RNA (siRNA), in particular, a small hairpin RNA (shRNA). In certain aspects, the shRNA against FABP4 comprises a nucleic acid sequence of SEQ ID NO: 1. In certain embodiments the FABP inhibitor is a FABP5 inhibitor. The FABP5 inhibitor can be an indole derivatives (Lehmann et al 2004), triazolopyrimidinone derivative (Schering Corporation, PCT/US2009/063787), Pyrazole (BMS309403, Bristol Myers Squibb, described in Sulsky et al 2007), or BMS480404 (Bristol Myers Squibb, described in McDonnell et al 2006). In certain aspects the FABP inhibitor inhibits the activity of more than one FABP. In certain aspects the FABP inhibitor is administered intravascularly, intraperitoneally, or orally. The FABP inhibitor can be administered in a dose of 5, 10, 20, 30, 40, 50, 60 mg/kg/day to 20, 30, 40, 50, 60, 70, 80, 90, 100 mg/kg/day, including all values and ranges there between. The FABP inhibitor can be administered 1, 2, 3, 4, 5, 6, 7, 8, 9, or 10 times a day, a week, or a month. The FABP inhibitor can be administered every 1, 12, 24, 48, 72, 96, or 120 hours (including all values and ranges there between); or every day; every other day, every third day, every fourth day, every fifth day, once a week, bi-weekly, by intravenous drip, by perfusion, or by infusion. In certain embodiments, an FABP inhibitor is in a pharmaceutical composition.

Certain embodiments include methods that further comprise administering a second anti-cancer therapy. The second anti-cancer therapy can be chemotherapy, radiotherapy, surgery, cryotherapy, hormonal therapy, or immunotherapy. In certain aspects the chemotherapy is paclitaxel, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, paclitaxel, taxotere, gemcitabine, navelbine, a farnesyl-protein transferase inhibitor, a PARP inhibitor, a c-Met inhibitor, an anti-angiogenic, transplatinum, 5-fluorouracil, vincristin, vinblastin, topotecan or methotrexate.

In certain aspects the cancer patient has or is suspected of having cancer. In certain embodiments the cancer is ovarian, breast, gastric, colon, or prostate cancer. In a further aspect the patient has or is suspected of having ovarian cancer. In other aspects the subject is determined to have a genetic predisposition for or is determined to be at increased risk of developing cancer. In certain embodiments the subject is at increased risk of developing ovarian, breast, gastric, colon, or prostate cancer. In a further aspect the patient is at increased risk of developing ovarian cancer. In a further aspect of the invention, the subject suspected of having cancer or determined to have a genetic disposition to cancer has a mutation in the BRCA (Breast Cancer Gene) 1, BRCA2 or HNPCC (Hereditary Non-Polyposis Colon Cancer) associated genes. In certain aspects a subject has or is suspected of having ovarian, breast, gastric, colon, pancreatic, gastrointestinal tract, or prostate cancer. In a further aspect the subject has or is suspected of having peritoneal, fallopian, or ovarian carcinoma (muellerian tumors).

Embodiments include methods for inhibiting ovarian cancer metastasis to the omentum comprising administering to a patient having or at risk of developing ovarian cancer an effective amount of a fatty acid binding protein 4 (FABP4) inhibitor. Other embodiments include methods for inhibiting ovarian cancer metastasis to other fat containing areas, including the mesentery of the bowel, the appendices of the large bowel, the remnants of the omentum after surgery and the peritoneum, comprising administering an effective amount of a FABP4 inhibitor. In a further aspect the metastasis is a metastasis to the omentum, kidney, liver, breast, peritoneum, bladder, uterus, ovary, fallopium tube, skin, lung, lymph nodes, brain, and/or bone Embodiments include methods of inhibiting ovarian cancer metastasis to fat containing tissue within the abdominal cavity comprising administering to a patient having or at risk of developing ovarian cancer an effective amount of a fatty acid binding protein 4 (FABP4) inhibitor. In certain aspects the fat containing tissue is the mesentery of the bowel, the appendices of the large bowel, the remnants of the omentum after surgery and the peritoneum.

Further embodiments include methods for inhibiting the growth or spread of a metastatic cancer in a subject comprising administering to a subject having or determined to have cancer or a potentially metastatic cancer an effective amount of a fatty acid binding protein 4 (FABP4) inhibitor.

Certain embodiments include methods of inhibiting cancer cell growth comprising administering to a cancer patient an effective amount of a fatty acid binding protein (FABP) inhibitor.

It is contemplated that any embodiment of a method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

The use of the term "or" in the claims is used to mean "and/or" unless explicitly indicated to refer to alternatives only or the alternative are mutually exclusive, although the disclosure supports a definition that refers to only alternatives and "and/or."

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
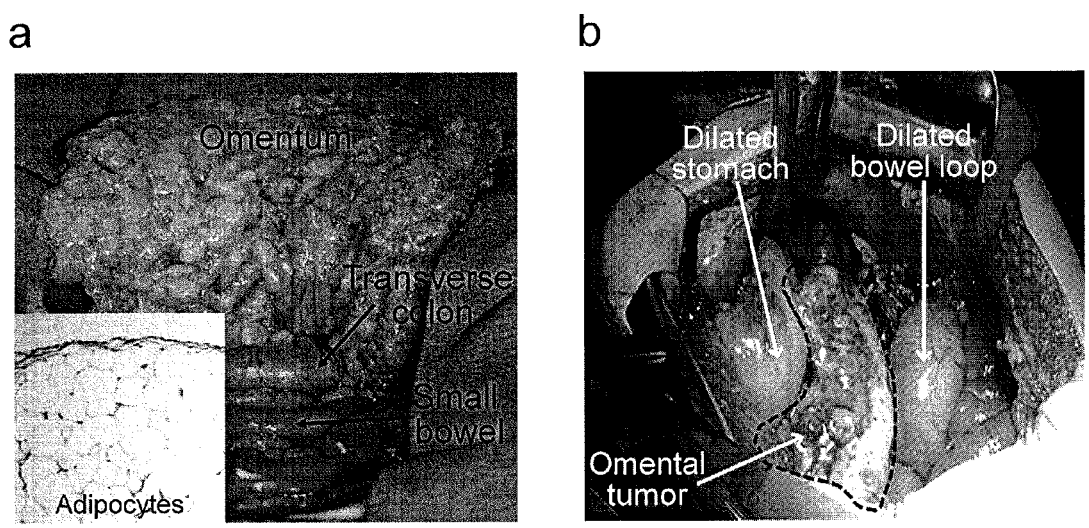
FIGS. 1a-1b Human omental transformation by ovarian cancer. (a) Normal human omentum (extended upward) and hematoxylin and eosin staining (H&E staining) of a section of normal human omentum (inset), showing the omentum consists mostly of adipocytes covered by a layer of mesothelial cells. (b) Tumor transformed omentum. Ovarian cancer patient undergoing tumor debulking from a midline incision. The patient's head is at the top. The omental tumor is causing a bowel obstruction.

Intraabdominal tumors such as ovarian cancer (OvCa) have a clear predilection for metastasis to the omentum, an organ positioned in front of the bowel and primarily composed of adipocytes (Landen et al., 2008; Cho and Shih, 2009). Currently, it is unclear why tumor cells preferentially home to and proliferate in the omentum, yet omental metastases typically represent the largest tumor in the patient's abdominal cavity. The inventors show that primary human omental adipocytes promote the homing, migration, and invasion of OvCa cells to the omentum; activities mediated by several adipokines, including interleukin (IL)-8. The interaction of tumor cells and adipocytes induces lipolysis in the adipocytes and β-oxidation in the cancer cells. Coculture leads to the direct transfer of lipids from adipocytes to the tumor cells and promotes in vitro and in vivo tumor growth suggesting that adipocytes act as an energy source for the cancer cells. A protein array comparing primary ovarian tumors with their corresponding metastases identified upregulation of fatty acid binding protein 4 (FABP4, also known as aP2) in omental metastases, and staining for FABP4 showed tumor cell expression at the adipocyte/tumor cell interface. FABP4 deficiency substantially impaired metastatic tumor growth in mice, indicating FABP4's key role in ovarian cancer metastasis. Injection of mouse OvCa cells into FABP4 knockout mice indicated FABP4 expression in adipocytes was involved in tumor growth and metastasis. These data indicate that adipocytes promote homing of tumor cells to the omentum and provide fatty acids for rapid tumor growth, identifying lipid metabolism and transport as novel targets for the treatment of intraabdominally metastasizing tumors.

Fatty Acid Binding Protein (FABP)

The fatty-acid-binding proteins (FABPs) are a family of carrier proteins for fatty acids and other lipophilic substances such as eicosanoids and retinoids. These proteins are thought to facilitate the transfer of fatty acids between extra- and intracellular membranes. Some family members are also believed to transport lipophilic molecules from outer cell membrane to certain intracellular receptors such as PPAR. The family includes FABP 1, FABP 2, FABP 3, FABP 4, FABP 5, FABP 6, FABP 7, FABP 8, FABP 9, FABP 11, FABP 5-like 1, FABP 5-like 2, FABP 5-like 3, FABP 5-like 4, FABP 5-like 5, FABP 5-like 6, and FABP 5-like 7. Different members of the FABP family exhibit unique patterns of tissue expression and are expressed most abundantly in tissues involved in active lipid metabolism.

All FABPs bind long-chain fatty acids with differences in ligand selectivity, binding affinity and binding mechanism (Chmurzynska, A. J. Appl. Genet. 47, 39-48 (2006)) as a result of small structural differences between isoforms. In general, the more hydrophobic the ligand the tighter the binding affinity—with the exception of unsaturated fatty acids. It is also possible that the needs of target cells determine the affinity and even selectivity of the major isoform present at different sites. For example, brain FABP is highly selective for very long-chain fatty acids such as docosahexaenoic acid (Balendiran et al. J. Biol. Chem. 275, 27045-27054 (2000)). On the other hand, liver FABP exhibits binding capacity for a broad range of ligands from lysophospholipids to heme (Coe and Bernlohr, Biochim. Biophys. Acta 1391, 287-306 (1998)).

There is a conserved fingerprint for all fatty acid-binding proteins (FABPs) (PRINTS pattern FATTYACIDBP; PR00178), which is derived from three motifs. Motif 1 includes the G-x-W triplet, which forms part of the first β-strand (βA) and corresponds to a similar motif in the sequence of lipocalins, in which it has the same conformation and location within the protein fold (Flower et al., Protein Sci. 2, 753-761, 1993) (see PROSITE pattern FABP; PS00214). Motif 2 spans the C terminus of strand 4 (βD) and includes strand 5 (βE). Motif 3 encodes strands 9 (βI) and 10 (βJ). In adipocyte FABP (FABP4), potential functional domains include a nuclear localization signal (NLS) and its regulation site, nuclear export signal (NES) and a hormone-sensitive lipase (HSL) binding site (Ayers et al., Biochemistry 46, 6744-6752, 2007; Gillian et al., J. Mol. Biol. 372, 1246-1260, 2007; Smith et al., J. Biol. Chem. 282, 32424-32432, 2007).

Numerous functions have been proposed for FABPs. As lipid chaperones, FABPs may actively facilitate the transport of lipids to specific compartments in the cell, such as to the lipid droplet for storage; to the endoplasmic reticulum for signalling, trafficking and membrane synthesis; to the mitochondria or peroxisome for oxidation; to cytosolic or other enzymes to regulate their activity; to the nucleus for lipid-mediated transcriptional regulation; or even outside the cell to signal in an autocrine or paracrine manner. The proper engagement of targets in a spatially controlled manner requires the action of lipid chaperones (See Furuhashi and Hotasmisligil, 2008 for review).

FABP4 (GenBank accession CAG33184 (GI: 48145923)), also known as adipocyte FABP, was first detected in mature adipocytes and adipose tissue (Spiegelman et al., J. Biol. Chem. 258, 10083-10089, 1983; Hunt et al., Proc. Natl. Acad. Sci. USA 83, 3786-3790, 1986). This protein has also been termed adipocyte P2 (aP2) because of its high sequence similarity (67%) to peripheral myelin protein 2 (M-FABP/FABP8) (Hunt et al., Proc. Natl. Acad. Sci. USA 83, 3786-3790, 1986). Expression of FABP4 is highly regulated during differentiation of adipocytes, and its mRNA is transcriptionally controlled by fatty acids, PPAR-γ agonists and insulin (Haunerland and Spener, Prog. Lipid Res. 43, 328-349, 2004; Makowski and Hotamisligil, Curr. Opin. Lipidol. 16, 543-548, 2005). It is known that blocking this protein either through genetic engineering or drugs has the possibility of treating heart disease, diabetes, asthma, obesity, and fatty liver disease.

FABP Inhibitors

Recently, a series of FABP inhibitors have been identified (See for example Furuhashi and Hotamisligil, 2008). These include carbazole-based and indole-based inhibitors (Lehmann et al., Bioorg. Med. Chem. Lett. 14, 4445-4448, 2004); benzylamino-6-(trifluoromethyl)pyrimidin-4(1H) inhibitors (Ringom et al., Bioorg. Med. Chem. Lett. 14, 4449-4452, 2004); and a biphenyl azole inhibitor (BMS309403) (Sulsky et al., Bioorg. Med. Chem. Lett. 17, 3511-3515, 2007). In a fluorescent 1-anilinonaphthalene-8-sulphonic acid binding displacement assay, BMS309403 had $K_i$ values <2 nM for FABP4 compared with 250 nM for H-FABP and 350 nM for E-FABP. By contrast, the endogenous fatty acids, palmitic acid and oleic acid, had FABP4 $K_i$ values of 336 nM and 185 nM, respectively. BMS309403 seems to have greater potency compared with the other reported potential inhibitors, which have IC50 values >0.5 μM.

FABP4 inhibitors include carbazole butanoic acid (Lehmann et al., 2004, which is incorporated herein by reference in its entirety), aryl sulfonamides (Lehmann et al. 2004, which is incorporated herein by reference in its entirety), sulfonylthiophene derivatives (Lehmann et al. 2004, which is incorporated herein by reference in its entirety), 4-hydroxypyrimidines and analogs (Ringom et al., 2004, which is incorporated herein by reference in its entirety), BMS309403 (Pyrazole, Bristol Myers Squibb, described in Sulsky et al 2007, which is incorporated herein by reference in its entirety), HTS01037 4-{[2-(methoxycarbonyl)-5-(2-thienyl)-3-thienyl]amino}-4-oxo-2-butenoic acid (Hertzel et al 2009, which is incorporated herein by reference in its entirety), tetrahydrocarbazole derivatives (Barf et al 2009, which is incorporated herein by reference in its entirety), 2,3-dimethylindole derivatives (Barf et al 2009, which is incorporated herein by reference in its entirety), benzoylbenzenes (Bristol Myers Squibb, described in U.S. Pat. No. 7,390,824, which is incorporated herein by reference in its entirety), biphenyl- and 2-oxazole-alkanoic acid derivatives (Bristol Myers Squibb, described in U.S. Pat. No. 7,390,824, which is incorporated herein by reference in its entirety), tetrahydropyrimidones (Bristol Myers Squibb, described in PCT/US01/02350, which is incorporated herein by reference in its entirety), pyridones (Bristol Myers Squibb, described in U.S. Pat. No. 6,670,380, which is incorporated herein by reference in its entirety), pyrazinones (Bristol Myers Squibb, described in PCT/US02/22186, which is incorporated herein by reference in its entirety), aryl carboxylic acids (Bristol Myers Squibb, described in PCT/US02/36580, which is incorporated herein by reference in its entirety), tetrazoles (Bristol Myers Squibb, described in PCT/US02/36580, which is incorporated herein by reference in its entirety), triazolopyrimidinones (Schering Corporation, described in PCT/US2009/063786, which is incorporated herein by reference in its entirety), and indole derivatives (Bristol Myers Squibb, described in PCT/SE2004/000005, which is incorporated herein by reference in its entirety).

In certain aspects the FABP4 inhibitors is 5,6,7,8,9,10-hexahydrocyclohepta[b]indole-4-carboxylic acid; methyl 5,6,7,8,9,10-hexahydrocyclohepta[b]indole-4-carboxylate; methyl 9-benzyl-2,3,4,9-tetrahydro-1H-carbazole-8-carboxylate; 9-benzyl-2,3,4,9-tetrahydro-1H-carbazole-8-carboxylic acid; methyl 9-(4-bromobenzyl)-2,3,4,9-tetrahydro-1H-carbazole-8-carboxylate; 9-(4-bromobenzyl)-2,3,4,9-tetrahydro-1H-carbazole-8-carboxylic acid; methyl 9-(4-methylbenzyl)-2,3,4,9-tetrahydro-1H-carbazole-8-carboxylate; 9-(4-methylbenzyl)-2,3,4,9-tetrahydro-1H-carbazole-8-carboxylic acid; methyl 9-(4-cyanobenzyl)-2,3,4,9-tetrahydro-1H-carbazole-8-carboxylate; 9-[4-(aminocarbonyl)benzyl]-2,3,4,9-tetrahydro-1H-carbazole-8-carboxylic acid; methyl 9-(3-methoxybenzyl)-2,3,4,9-tetrahydro-1H-carbazole-8-carboxylate; 9-(3-methoxybenzyl)-2,3,4,9-tetrahydro-1H-carbazole-8-carboxylic acid; methyl 9-(4-methoxybenzyl)-2,3,4,9-tetrahydro-1H-carbazole-8-carboxylate; 9-(4-methoxybenzyl)-2,3,4,9-tetrahydro-1H-carbazole-8-carboxylic acid; methyl 9-(2-methoxybenzyl)-2,3,4,9-tetrahydro-1H-carbazole-8-carboxylate; 9-(2-methoxybenzyl)-2,3,4,9-tetrahydro-1H-carbazole-8-carboxylic acid; methyl 9-(2-fluorobenzyl)-2,3,4,9-tetrahydro-1H-carbazole-8-carboxylate; 9-(2-fluorobenzyl)-2,3,4,9-tetrahydro-1H-carbazole-8-carboxylic acid; methyl 9-(3-fluorobenzyl)-2,3,4,9-tetrahydro-1H-carbazole-8-carboxylate; 9-(3-fluorobenzyl)-2,3,4,9-tetrahydro-1H-carbazole-8-carboxylic acid; methyl 9-(4-(trifluoromethyl)benzyl)-2,3,4,9-tetrahydro-1H-carbazole-8-carboxylate; 9-(4-(trifluoromethyl)benzyl)-2,3,4,9-tetrahydro-1H-carbazole-8-carboxylic acid; methyl 9-(3-(trifluoromethyl)benzyl)-2,3,4,9-tetrahydro-1H-carbazole-8-carboxylate; 9-(3-(trifluoromethyl)benzyl)-2,3,4,9-tetrahydro-1H-carbazole-8-carboxylic acid; methyl 9-(2,4-difluorobenzyl)-2,3,4,9-tetrahydro-1H-carbazole-8-carboxylate; 9-(2,4-difluorobenzyl)-2,3,4,9-tetrahydro-1H-carbazole-8-carboxylic acid; 9-[2-(trifluoromethyl)benzyl]-2,3,4,9-tetrahydro-1H-carbazole-8-carboxylic acid; methyl 9-(2,3-difluorobenzyl)-2,3,4,9-tetrahydro-1H-carbazole-8-carboxylate; 9-(2,3-difluorobenzyl)-2,3,4,9-tetrahydro-1H-carbazole-8-carboxylic acid; 9-(4-fluorobenzyl)-2,3,4,9-tetrahydro-1H-carbazole-8-carboxylic acid; methyl 9-(3-cyanobenzyl)-2,3,4,9-tetrahydro-1H-carbazole-8-carboxylate; 9-(3-carboxybenzyl)-2,3,4,9-tetrahydro-1H-carbazole-8-carboxylic acid; [8-(methoxycarbonyl)-1,2,3,4-tetrahydro-9H-carbazol-9-yl]acetic acid; methyl 9-(2-chloro-2-oxoethyl)-2,3,4,9-tetrahydro-1H-carbazole-8-carboxylate; methyl 9-(2-morpholin-4-yl-2-oxoethyl)-2,3,4,9-tetrahydro-1H-carbazole-8-carboxylate; 9-(2-morpholin-4-yl-2-oxoethyl)-2,3,4,9-tetrahydro-1H-carbazole-8-carboxylic acid; 9-[2-(dimethylamino)-2-oxoethyl]-2,3,4,9-tetrahydro-1H-carbazole-8-carboxylic acid; 9-[2-(diethylamino)-2-oxoethyl]-2,3,4,9-tetrahydro-1H-carbazole-8-carboxylic acid; 9-(2-amino-2-oxoethyl)-2,3,4,9-tetrahydro-1H-carbazole-8-carboxylic acid; 9-(2-oxo-2-pyrrolidin-1-ylethyl)-2,3,4,9-tetrahydro-1H-carbazole-8-carboxylic acid; 9-[2-(3-hydroxypiperidin-1-yl)-2-oxoethyl]-2,3,4,9-tetrahydro-1H-carbazole-8-carboxylic acid; 9-{2-[(2-hydroxyethyl)amino]-2-oxoethyl}-2,3,4,9-tetrahydro-1H-carbazole-8-carboxylic acid; methyl 9-benzyl-2,3,4,9-tetrahydro-1H-carbazole-7-carboxylate; 9-benzyl-2,3,4,9-tetrahydro-1H-carbazole-7-carboxylic acid; methyl 5-propyl-5,6,7,8,9,10-hexahydrocyclohepta[b]indole-4-carboxylate; 5-propyl-5,6,7,8,9,10-hexahydrocyclohepta[b]indole-4-carboxylic acid; 5-[2-(trifluoromethyl)benzyl]-5,6,7,8,9,10-hexahydrocyclohepta[b]indole-4-carboxylic acid; methyl 5-benzyl-5,6,7,8,9,10-hexahydrocyclohepta[b]indole-4-carboxylate; 5-benzyl-5,6,7,8,9,10-hexahydrocyclohepta[b]indole-4-carboxylic acid; methyl 5-(3-cyanobenzyl)-5,6,7,8,9,10-hexahydrocyclohepta[b] indole-4-carboxylate; 5-[3-(aminocarbonyl)benzyl]-5,6,7,8,9,10-hexahydrocyclohepta[b]indole-4-carboxylate; methyl 5-(4-cyanobutyl)-5,6,7,8,9,10-hexahydrocyclohepta[b]indole-4-carboxylate, 5-(5-amino-5-oxopentyl)-5,6,7,8,9,10-hexahydrocyclohepta[b]indole-4-carboxylic acid, 5-(4-cyanobutyl)-5,6,7,8,9,10-hexahydrocyclohepta[b] indole-4-carboxylic acid; methyl 5-(3-methoxybenzyl)-5,6,7,8,9,10-hexahydrocyclohepta[b] indole-4-carboxylate; 5-(3-methoxybenzyl)-5,6,7,8,9,10-hexahydrocyclohepta[b]indole-4-carboxylic acid; 5-(2-cyanobenzyl)-5,6,7,8,9,10-hexahydrocyclohepta[b]indole-4-carboxylic acid; 5-[2-(aminocarbonyl)benzyl]-5,6,7,8,9,10-hexahydrocyclohepta[b]indole-4-carboxylic acid; 9-benzyl-4-benzyloxyimino-2,3,4,9-tetrahydro-4H-carbazole-8-carboxylic acid; methyl 9-benzyl-4-(hydroxyimino)-2,3,4,9-tetrahydro-1H-carbazole-8-carboxylate; 9-benzyl-4-(hydroxyimino)-2,3,4,9-tetrahydro-1H-carbazole-8-carboxylic acid; 5-benzyl-10-(hydroxyimino)-5,6,7,8,9,10-hexahydrocyclohepta[b]indole-4-carboxylic acid; 9-benzyl-1-(trifluoroacetyl)-2,3,4,9-tetrahydro-1H-carbazole-8-carboxylic acid; methyl 5-(3-bromo-5-methoxybenzyl)-5,6,7,8,9,10-hexahydrocyclohepta[b]indole-4-carboxylate; 5-(3-bromo-5-methoxybenzyl)-5,6,7,8,9,10-hexahydrocyclohepta[b]indole-4-carboxylic acid; methyl 5-(3-cyano-5-methoxybenzyl)-5,6,7,8,9,10-hexahydrocyclohepta[b]indole-4-carboxylate; 5-[3-(aminocarbonyl)-5-methoxybenzyl]-5,6,7,8,9,10-hexahydrocyclohepta[b]indole-4-carboxylate; methyl 5-[(5-cyano-2-furyl)methyl]-5,6,7,8,9,10-hexahydrocyclohepta[b]indole-4-carboxylate; 5-{[(5-aminocarbonyl)-2-furyl]methyl}-5,6,7,8,9,10-hexahydrocyclohepta[b]indole-4-carboxylic acid; 5-(4,6-dimethoxy-pyrimidin-2-ylmethyl)-5,6,7,8,9,10-hexahydrocyclohepta[b]indole-4-carboxylic acid, 5-{[6-hydroxy-2-(methylthio)pyrimidin-4-yl]methyl}-5,6,7,8,9,10-hexahydrocyclohepta[b]indole-4-carboxylic acid; 5-[(4-hydroxy-6-methoxypyrimidin-2-yl)methyl]-5,6,7,8,9,10-hexahydrocyclohepta[b]indole-4-carboxylic acid; methyl 5-(pyridin-2-ylmethyl)-5,6,7,8,9,10-hexahydrocyclohepta[b]indole-4-carboxylate; 5-(pyridin-2-ylmethyl)-5,6,7,8,9,10-hexahydrocyclohepta[b]indole-4-carboxylic acid; methyl 5-[(6-chloropyridin-3-yl)methyl]-5,6,7,8,9,10-hexahydrocyclohepta[b]indole-4-carboxylate; 5-[(6-chloropyridin-3-yl)methyl]-5,6,7,8,9,10-hexahydrocyclohepta[b]indole-4-carboxylic acid; 5-[(2-cyanopyridin-4-yl)methyl]-5,6,7,8,9,10-hexahydrocyclohepta[b]indole-4-carboxylic acid; 5-{[2-(aminocarbonyl)pyridin-4-yl]methyl}-5,6,7,8,9,10-hexahydrocyclohepta[b]indole-4-carboxylic acid; methyl 5-[(6-cyanopyridin-2-yl)methyl]-5,6,7,8,9,10-hexahydrocyclohepta[b]indole-4-carboxylate; 5-{[6-(aminocarbonyl)pyridin-2-yl]methyl}-5,6,7,8,9,10-hexahydrocyclohepta[b]indole-4-carboxylic acid; methyl 5-(2-chloro-6-methoxypyridin-4-yl)-5,6,7,8,9,10-hexahydrocyclohepta[b]indole-4-carboxylate; (9-benzyl-2,3,4,9-tetrahydro-1H-carbazol-8-yl)methanol; N-hydroxy-5-[2-(trifluoromethyl)benzyl]-5,6,7,8,9,10-hexahydrocyclohepta[b]indole-4-carboxamide; N-[5-benzyl-6-(methylsulfonyl)-5,6,7,8,9,10-hexahydrocyclohepta[b]indol-4-yl]methanesulfonamide; N-(5-[2-(trifluoromethyl)benzyl]-5,6,7,8,9,10-hexahydrocyclohepta[b]indol-4-yl)methanesulfonamide; N-(5-[2-(trifluoromethyl)benzyl]-5,6,7,8,9,10-hexahydrocyclohepta[b]indol-4-yl)benzenesulfonamide; 9-benzyl-N-hydroxy-2,3,4,9-tetrahydro-1H-carbazole-8-carboxamide; 4-benzyl-1,2,3,4-tetrahydrocyclopenta[b]indole-5-carboxylic acid; 1-benzyl-2,3-dimethyl-1H-indole-7-carboxylic acid; 2-acetyl-5-benzyl-2,3,4,5-tetrahydro-1H-pyrido[4,3-b]indole-6-carboxylic acid; methyl 9-(3-nitrobenzyl)-2,3,4,9-tetrahydro-1H-carbazole-8-carboxylate; 9-[3-(acetylamino)benzyl]-2,3,4,9-tetrahydro-1H-carbazole-8-carboxylic acid; 9-(3-nitrobenzyl)-2,3,4,9-tetrahydro-1H-carbazole-8-carboxylic acid; 9-(3-bromobenzyl)-2,3,4,9-tetrahydro-1H-carbazole-8-carboxylic acid; methyl 5,6,7,8,9,10-hexahydrocyclohepta[b]indole-3-carboxylate; 5-(2-fluorobenzyl)-5,6,7,8,9,10-hexahydrocyclohepta[b]indole-4-carboxylic acid; 5-(3-fluorobenzyl)-5,6,7,8,9,10-hexahydrocyclohepta[b]indole-4-carboxylic acid; 5-(4-fluorobenzyl)-5,6,7,8,9,10-hexahydrocyclohepta[b]indole-4-carboxylic acid; 5-(2,4-difluorobenzyl)-5,6,7,8,9,10-hexahydrocyclohepta[b]indole-4-carboxylic acid; 5-(2,5-difluorobenzyl)-5,6,7,8,9,10-hexahydrocyclohepta[b]indole-4-carboxylic acid; 5-[3-(trifluoromethyl)benzyl]-5,6,7,8,9,10-hexahydrocyclohepta[b]indole-4-carboxylic acid; 5-[4-(trifluoromethyl)benzyl]-5,6,7,8,9,10-hexahydrocyclohepta[b]indole-4-carboxylic acid; 9-(2,6-difluorobenzyl)-2,3,4,9-tetrahydro-1H-carbazole-7-carboxylic acid; 9-(2-fluorobenzyl)-2,3,4,9-tetrahydro-1H-carbazole-7-carboxylic acid; 9-(3-fluorobenzyl)-2,3,4,9-tetrahydro-1H-carbazole-7-carboxylic acid; 9-(4-fluorobenzyl)-2,3,4,9-tetrahydro-1H-carbazole-7-carboxylic acid; 9-(2,5-difluorobenzyl)-2,3,4,9-tetrahydro-1H-carbazole-7-carboxylic acid; 9-(2,3-difluorobenzyl)-2,3,4,9-tetrahydro-1H-carbazole-7-carboxylic acid; 9-(2,4-difluorobenzyl)-2,3,4,9-tetrahydro-1H-carbazole-7-carboxylic acid, 9-[2-(trifluoromethyl)benzyl]-2,3,4,9-tetrahydro-1H-carbazole-7-carboxylic acid; 9-(4-(trifluoromethyl)benzyl)-2,3,4,9-tetrahydro-1H-carbazole-7-carboxylic acid; 5-(2,3-difluorobenzyl)-5,6,7,8,9,10-hexahydrocyclohepta[b]indole-4-carboxylic acid; 9-(2,6-difluorobenzyl)-2,3,4,9-tetrahydro-1H-carbazole-8-carboxylic acid; 9-(2,5-difluorobenzyl)-2,3,4,9-tetrahydro-1H-carbazole-8-carboxylic acid; 9-(3-methylbenzyl)-2,3,4,9-tetrahydro-1H-carbazole-8-carboxylic acid; 5-(3-fluorobenzyl)-5,6,7,8,9,10-hexahydrocyclohepta[b]indole-3-carboxylic acid; 5-(4-fluorobenzyl)-5,6,7,8,9,10-hexahydrocyclohepta[b]indole-3-carboxylic acid; 9-[3-(trifluoromethoxy)benzyl]-2,3,4,9-tetrahydro-1H-carbazole-8-carboxylic acid; 5-(2-fluorobenzyl)-5,6,7,8,9,10-hexahydrocyclohepta[b]indole-3-carboxylic acid; 9-[3-fluoro-5-(trifluoromethyl)benzyl]-2,3,4,9-tetrahydro-1H-carbazole-8-carboxylic acid; 9-[2-fluoro-6-(trifluoromethyl)benzyl]-2,3,4,9-tetrahydro-1H-carbazole-8-carboxylic acid; 9-(2-methylbenzyl)-2,3,4,9-tetrahydro-1H-carbazole-8-carboxylic acid; 9-(2,5-dichlorobenzyl)-2,3,4,9-tetrahydro-1H-carbazole-8-carboxylic acid; 9-(3,4-difluorobenzyl)-2,3,4,9-tetrahydro-1H-carbazole-8-carboxylic acid; 9-(2,3-difluorobenzyl)-3-methyl-2,3,4,9-tetrahydro-1H-carbazole-8-carboxylic acid; 9-(2-fluoro-3-methylbenzyl)-2,3,4,9-tetrahydro-1H-carbazole-8-carboxylic acid; dimethoxybenzyl)-2,3,4,9-tetrahydro-1H-carbazole-8-carboxylic acid; 9-(2-bromo-5-fluorobenzyl)-2,3,4,9-tetrahydro-1H-carbazole-8-carboxylic acid; 9-(3-phenoxybenzyl)-2,3,4,9-tetrahydro-1H-carbazole-8-carboxylic acid; 9-(2-fluorobenzyl)-3-methyl-2,3,4,9-tetrahydro-1H-carbazole-8-carboxylic acid; 9-(3-fluorobenzyl)-3-methyl-2,3,4,9- tetrahydro-1H-carbazole-8-carboxylic acid; 9-(4-fluorobenzyl)-3-methyl-2,3,4,9-tetrahydro-1H-carbazole-8-carboxylic acid; 9-(2,4-difluorobenzyl)-3-methyl-2,3,4,9-tetrahydro-1H-carbazole-8-carboxylic acid; 5-(3-methylbenzyl)-5,6,7,8,9,10-hexahydrocyclohepta[b]indole-4-carboxylic acid; 5-(4-methylbenzyl)-5,6,7,8,9,10-hexahydrocyclohepta[b]indole-4-carboxylic acid.

FABP5 inhibitors include indole derivatives (Lehmann et al 2004), triazolopyrimidinone derivative (Schering Corporation, PCT/US2009/063787), Pyrazole (BMS309403, Bristol Myers Squibb, described in Sulsky et al 2007), BMS480404 (Bristol Myers Squibb, described in McDonnell et al 2006).

Downregulation of Gene Expression Using siRNA siNA (e.g., siRNA) are well known in the art. For example, siRNA and double-stranded RNA have been described in U.S. Pat. Nos. 6,506,559 and 6,573,099, as well as in U.S. Patent Applications 2003/0051263, 2003/0055020, 2004/0265839, 2002/0168707, 2003/0159161, and 2004/0064842, all of which are herein incorporated by reference in their entirety.

Within a siNA, the components of a nucleic acid need not be of the same type or homogenous throughout (e.g., a siNA may comprise a nucleotide and a nucleic acid or nucleotide analog). Typically, siNA form a double-stranded structure; the double-stranded structure may result from two separate nucleic acids that are partially or completely complementary. In certain embodiments of the present invention, the siNA may comprise only a single nucleic acid (polynucleotide) or nucleic acid analog and form a double-stranded structure by complementing with itself (e.g., forming a hairpin loop). The double-stranded structure of the siNA may comprise 16, 20, 25, 30, 35, 40, 45, 50, 60, 65, 70, 75, 80, 85, 90 to 100, 150, 200, 250, 300, 350, 400, 450, 500 or more contiguous nucleobases, including all ranges therebetween. The siNA may comprise 17 to 35 contiguous nucleobases, or 18 to 30 contiguous nucleobases, or 19 to 25 nucleobases, or 20 to 23 contiguous nucleobases, or 20 to 22 contiguous nucleobases, or 21 contiguous nucleobases that hybridize with a complementary nucleic acid (which may be another part of the same nucleic acid or a separate complementary nucleic acid) to form a double-stranded structure.

Bioactive substances that are nucleic acids include, but are not limited to siRNAs. Typically, introduction of double-stranded RNA (dsRNA), which may alternatively be referred to herein as small interfering RNA (siRNA), induces potent and specific gene silencing, a phenomena called RNA interference or RNAi. This phenomenon has been extensively documented in the nematode *C. elegans* (Fire et al., 1998), but is widespread in other organisms, ranging from trypanosomes to mouse. Depending on the organism being discussed, RNA interference has been referred to as "cosuppression," "post-transcriptional gene silencing," "sense suppression," and "quelling." RNAi is an attractive biotechnological tool because it provides a means for knocking out the activity of specific genes.

In designing RNAi there are several factors that need to be considered such as the nature of the siRNA, the durability of the silencing effect, and the choice of delivery system. To produce an RNAi effect, the siRNA that is introduced into the organism will typically contain exonic sequences. Furthermore, the RNAi process is homology dependent, so the sequences must be carefully selected so as to maximize gene specificity, while minimizing the possibility of cross-interference between homologous, but not gene-specific sequences. Preferably the siRNA exhibits greater than 80, 85, 90, 95, 98,% or even 100% identity (or any range derivable therein) between the sequence of the siRNA and the gene to be inhibited. Sequences less than about 80% identical to the target gene are substantially less effective. Thus, the greater homology between the siRNA and the FABP gene to be inhibited, the less likely expression of unrelated genes will be affected. In certain embodiments, there is at least 80, 85, 90, 95, 98,% or even 100% identity or complementarity (or any range derivable therein) to an entire FABP4 sequence of SEQ ID NO: 2 (GenBank accession NM_001442) that is provided herein or to a region of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 contiguous nucleotides (or any range derivable therein) from SEQ ID NO: 2 provided herein.

In addition, the size of the siRNA is an important consideration. In some embodiments, the present invention relates to siRNA molecules that is preferably less than 500, 200, 100, 50 or 25 nucleotides in length, and are able to modulate the FABP gene expression. In the context of the present invention, the siRNA is preferably from about 20 nucleotides to about 60 nucleotides in length.

siRNA can be obtained from commercial sources, natural sources, or can be synthesized using any of a number of techniques well-known to those of ordinary skill in the art. For example, one commercial source of predesigned siRNA is Ambion®, Austin, Tex. Another is Qiagen® (Valencia, Calif.). An inhibitory nucleic acid that can be applied in the compositions and methods of the present invention may be any nucleic acid sequence that has been found by any source to be a validated downregulator of a particular protein.

The siRNA may also comprise an alteration of one or more nucleotides. Such alterations can include the addition of non-nucleotide material, such as to the end(s) of the 19 to 25 nucleotide RNA or internally (at one or more nucleotides of the RNA). In certain aspects, the RNA molecule contains a 3'-hydroxyl group. Nucleotides in the RNA molecules of the present invention can also comprise non-standard nucleotides, including non-naturally occurring nucleotides or deoxyribonucleotides. The double-stranded oligonucleotide may contain a modified backbone, for example, phosphorothioate, phosphorodithioate, or other modified backbones known in the art, or may contain non-natural internucleoside linkages. Additional modifications of siRNAs (e.g., 2'-O-methyl ribonucleotides, 2'-deoxy-2'-fluoro ribonucleotides, "universal base" nucleotides, 5-C-methyl nucleotides, one or more phosphorothioate internucleotide linkages, and inverted deoxyabasic residue incorporation) can be found in U.S. Application Publication 20040019001 and U.S. Pat. No. 6,673,611 (each of which is incorporated by reference in its entirety). Collectively, all such altered nucleic acids or RNAs described above are referred to as modified siRNAs.

In some embodiments, RNAi is capable of decreasing the expression of a particular protein, by at least 10%, 20%, 30%, or 40%, more preferably by at least 50%, 60%, or 70%, and most preferably by at least 75%, 80%, 90%, 95% or more. In the context of the present disclosure, the particular protein is FABP4.

The siRNA may be a small hairpin RNA (shRNA). shRNA are RNA sequences that include a hairpin turn that can be used to silence gene expression via RNA interference. The shRNA hairpin structure is cleaved in the cell to siRNA. shRNAs can be synthesized exogenously or can be transcribed from RNA polymerase promoters in vivo. shRNA may also be a DNA molecule that can be cloned into an expression vector, such as a plasmid, a lentiviral particle, to express siRNA.

In some embodiments, the present invention relates to shRNA molecules that are able to modulate the FABP gene, in particular, FABP4 gene expression. Preferably, the shRNA is capable of decreasing the expression of a particular protein, by at least 10%, 20%, 30%, or 40%, more preferably by at least 50%, 60%, or 70%, and most preferably by at least 75%, 80%, 90%, 95% or more. In the context of the present disclosure, the particular protein is FABP4.

In some embodiments, the shRNA molecule comprises a sequence of SEQ ID NO: 1. In certain embodiments, there is at least 80, 85, 90, 95, 98,% or even 100% identity (or any range derivable therein) to an entire SEQ ID NO: 1 that is provided herein or to a region of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 contiguous nucleotides (or any range derivable therein) from SEQ ID NO: 1 provided herein.

Combination Therapy

In order to increase the effectiveness of the compositions and methods described herein, it may be desirable to combine these compositions or methods with other agents or therapy methods, such as anti-cancer agents. An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting or stopping tumor growth, reducing the blood supply to a tumor or cancer cells, promoting an immune response against cancer cells or a tumor, preventing or inhibiting the progression of cancer, or increasing the lifespan of a subject with cancer. More generally, these other compositions or therapies would be provided in a combined amount effective to kill or inhibit proliferation of the cell. This process may involve contacting the cells with the FABP inhibitor compositions described herein and the agent(s) or multiple factor(s) at the same time. This may be achieved by contacting the cell with a single composition or pharmacological formulation that includes both agents, or by contacting the cell with two distinct compositions or formulations, at the same or different time, wherein one composition includes the FABP inhibitor and the other includes the second agent(s) or therapy.

One goal of cancer research is to find ways to improve the efficacy of chemo- and radiotherapy. In the context of the present invention, it is contemplated that the FABP inhibitors described herein could be used in conjunction with chemotherapeutic, radiotherapeutic, or immunotherapeutic intervention, in addition to other anti-cancer agents or therapy. Administration of the described compositions can precede or follow a second anti-cancer therapy or agent by intervals ranging from minutes to weeks. In embodiments where the second therapy or agent is applied separately to the cell or subject, one would generally ensure that a significant period of time did not expire between the time of each delivery, such that the treatments would still be able to exert an advantageously combined effect on the cell, tumor, or subject. In such instances, it is contemplated that one may contact the cell with or administer both modalities within about 12-24 hours of each other and, more preferably, within about 6-12 hours of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

Various combinations may be employed, the FABP inhibitor is "A" and the secondary agent, such as radio- or chemotherapy, is "B":

```
A/B/A  B/A/B  B/B/A  A/A/B  A/B/B  B/A/A  A/B/B/B
B/A/B/B  B/B/B/A  B/B/A/B  A/A/B/B  A/B/B/A  A/B/B/A
B/B/A/A  B/A/B/A  B/A/A/B  A/A/B/B  B/A/B/A  A/B/A/A
A/A/B/A
```

Administration of the therapeutic compositions of the present invention to a patient will follow general protocols of administration, taking into account the toxicity, if any. It is expected that the treatment cycles would be repeated as necessary. It also is contemplated that various standard therapies, as well as surgical intervention, may be applied in combination with the described therapy.

A. Chemotherapy

Cancer therapies include a variety of therapies that are both chemical and radiation based treatments. Chemotherapies include, for example, cisplatin (CDDP), carboplatin, oxaliplatin, irinotecan, topotecan, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxane, docetaxel, paclitaxel, ABRAXANE™, gemcitabine, navelbine, farnesyl-protein transferase inhibitors, transplatinum, 5-fluorouracil, vincristin, vinblastin, methotrexate, medroxy-progesterone acetate or any analog or derivative variant of the foregoing.

Other examples of chemotherapy include Receptor Tyrosine Kinase Inhibitors (RTKi) which include but are not limited to, Herceptin (Genentech), Laptinib (GSK), Tarceva (Genentech/OSI), Gefitinib (AstraZeneca), Fluoro-Sorafenib (Bayer), Sorafenib (Bayer), PF-2341066 (Pfizer), or any analog or derivative variant thereof. It is specifically contemplated that any of these compounds or derivatives or analogs, can be used in these combination therapies.

Furthermore, chemotherapy also includes PARP inhibitors, which include but are not limited to 4-[(3-[(4-cyclopropylcarbonyl)piperazin-4-yl]carbonyl)-4-fluorophenyl]methyl(2H)phthalazin-1-one (Olaparib; AZD2281; KU0059436, AstraZeneca), 2-[(2R)-2-methylpyrrolidin-2-yl]-1H-benzimidazole-4-carboxamide (ABT-888, Abbott Laboratories), benzimidazole derivative (ABT-472, Abbott Laboratories), O-(3-piperidino-2-hydroxy-1-propyl)nicotinic amidoxime (BGP15, Allos Therapeutics), AZD2461 (AstraZeneca), BMN673 (BioMarin Pharmaceutical Inc), 3-[2-fluoro-5-(4-oxo-3,4-dihydro-phthalazin-1-ylmethyl)-phenyl]-5-methyl-imidazolidine-2,4-dione, 3-[3-(5,8-difluoro-4-oxo-3,4-dihydro-phthalazin-1-ylmethyl)-phenyl]-5-methyl-imidazoline-2,4-dione, 5-chloro-2-{1-[3-([1,4]diazepane-1-carbonyl)-4-fluoro-phenyl]-ethoxy}-benzamide, 2-{3-[2-fluoro-5-(4-oxo-3,4-dihydro-phthalazin-1-ylmethyl)-phenyl]-5-methyl-2,4-dioxo-imidazolidin-1-yl}-acetamide, -4-[3-(4-Cyclopropanecarbonyl-piperazine-1-carbonyl)-4-fluoro-benzyl]-2H-phthalazin-1-one, 3-[2-fluoro-5-(4-oxo-3,4,dihydro-phthalazin-1-ylmethyl)-phenyl]-5,5-dimethyl-1-[2-(4-methyl-piperazin-1-yl)-2-oxo-ethyl]-imidazoline-2,4-dione, 8-fluoro-2-(4-methylaminomethyl-phenyl) 1,3,4,5-tetrahydro-azepino[5,4,3-cd]indol-6-one (WO2008020180), BSI101 (BiPar Sciences), CE9722 (Cephalon Inc), GPI21016 (Eisai Co), PARP Inhibitor ROCHE (F. Hoffman-La Roche Ltd), Indoles (INO1001, Genentech), PARP Inhibitors INOTEK (Inotek Pharmaceuticals Co), (S)-2-(4-(piperidin-3-yl)phenyl)-2H-indazole-7-carboxamide hydrochloride (MK4827, Merck & Co), MP124 (Mitsubishi Tanabe Pharma Co), ONO2231 (Ono Pharmaceutical Co Ltd), LT673 (LEAD Therapeutics), Indole derivative (PF1367338, Pfizer), 2-quinolinones and 2-quinoxalinones (U.S. Pat. No. 7,879, 857), 2-alkyl quinazolinone derivatives (U.S. Pat. No. 7,875, 621), 2-pyridone derivatives (U.S. Pat. No. 7,863,280), Pyrrolo[1,2-a]pyrazin-1(2H)-one and pyrrolo[1,2-d][1,2,4]triazin-1(2H)-one derivatives (U.S. Pat. No. 7,834,015), Thieno[2,3-c]isoquinolines (U.S. Pat. No. 7,825,129), Phthalazinone derivatives (U.S. Pat. No. 7,092,193), Indenoisoquinolinone (U.S. Pat. No. 7,652,028), 1H-benzimidazole-4-carboxamides (U.S. Pat. No. 7,595,406), 4-(Substituted aryl)-5-hydroxyisoquinolinone derivative (U.S. Pat. No. 7,425,563), and fused pyridazine derivatives (U.S. Pat. No. 7,402,580).

B. Radiotherapy

Other factors that cause DNA damage and have been used extensively include what are commonly known as γ-rays, X-rays, electron-beam radiation and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, tumor, or subject, are used herein to describe the process by which a therapeutic or a chemotherapeutic or a radiotherapeutic agent are delivered to a target or are placed in direct juxtaposition with the target cell. To achieve cell killing or stasis, both agents are delivered in a combined amount effective to treat a tumor or other condition.

C. Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy, thus, could be used as part of a combined therapy, in conjunction with a therapy described herein. Generally, a tumor cell target bears some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

D. Surgery

Approximately 90% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Upon excision of part or all of cancerous cells, tissue, or tumor, a cavity may be formed in the body. Treatment may be accomplished by perfusion, direct injection or local application of the area with an additional anti-cancer therapy (e.g. intra-peritoneal chemo- or immune therapy). Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

E. Other agents

It is contemplated that other agents may be used in combination with the present invention to improve the therapeutic efficacy of treatment.

Hormonal therapy may also be used in conjunction with the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

Other methods and compositions further include administering anti-angiogenic agents including, but not limited to, Nexavar (Bayer), Thalidomide (Celgene), Avastin (Genentech), Cilengitide (Merck KGaA), Exherin (Adherex), WX-UK1, Combretastatin A-4 phosphate, GCS-100LE (Prospect Therapeutics), PTK/ZK (Novartis), AS-1404 (Antisoma), Phosphomannopentose sulfate, Squalamine, talactoferrin alfa, ZD-6474 (AstraZeneca), AP-23573 (Ariad), Volociximab (Biogen Idec), XL-999, XL-880, XL-164 (Exelixis, Inc.), or any analog or derivative variant thereof.

Other methods and composition further include administering c-Met inhibitors, including but not limited to, PHA665752 (Pfizer, Inc.), SU11274 (Sugen, Inc.), SU11271 (Sugen, Inc.), SU11606 (Sugen, Inc.), ARQ197 (ArQuleArqule, Inc.), MP470 (Supergen, Inc.), Kirin, XL-880 (Exelixis, Inc.), XL184 (Exelixis, Inc.) Geldanamycins, SGX523 (SGX, Inc.), MGCD265 (MethylGene, Inc.), HPK-56 (Supergen, Inc.), AMG102 (Amgen, Inc.), MetMAb (Genentech, Inc.), ANG-797 (Angion Biomedica Corp.), CGEN-241 (Compugen LTD.), Metro-F-1 (Dompe S.p.A.), ABT-869 (Abbott Laboratories) and K252a, or any analog or derivative thereof.

Cancers and Hyperproliferative Conditions

In some methods of the invention, the cancer cell is a tumor cell. Furthermore, the cell may be administered compositions of the invention in vitro, in vivo, or ex vivo. Thus, the cancer cell may be in a patient. The patient may have a solid tumor. In such cases, embodiments may further involve performing surgery on the patient, such as by resecting all or part of the tumor. The compositions described herein may be administered to the patient before, after, or at the same time as surgery. In additional embodiments, patients may also be administered the compositions directly, endoscopically, intratracheally, intratumorally, intravenously, intralesionally, intramuscularly, intraperitoneally, regionally, percutaneously, topically, intrarterially, intravesically, subcutaneously, infusion, or continuous infusion. The compositions may be administered 1, 2, 3, 4, 5, 6, 7, 8, 9, 10, 11, 12, 13, 14, 15, 16, 17, 18, 19, 20 or more times, and they may be administered every 1, 2, 3, 4, 5, 6, 7, 8, 9, 10, 11, 12, 13, 14, 15, 16, 17, 18, 19, 20, 21, 22, 23, 24 hours, or 1,2,3, 4, 5, 6, 7 days, or 1, 2, 3, 4, 5 weeks, or 1, 2, 3, 4, 5, 6, 7, 8, 9, 10, 11, 12 months.

In certain aspects, a FABP inhibitor is provided to a patient intravenously. In certain embodiments, the infusion rate is initially from about 0.1, 1, 2, 3, 4, 5, pg, ng or μg/kg/min to about 2, 3, 4, 5, 10 pg, ng or μg/kg/min, including all ranges and values there between. The infusion rate may be modified about every 1, 5, 15, 20, 25, 30, 40, 50, 100 minutes or so. The increase in rate of administration is limited by side effects (flushing, diarrhea, leg pain). In certain embodiments, the infusion rate is modified less frequently than every 15 minutes. In other embodiments, the infusion rate is modified more frequently than about every 15 minutes. Due to mobile intravenous pumps, a patient may receive FABP inhibitor intravenously for extended periods of time. The length of time of infusion and/or the rate of infusion may be modified based upon the response of the patient to the treatment. In certain embodiments of the present invention, the age and physical condition of the patient may warrant a reduction of the rate of infusion. In other embodiments, when the patient is not suffering any side effects from the treatment, the infusion rate is raised.

In some embodiments, the cancer cell that is administered the FABP4 inhibitors described herein may be a bladder, blood, bone, bone marrow, brain, breast, colorectal, esophagus, gastrointestine, head, kidney, liver, lung, nasopharynx, neck, ovary, pancreas, prostate, skin, stomach, testicular, tongue, or uterus cell.

Cancers that may be treated by using FABP inhibitors include cells and cancer cells from the bladder, blood, bone, bone marrow, brain, breast, colon, esophagus, gastrointestine, gum, head, kidney, liver, lung, nasopharynx, neck, ovary, pancreas, prostate, skin, stomach, sympathetic nerve, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; Paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; Kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; Ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's lymphoma; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

Pharmaceutical Formulations

Pharmaceutical compositions of the present invention comprise an effective amount of one or more FABP inhibitor and, in some cases, an additional agent, dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. For animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

The FABP inhibitor composition may comprise different types of carriers depending on whether it is to be administered in solid, liquid or aerosol form, and whether it need to be sterile for such routes of administration as injection. The present invention can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g, liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The FABP inhibitor may be formulated into a composition in a free base, neutral or salt form. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

The FABP inhibitor compositions are provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of a the composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present invention, the FABP inhibitor is combined with the carrier in any convenient and practical manner, i.e., by solution, suspension, emulsification, admixture, encapsulation, absorption and the like. Such procedures are routine for those skilled in the art. The FABP inhibitor can be combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

The actual dosage amount of a composition of the present invention administered to a subject can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 0.1% to about 20% of the weight of the unit, or between about 0.2% to about 2%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

A. Alimentary Compositions and Formulations

In certain aspects, the FABP inhibitor is formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In a further aspect, the FABP inhibitors may be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579 and 5,792, 451, each specifically incorporated herein by reference in its entirety). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No. 5,629, 001. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

Additional formulations which are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

B. Parenteral Compositions and Formulations

In certain aspects, FABP inhibitor may be administered via a parenteral route. As used herein, the term "parenteral" includes routes that bypass the alimentary tract. Specifically, the pharmaceutical compositions disclosed herein may be administered for example, but not limited to intravenously, intradermally, intramuscularly, intraarterially, intrathecally, subcutaneously, or intraperitoneally U.S. Pat. Nos. 6,7537,514, 6,613,308, 5,466,468, 5,543,158; 5,641,515; and 5,399,363 (each specifically incorporated herein by reference in its entirety).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution the solution should be suitably buffered if necessary and the liquid diluent first rendered isotonic with sufficient saline or glucose. These particular aqueous solutions are especially suitable for intravenous, intramuscular, subcutaneous, and intraperitoneal administration. Sterile aqueous media are known to those of skill in the art. One dosage may be dissolved in isotonic NaCl solution and either added hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions can be prepared by incorporating the FABP inhibitor in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

C. Miscellaneous Pharmaceutical Compositions and Formulations

In other aspects, the FABP inhibitor may be formulated for administration via various miscellaneous routes, for example, topical (i.e., transdermal) administration, mucosal administration (intranasal, vaginal, etc.) and/or inhalation.

Pharmaceutical compositions for topical administration may include the FABP inhibitor formulated for a medicated application such as an ointment, paste, cream or powder. Ointments include all oleaginous, adsorption, emulsion and water-solubly based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of the present invention may also comprise the use of a "patch". For example, the patch may supply one or more active substances at a predetermined rate and in a continuous manner over a fixed period of time.

The skilled artisan can consult Remington's Pharmaceutical Sciences, 18th Ed. Mack Printing Company, 1990, incorporated by reference herein in its entirety, for information about pharmaceutical compositions and delivery.

EXAMPLES

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1

Figure 2:
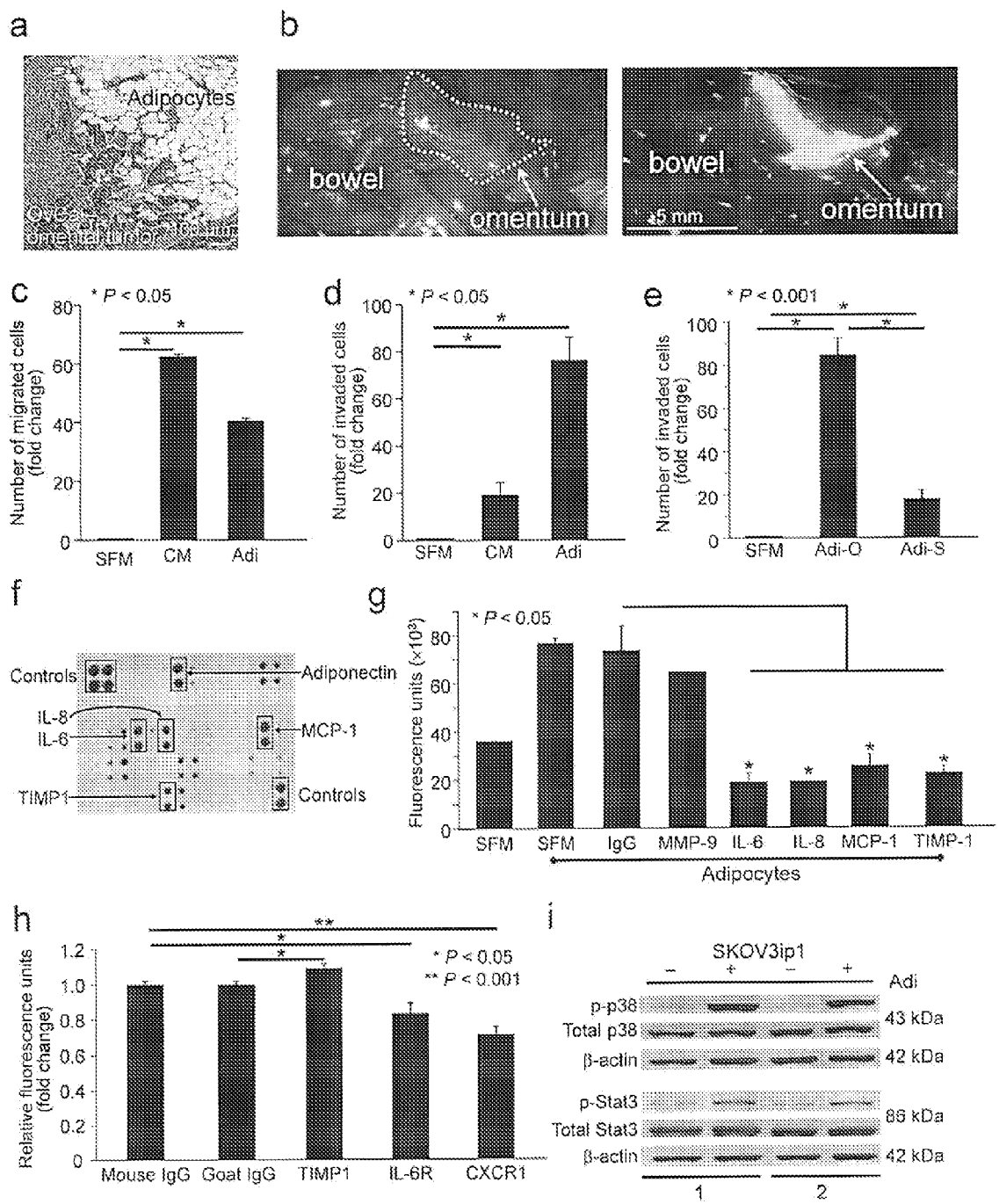
FIGS. 2a-2i Adipocytes promote homing of ovarian cancer cells to the omentum. (a) H&E staining of ovarian cancer (OvCa) tumor cells invading adipocytes in the human omentum. (b) In vivo homing assay. Fluorescently-labeled SKOV3ip1 human ovarian cancer cells were injected intraperitoneally into nude mice. Cancer cell localization was detected after 20 min (n=6 mice). The mouse omentum is outlined in the bright-field image (left) and visible in the fluorescent image (right). (c,d) Migration (c) and invasion (d) of SKOV3ip1 cells toward serum-free medium (SFM), adipocyte-conditioned medium (CM) and primary human omental adipocytes (Adi). Bars report mean fold change±s.e.m. One of three experiments, each using a different human subject samples, is shown. (e) Invasion of SKOV3ip1 cells comparing primary human omental (Adi-O) and subcutaneous (Adi-S) adipocytes from the same individual. Bars report mean fold change±s.e.m. One of two experiments shown. (f) Cytokine expression in conditioned medium from primary human omental adipocytes. One of 4 arrays shown. (g) Fluorescence intensity of labeled SKOV3ip1 cells that homed to Matrigel plugs containing SFM or adipocytes in the presence or absence of inhibitory antibodies. Bars report means±s.e.m. One of three experiments shown. (h) Fluorescence intensity of labeled SKOV3ip1 cells that adhered to sections of human omentum. SKOV3ip1 cells were pretreated with a CXCR1- or IL-6R-blocking antibodies or whole omentum sections were pretreated with a TIMP-1 inhibitory antibody (n=5 sections per group). Bars report means±s.e.m from one of three experiments. (i) Immunoblot of total and phosphorylated (p) p38 (Thr180/Tyr182) and Stat3 (Ser727) in SKOV3ip1 cells cultured alone (−) or with (+) adipocytes from two human subject samples for 24 h. One of three experiments shown.

Adipocytes Promote Ovarian Cancer Metastasis and Provide Energy for Rapid TMOR Growth Most ovarian cancers (OvCa) are diagnosed at an advanced stage when the tumor is widely metastatic (Landen et al., 2008; Cho and Shih, 2009). The most common subtype is serous ovarian cancer, which may arise from the surface of the ovary or, as recently suggested, the fimbriated end of the fallopian tube (Folkins, A. K., Jarboe, E. A., Roh, M. H. & Crum, C. P. Precursor to pelvic serous carcinoma and their clinical implications. Gynecol. Oncol. 113, 391-396 (2009).) The main site of ovarian cancer metastasis is the omentum, and 80% of all women with serous ovarian carcinoma present with omental metastases. The omentum, a large (20×12×3 cm) fat pad that extends from the stomach and covers the bowels (FIG. 1a), is the predominant form of visceral adipose tissue in humans, functioning as an endocrine organ and storage site for energy-dense lipids (Lengyel, 2010). Ovarian cancer metastasis to the omentum results in transformation of this soft pad of tissue, primarily composed of adipocytes, to a solid tumor histologically devoid of adipocytes (FIG. 1b and FIG. 2a). If metastasis were a random event, all organs in contact with peritoneal fluid would have an equal distribution of metastases. However, both primary and recurrent high-grade serous ovarian carcinomas preferentially metastasize to adipose tissue. The molecular mechanisms underlying this predilection are unknown. Recognizing the importance of the microenvironment in metastasis, the inventors considered the possibility that adipocytes contribute to the metastatic cascade.

Figure 3:
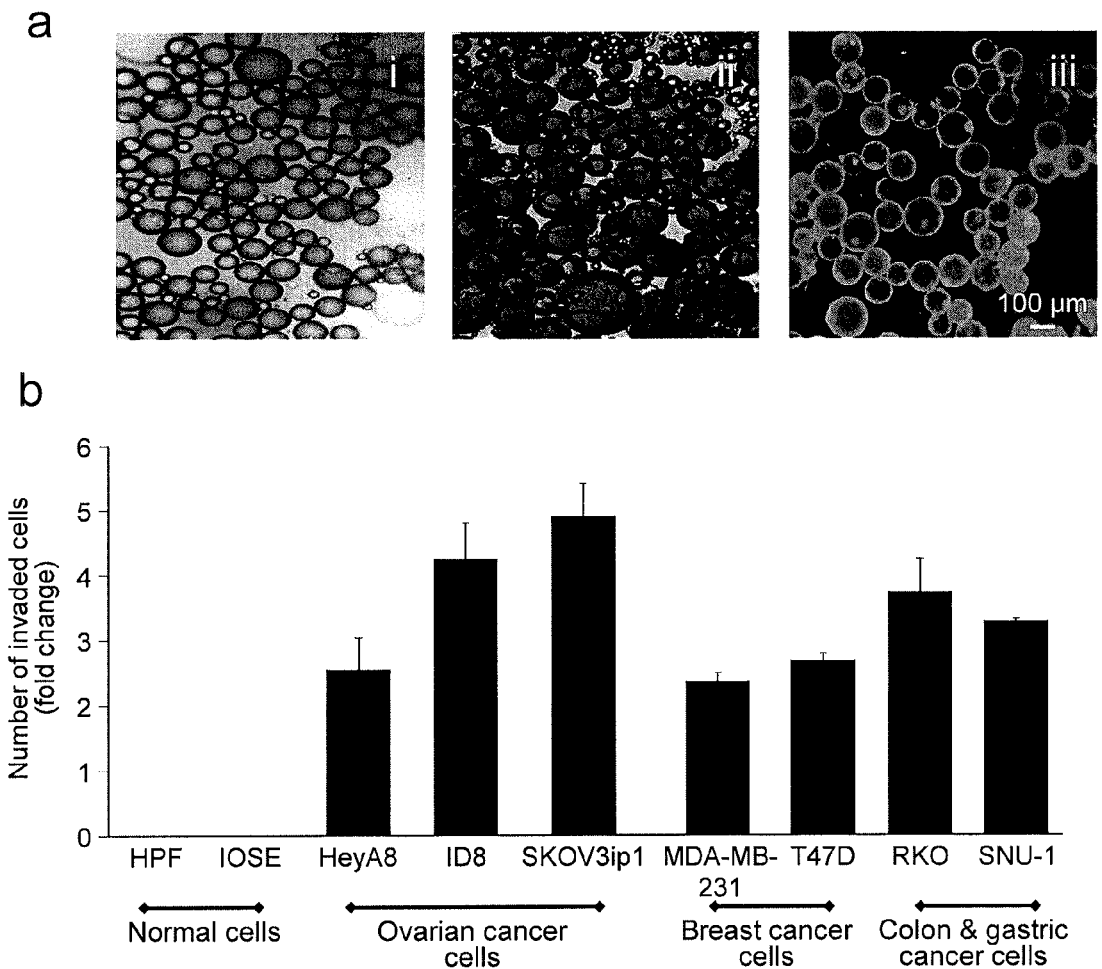
FIGS. 3a-3b. Adipocytes induce invasion of multiple cancer cells. (a) Adipocyte isolation. Primary human omental tissues were collected during surgical procedures for benign disease and primary human adipocytes were extracted. Adipocytes were visualized (200×) by (i) phase-contrast, (ii) stained with oil red o to confirm the extraction of mature adipocytes, and (iii) by fluorescence microscopy with Calcein AM to confirm viability. (b) Invasion assay. Primary human omental fibroblasts (HPF), immortalized ovarian surface epithelial (IOSE) cells, human ovarian cancer (OvCa) cells (HeyA8 and SKOV3ip1), mouse OvCa cells (ID8), breast cancer cells (MDA-MB-231 and T47D), colon cancer cells (RKO), and gastric cancer cells (SNU-1) invaded toward primary omental adipocytes. Bars report mean fold change±s.e.m., as compared to the serum-free medium control.

Ovarian cancer metastasis can be mimicked in female athymic nude mice by injecting fluorescently-labeled SKOV3ip1 human ovarian cancer cells intraperitoneally. After 20 min, a majority of tumor cells homed to the omentum (FIG. 2b). Because most cells in the omentum are adipocytes, thus the inventors determined whether purified (Rodbell, 1964), and viable adipocytes from normal human omentum (FIG. 3a) promoted the early steps of ovarian cancer metastasis, migration and invasion. Using a Boyden chamber, SKOV3ip1 human ovarian cancer cells were placed in the top chamber and adipocytes or conditioned-medium from adipocytes in the bottom chamber. Human omental adipocytes induced migration of SKOV3ip1 cells, which was likely mediated by soluble factors, given omental adipocyte-conditioned medium had a greater effect than omental adipocytes (FIG. 2c). Invasion was more potently stimulated by direct contact between omental adipocytes and cancer cells (FIG. 2d). Comparing omental with subcutaneous adipocytes, the omental adipocytes were significantly more efficient in promoting invasion. (FIG. 2e). This invasion-promoting activity of omental adipocytes was not only observed with OvCa cell lines, but also with gastric, colon, and breast cancer cell lines (FIG. 3b). Moreover, neither nontransformed human ovarian surface epithelial cells nor primary omental fibroblasts invaded in the presence of adipocytes.

Figure 4:
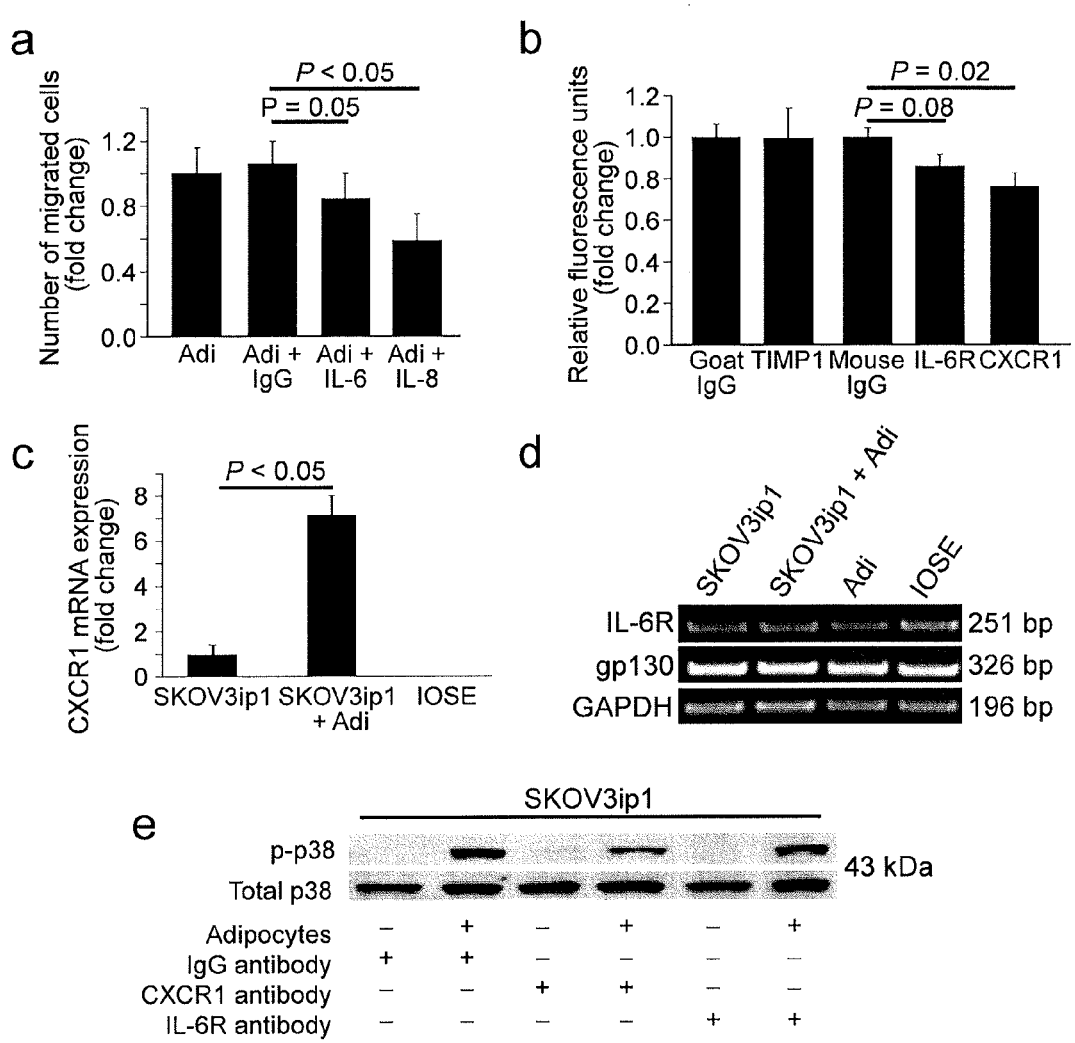
FIGS. 4a-4e. Adipokine and receptor inhibition reduce migration, homing and mitogenic signaling. (a) In vitro migration toward primary human omental adipocytes (Adi) after 1 h pretreatment with interleukin (IL)-8 or -6 inhibitory antibodies. Bars report mean fold change ±s.e.m. (b) In vivo mouse homing assay. Fluorescently-labeled SKOV3ip1 ovarian cancer cells were pretreated with inhibitory antibodies to the IL-6 receptor (R), IL-8R (CXCR1), or a control mouse IgG. Alternatively, the animals were pre-injected with the inhibitory antibodies, TIMP1 and control goat IgG. SKOV3ip1 cells were injected intraperitoneally into nude mice, the omentum was excised 20 min later, and fluorescence intensity measured after digestion. Bars report mean fold change±s.e.m (c) Quantitative RT-PCR for CXCR1 using RNA from IOSE cells, SKOV3ip1 cells alone, and cocultured with human adipocytes. Bars report mean fold change relative to glyceraldehyde 3-phosphate dehydrogenase (GAPDH) expression±s.e.m. (d) RT-PCR for IL-6R, glycoprotein (gp) 130 (IL-6R accessory protein), and GAPDH using RNA from SKOV3ip1 cells alone or cocultured with human adipocytes, human adipocytes alone, and IOSE cells. (e) SKOV3ip1 cells were pretreated with IL-6R or CXCR1 neutralizing antibodies and cultured with (+) or without (−) adipocytes prior to immunoblotting for the indicated proteins.

To identify factors responsible for attracting OvCa cells to the omentum, a cytokine array was performed (FIG. 2f). Among 62 cytokines tested, the five cytokines most abundantly secreted by omental adipocytes were IL-6, IL-8, monocyte chemoattractant protein-1 (MCP-1), tissue inhibitor of metalloproteinases-1 (TIMP-1) and adiponectin. It was confirmed that these five cytokines are highly expressed in adipocyte-conditioned medium using a fluorescent bead-based assay (data not shown). Antibody-mediated inhibition of IL-6, IL-8, MCP-1 and TIMP-1 resulted in a reduction of in vitro ovarian cancer cell homing toward adipocytes by at least 50% (FIG. 2g). Inhibition of IL-6 and IL-8 receptor (IL-6R, IL-8R), as well as their ligands, IL-6 and IL-8, using neutralizing antibodies (Merritt, W. M. et al. 2008, Nilsson, M. B. et al. 2005), reduced adhesion of SKOV3ip1 cells to sections of human omentum and migration towards primary human omental adipocytes in vitro (FIG. 2h and FIG. 4a). A neutralizing antibody against the IL-8R (CXCR1) reduced in vivo homing of ovarian cancer cells to the mouse omentum more efficiently than did an IL-6R-specific inhibitory antibody (FIG. 4b). Notably, CXCR1 expression was strongly upregulated in ovarian cancer cells, whereas the expression of IL-6R or its accessory protein, glycoprotein 130 (gp130), remained unchanged after cocultivation with adipocytes (FIG. 4c,d). Congruently, mitogenic signaling was induced by IL-8 (Merritt et al., 2008)), including p38 mitogen-activated protein kinase and signal transducer and activator of transcription 3 phosphorylation (FIG. 2i). Activation of p38 was partially reversed by a CXCR1-neutralizing antibody (FIG. 4e). These data indicated that adipocytes promote the early steps of ovarian cancer metastasis to the omentum, although a mechanistic explanation for the prevalence of omental metastatic tumors in women with ovarian cancer remained elusive.

Figure 6:
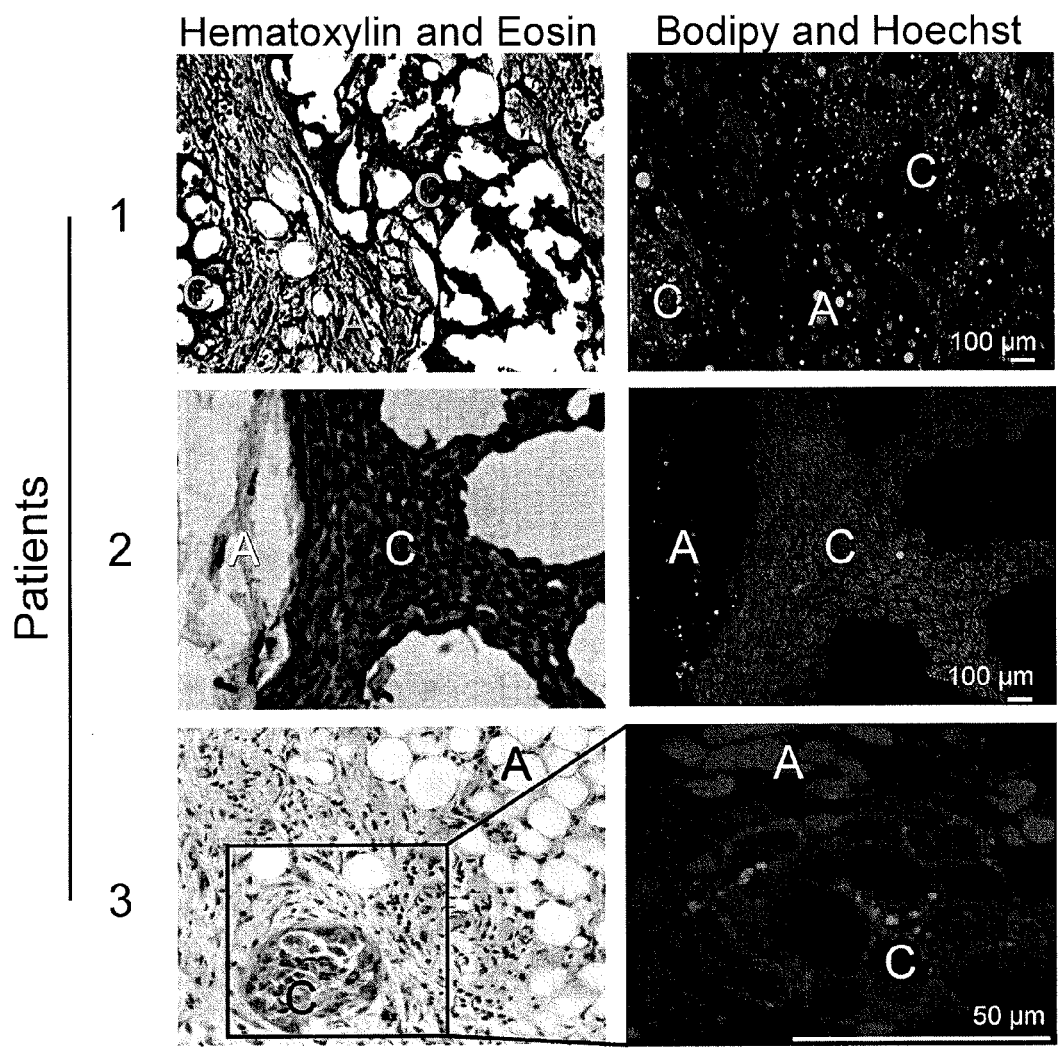
FIG. 6 Lipid accumulation in human ovarian cancer. Neutral lipid staining in sections of omental metastatic tissue from three ovarian cancer patients (nuclear counterstaining) and visualized by confocal microscopy (right panels). The corresponding hematoxylin and eosin section is in the left panels (A, adipocytes; C, cancer cells)
Figure 7:
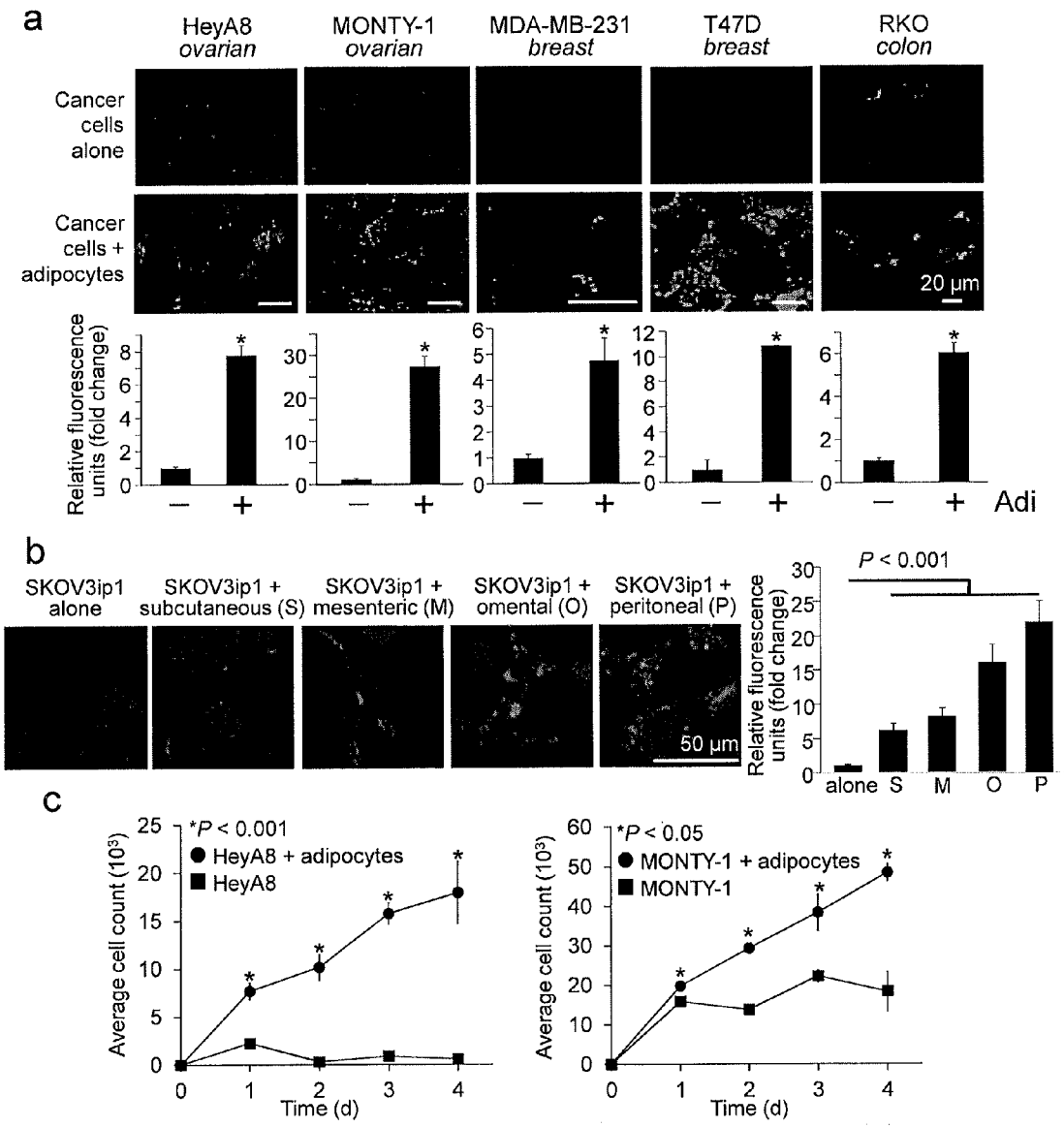
FIGS. 7a-7c Cocultured ovarian cancer cells accumulate lipids and proliferate. (a) Neutral lipid staining shows lipid accumulation in cancer cells. Coculture of ovarian (HeyA8, MONTY-1), colon (RKO), and breast cancer cells (MDA-MB-231, T47D) with primary human omental adipocytes (Adi) results in cytoplasmic lipid accumulation as evident by confocal microscopy (nuclear counterstain). The fluorescence intensity is quantified in the lower panel where bars report mean relative fluorescence±s.e.m. (*=P<0.001). (b) Representative images (left) of lipid accumulation in SKOV3ip1 cells following coculture with an equal number of adipocytes harvested from different anatomic sites (subcutaneous (S); bowel mesentery (M); omental (O); peritoneal (P)). Bars (right) report the mean relative fluorescence±s.e.m. (c) Adipocytes were cocultured with HeyA8 or MONTY-1 ovarian cancer cells and proliferation was measured over four days. The mean number of cells±s.e.m is reported for each day FIGS. 8a-8h Cocultivation of ovarian cancer cells with adipocytes activates lipolysis in adipocytes and β-oxidation in cancer cells. (a,b) Free fatty acid (a) and glycerol release (b) are detected in primary human adipocytes cultured alone or with SKOV3ip1 cells alone. Bars report means±s.e.m from one of two experiments, completed using different human subject samples. (c) Immunoblot for total and phosphorylated (p) HSL (Ser660) in adipocytes from three different human subject samples cultured with (+) and without (−) SKOV3ip1 cells. (d) Immunofluorescence using confocal microscopy for p-HSL in SKOV3ip1 cells, adipocytes or a coculture of both. Arrowhead indicates an adipocyte (A) (nuclear counterstaining). One of two experiments, conducted using different human subject samples, is shown. (e) Immunoblot for total and p-AMPK in SKOV3ip1 cells cocultured with (+) and without (−) adipocytes for 24 h from three different human subject samples. (f) Immunofluorescence using confocal microscopy for p-AMPK (Thr172) in SKOV3ip1 cells, adipocytes, or a coculture of both. Arrow points out a cancer cell (C) in the image (nuclear counterstaining). One of two experiments, completed with different human subject samples, is shown. (g) β-oxidation rate in SKOV3ip1 cells cocultured with adipocytes (l-carnitine, positive control; etomoxir, negative control). Graph reports means at the indicated times±s.e.m. One of three experiments, conducted with or without different human subject samples, is shown. (h) mRNA expression of the rate-limiting fatty acid oxidation enzymes carnitine palmitoyltransferase 1 (CPT1a) and acyl-CoA oxidase 1 (ACOX1) in SKOV3ip1 cells cultured alone or with adipocytes. Bars report mean fold change relative to glyceraldehyde 3-phosphate dehydrogenase expression±s.e.m. One of three experiments, conducted with different human subject samples, is shown.

Adipocytes (Manabe et al., 2003; Tokuda et al., 2003, Dirat et al., 2011) and circulating lipids (Hardy et al. 2005) have been shown to promote growth of cancer cells. Further, direct transfer of lipids to cancer cells has also been reported (Gazi et al., 2007). Since adipocytes comprise a majority of the omentum and store triglycerides, fatty acids esterified to glycerol, the inventors contemplated that adipocytes provide energy-dense lipids to ovarian cancer cells to support rapid growth. Remarkably, in tissue from women with omental metastasis, the OvCa cells at the adipocyte/cancer cell interface contained abundant lipids (FIG. 5a and FIG. 6). Notably, coculture of either ovarian, breast, or colon cancer cells with adipocytes resulted in cytoplasmic lipid droplet accumulation in the cancer cells (FIG. 5b and FIG. 7a), which was confirmed by transmission electron microscopy (FIG. 5c). Coculture with omental or peritoneal adipocytes led to the greatest lipid accumulation in ovarian cancer cells as compared to cocultures with subcutaneous or bowel mesenteric adipocytes (FIG. 7b).

To determine whether the lipids detected in cancer cells after coculture were derived from adipocytes and not de novo lipogenesis, the inventors cultured cancer cells with adipocytes that had been load with fluorescently labeled lipids. During coculture, fluorescent lipids were transferred from adipocytes to SKOV3ip1 cells (FIG. 5d), supporting a model in which adipocytes provide lipids to support tumor growth. Consistent with these results, the coculture of three different ovarian cancer cell lines, including the recently established primary ovarian cancer cell line, MONTY-1 (Kaur, S. et al. 2009), with adipocytes led to a significant increase in cancer cell proliferation in vitro (FIG. 5e and FIG. 7c). In vivo, subcutaneous injection of SKOV3ip1 cells with primary human omental adipocytes into the flanks of nude mice produced tumors that were, on average, three times larger than tumors produced by SKOV3ip1 cells alone (Elliott, B. E et al. 1992) (FIG. 5l).

Figure 5:
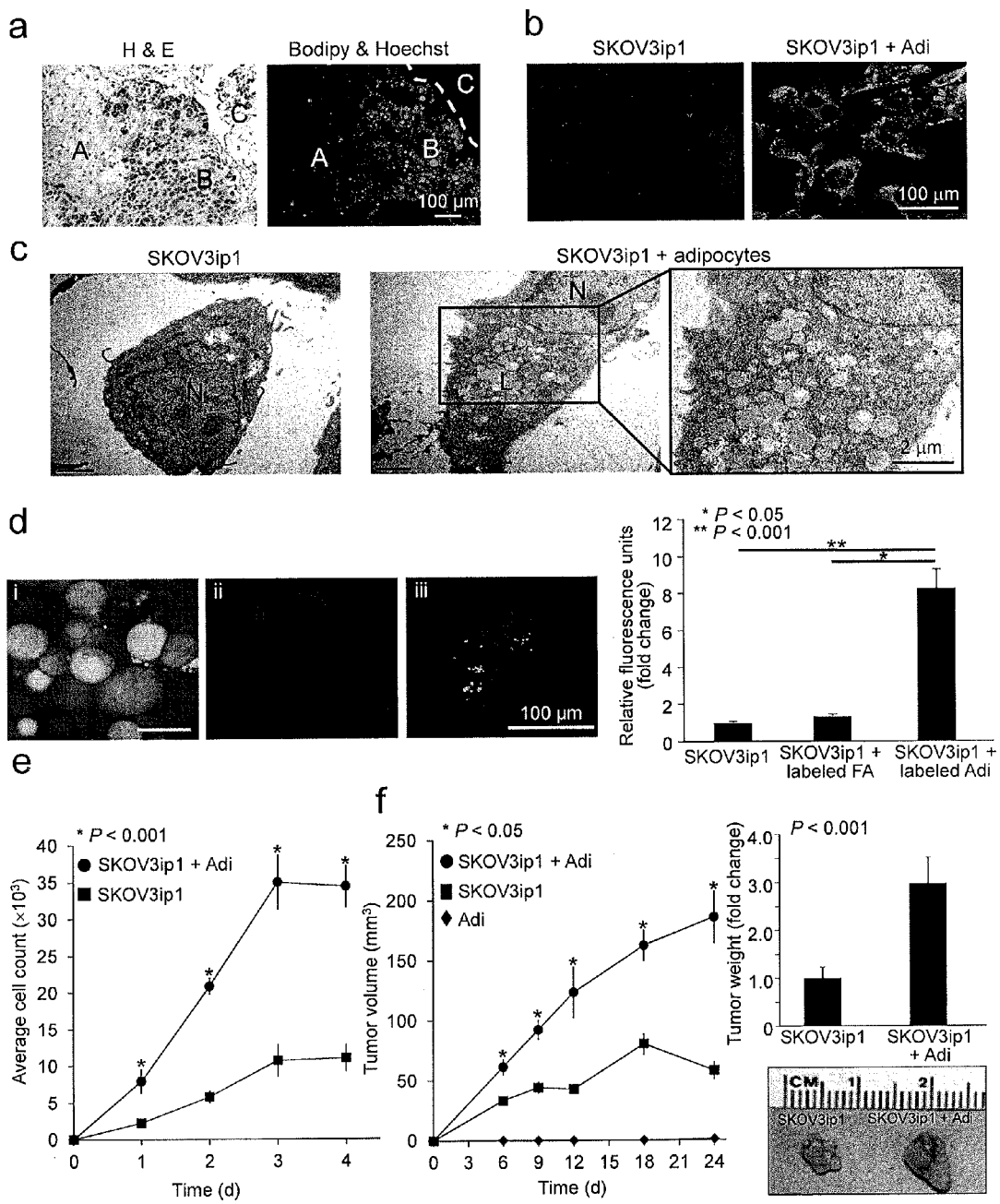
FIGS. 5a-5f Ovarian cancer cells use adipocyte-derived lipids for tumor growth. (a) Lipid accumulation in human omental metastatic ovarian cancer. The interface between ovarian cancer cells and adipocytes is indicated by a dashed line. Ovarian cancer cells (A) that do not interact with adipocytes (C) lack intracellular lipid staining. The ovarian cancer cells in contact with adipocytes (B) contain more intracellular lipids (nuclear counterstaining) (b,c) Lipid accumulation in SKOV3ip1 cells cultured alone or with primary human omental adipocytes (repeated with 2 additional human subject samples), as determined using confocal microscopy (b), or fixed and examined with transmission electron microscopy (c) (N, nucleus; L, lipid droplets). (d) Fluorescently labbled fatty acids (FAs) were incubated with and taken up by adipocytes (left) or SKOV3ip1 cells (middle). The labeled adipocytes were cocultured with SKOV3ip1 cells, the adipocytes were removed, and the labeled FAs that were transferred from adipocytes to SKOV3ip1 cells were detected wereby confocal microscopy (right). Fluorescence quantification is in the right graph. Bars report means±s.e.m from one of three experiments, conducted with different human subject samples. (e) In vitro proliferation of SKOV3ip1 cells alone or cocultured with adipocytes over 4 d. Graph reports means±s.e.m from one of three experiments, completed using different human subject samples (f) In vivo growth of subcutaneous tumors after injection of SKOV3ip1 cells with or without adipocytes in each flank of the same mouse. Graphs depict tumor volume measured over 24 d (left), and final tumor weight (right). Representative tumor images from one mouse are included (three or four mice per group). Graphs report means±s.e.m from one of three experiments, conducted using omental adipocytes from different human subject samples.
Figure 8:
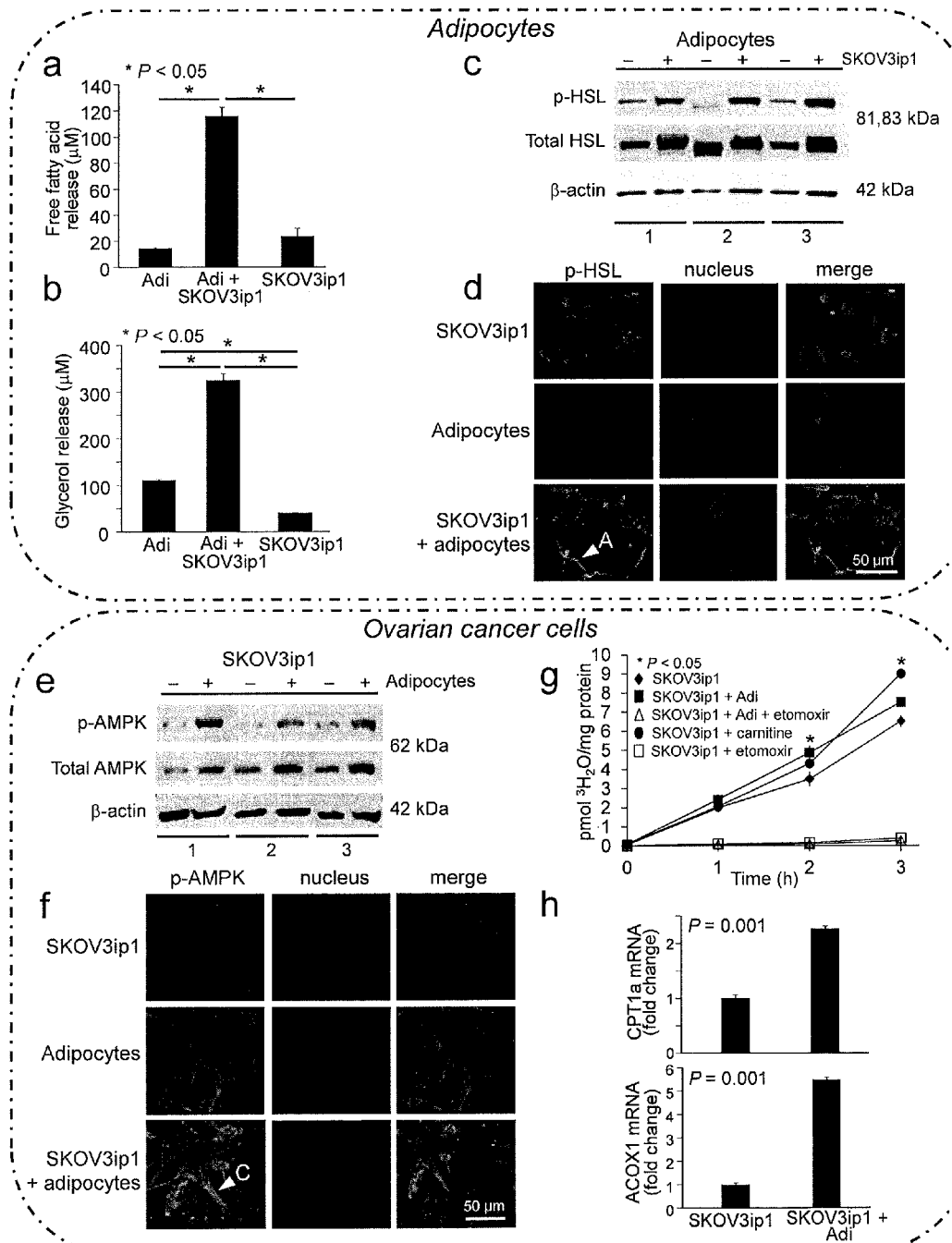
Figure 9:
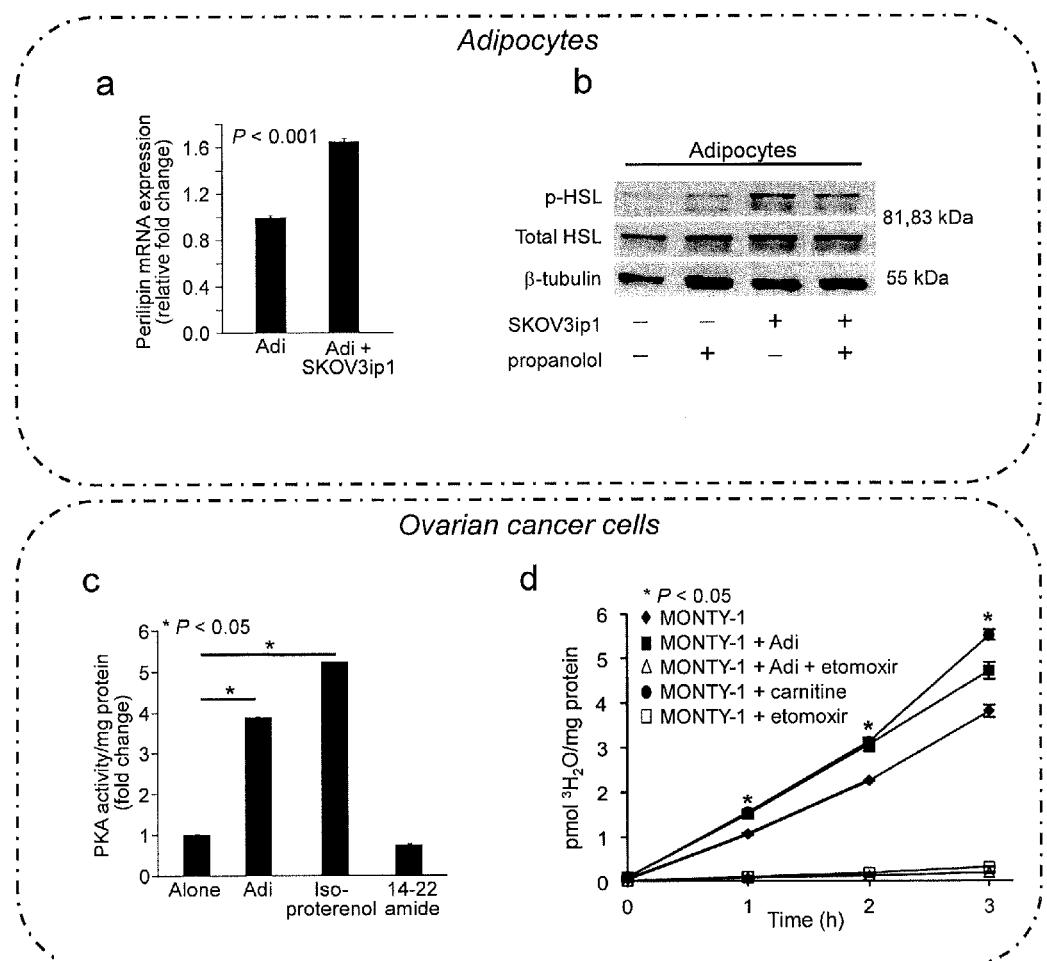
FIGS. 9a-9d Cocultivation of ovarian cancer cells with adipocytes activates lipolysis in adipocytes and β-oxidation in cancer cells. (a) Quantitative RT-PCR for perilipin 1 in primary human omental adipocytes (Adi) cultured with and without SKOV3ip1 ovarian cancer (OvCa) cells. Bars report mean fold change relative to glyceraldehyde 3-phosphate dehydrogenase expression±s.e.m. (b) Immunoblot for phosphorylated hormone sensitive lipase (p-HSL) and total HSL in SKOV3ip1 cells cocultured with (+) and without (−) adipocytes and pretreated with 10 μM propranolol, a β-adrenergic receptor antagonist. (c) SKOV3ip1 cells were cocultured (1 h) with adipocytes, treated with isoproterenol (positive control) or 14-22 amide (negative control) and protein kinase A (PKA) activity was assessed. (d) β-oxidation in MONTY-1 OvCa cells cocultured with primary human adipocytes (L-carnitine, positive control; etomoxir, negative control). The graph reports the average oxidation rate at the indicated times±s.e.m.

The results have indicated that adipocytes provide a proliferative advantage and transfer fatty acids to ovarian cancer cells (FIG. 5). Thus, the inventors hypothesized that metabolic alterations resulted from the interaction between adipocytes and ovarian ancer cells could explain this effect. The interaction between adipose tissue and contracting muscle exemplifies an analogous physiological model for the interaction between ovarian cancer cells and adipocytes. The energy for contracting muscle is provided by fatty acids mobilized from adipocytes (Wakil and Abu-Elheiga, 2009). The transport of free fatty acids depends on the lipolysis of stored triglycerides to free fatty acids and glycerol. Lipolytic activation in adipocytes commonly results from β-adrenergic receptor stimulation (Gonzalez-Yanes et al. 2006) which elicits a G-protein-coupled cascade and ultimately phosphorylation of hormone-sensitive lipase (HSL) and perilipin A, the rate-limiting enzymes in triglyceride hydrolysis (Sengenes et al., 2003) and the lipid droplet gate-keeper (Brasaemle et al., 2009), respectively. To understand the effect ovarian cancer cells have on adipocytes, adipocyte metabolism was assessed. In the presence of ovarian cancer cells, adipocytes released significantly more free fatty acids and glycerol (Gagnon et al., 2010) as compared to adipocytes cultured alone (FIGS. 8a,b). Perilipin mRNA levels (FIG. 9a) and HSL phosphorylation (FIGS. 8c,d) were also induced in primary human omental adipocytes. Furthermore, propranolol, the β-adrenergic receptor antagonist, partially reversed ovarian cancer cell-induced HSL activation (FIG. 9b). Taken together, these findings suggest cancer cells induce adipocyte lipolysis.

The metabolic alterations in ovarian cancer cells after coculture with adipocytes were evaluated. AMP-activated protein kinase (AMPK) is a central metabolic sensor that, upon phosphorylation, favors energy producing processes by inhibiting lipogenesis and activating fatty acid β-oxidation (Wang and Guan, 2010). This metabolic switch is regulated by the phosphorylation of acetyl-CoA carboxylase (ACC). Phosphorylation of ACC by AMPK or, to a lesser extent, protein kinase A (Munday, M. R. 1988) results in its inactivation and inability to inhibit carnitine palmitoyltransferase 1 (CPT1). CPT1 is the rate-limiting enzyme regulating mitochondrial import of fatty acids for β-oxidation in the form of acyl-CoA. Coculture of SKOV3ip1 cells with human omental adipocytes increased the phosphorylation of AMPK (FIGS. 8e,f), the activity of protein kinase A (FIG. 9c) and the rate of β-oxidation (FIG. 8g and FIG. 9d) in ovarian cancer cells. This induction of β-oxidation was paralleled by an increase in mRNA levels of CPT1 and acyl-CoA oxidase 1, the first enzyme in the β-oxidation pathway (FIG. 8h). These data suggest modifications in metabolism allow ovarian cancer cells to thrive on lipids acquired from adipocytes.

To understand molecular differences induced by omental adipocytes, primary ovarian cancer tissue and omental metastatic tissue from 22 women with advanced serous carcinoma were compared by using a reverse-phase protein array (Carey et al., 2010). When the expression or phosphorylation of 131 proteins were quantified, seven of the ten most upregulated or activated proteins in the omental metastases (FIG. 10a) were known regulators of cancer cell growth (retinoblastoma protein, mammalian target of rapamycin and signal transducer and activator of transcription 5) and metabolism (phosphoinositide 3-kinase, total and phosphorylatedACC, and FABP4). β-oxidation is often accompanied by an inhibition of de novo lipid biosynthesis, which is regulated by the phosphorylation of ACC. When ACC is phosphorylated by AMPK or PKA (Munday et al., 1988) it is inactive and no longer inhibits CPT-1, allowing the CPT-1-mediated mitochondrial import of fatty acids in the form of acyl-CoA for β-oxidation. The array showed that total and phosphorylated ACC amounts were significantly higher in omental metastases as compared to the primary tumor, which is consistent with inhibition of lipogenesis in a lipid-rich omental environment (FIG. 10a-c).

Figure 10:
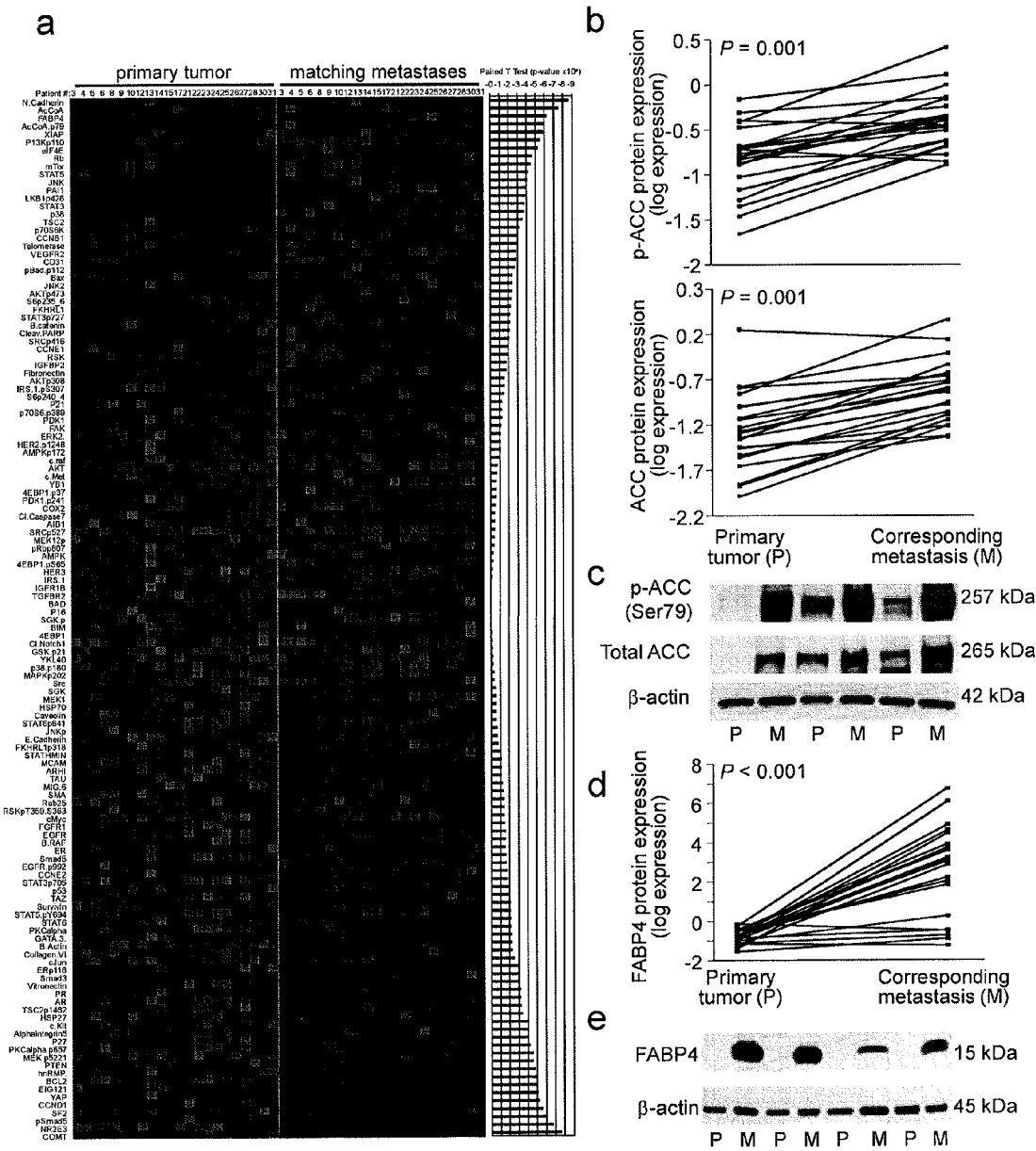
FIGS. 10a-10e Comparison of protein expression in human primary ovarian tumors and corresponding omental metastases. (a) Reverse phase protein array heat map. Primary ovarian tumor and the corresponding omental metastatic tissues were collected from a uniform cohort of 22 postmenopausal patients with advanced high-grade serous-papillary ovarian carcinoma (FIGO stage IIIC-IV). (b, d) Graphic representation of protein expression for individual patients included in the array for phosphorylated acetyl CoA carboxylase (p-ACC), total ACC (b), and fatty acid binding protein 4 (FABP4) (d). (c, e) Confirmation of the protein array data using immunoblots for p-ACC, total ACC (c), and FABP4 (e) using fresh tumor samples from primary ovarian tumor (P) and corresponding omental metastatic tissues (M).
Figure 11:
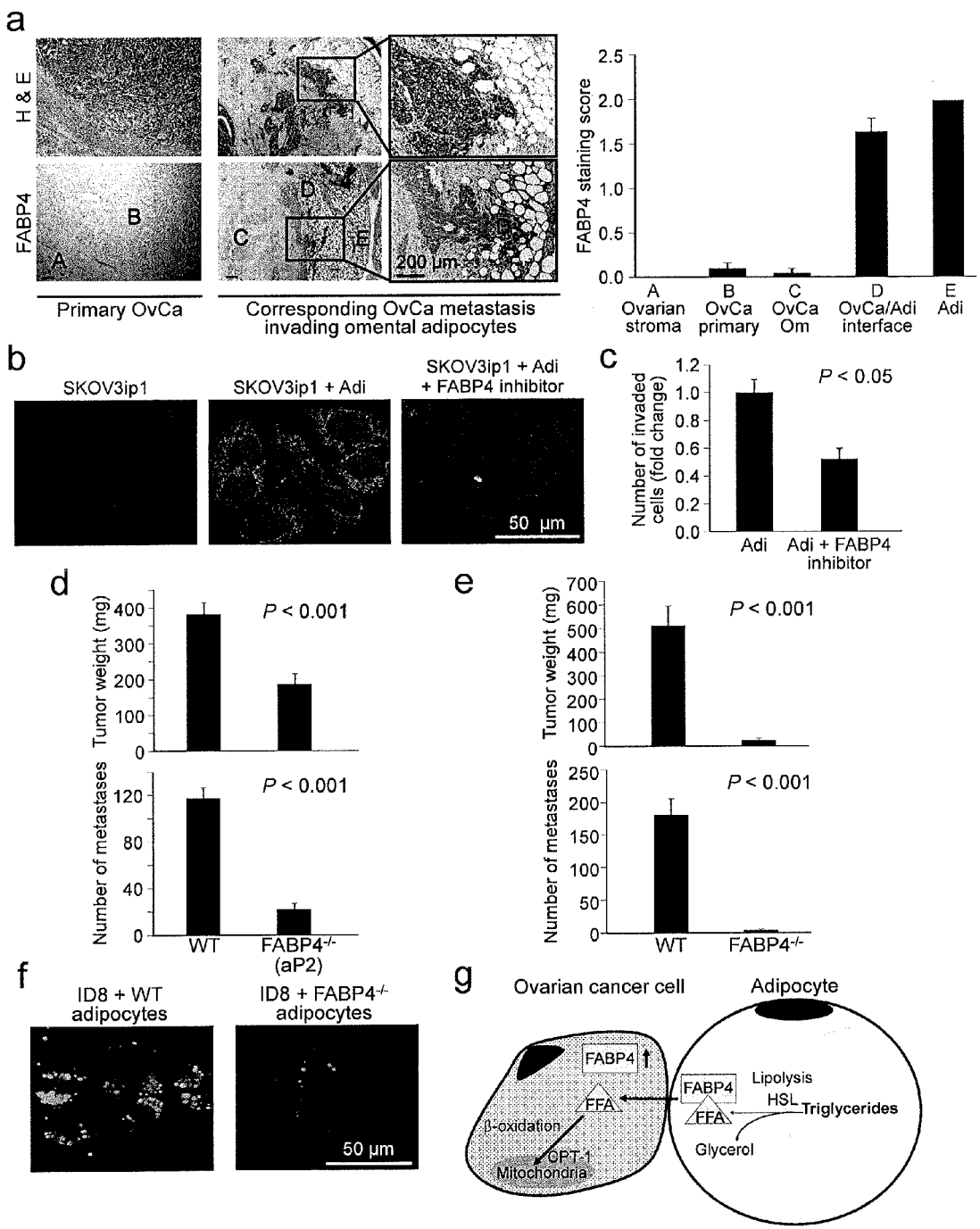
FIGS. 11a-11g FABP4 has a key role in the interaction of cancer cells with adipocytes. (a) Representative immunohistochemical staining (bottom) for FABP4 in serial sections of primary ovarian tumor and corresponding omental metastatic tissues from a subject with stage IIIC advanced serous ovarian cancer (as classified by the International Federation of Gynecology and Obstetrics). Hematoxylin and eosin (H & E) staining is in the top images. The graph on the right is a summary of FABP4 protein expression scoring in 20 subjects, as assessed by immunohistochemistry. The scoring (0, 1 or 2, corresponding to negative, weak or strong) was performed in different tissue compartments: Benign ovarian stroma (A), primary ovarian cancer in the ovary (B), ovarian cancer metastatic to the omentum (C), interface of ovarian cancer cells into adipocytes (Adi) (D), and adipocytes (E). Error bars, ±s.e.m. (b) Confocal microscopy images of lipid accumulation in SKOV3ip1 cells cocultured with or without primary human omental adipocytes and a FABP4 inhibitor (nuclear counterstaining). One of two experiments, conducted with different human subject samples, is shown. (c) Invasion assay of SKOV3ip1 cells toward adipocytes in the absence or presence of the FABP4 inhibitor HTS01037. Bars report mean fold change±s.e.m. One of two experiments, using two different human subject samples, is shown. (d) Metastatic tumor burden in FABP4 knockout mice ($ap\overline{2}^{-/-}$, denoted as FABP $\overline{4}^{-/-}$, n=23) or WT (n=28) mice 10 weeks post intraperitoneal injection of ID8 mouse ovarian cancer cells ($5\times10^6$). Bars report means±s.e.m. (e) Metastatic tumor burden in FABP $\overline{4}^{-/-}$ (n=6) or WT (n=7) mice 90 d after orthotopic injection of ID8 cells under the ovarian bursa. Bars report means±s.e.m. (f) Images generated by confocal microscopy of intracellular lipid accumulation (green) in ID8 cells cocultured with visceral adipocytes extracted from FABP$\overline{4}^{-/-}$ or WT mouse adipose tissue (nuclear counterstaining). (g) Summary of metabolic changes that occur in interacting ovarian cancer cells and adipocytes as described in the text FIGS. 12a-12d Characterization of fatty acid binding protein 4 expression in cocultures and human tissue. (a) Quantitative RT-PCR for fatty acid binding protein 4 (FABP4) in ovarian (SKOV3ip1 and MONTY-1), colon (RKO), and breast cancer cells (MDA-MB-231 and T47D) cocultured with primary human omental adipocytes. Bars report mean fold change relative to glyceraldehyde 3-phosphate dehydrogenase expression (GAPDH)±s.e.m. (b,c) Immunohistochemical staining for FABP4 in human tissues from different organs (b) and in human adipose tissues from different anatomic locations (FABP4, top panel; hematoxylin and eosin (H & E), bottom panel; 100-400×) (c). Adipocytes and endothelial cells stain positive for FABP4. (d) FABP4 expression in adipocytes from distinct adipose tissue sites by immunoblotting.
Figure 18:
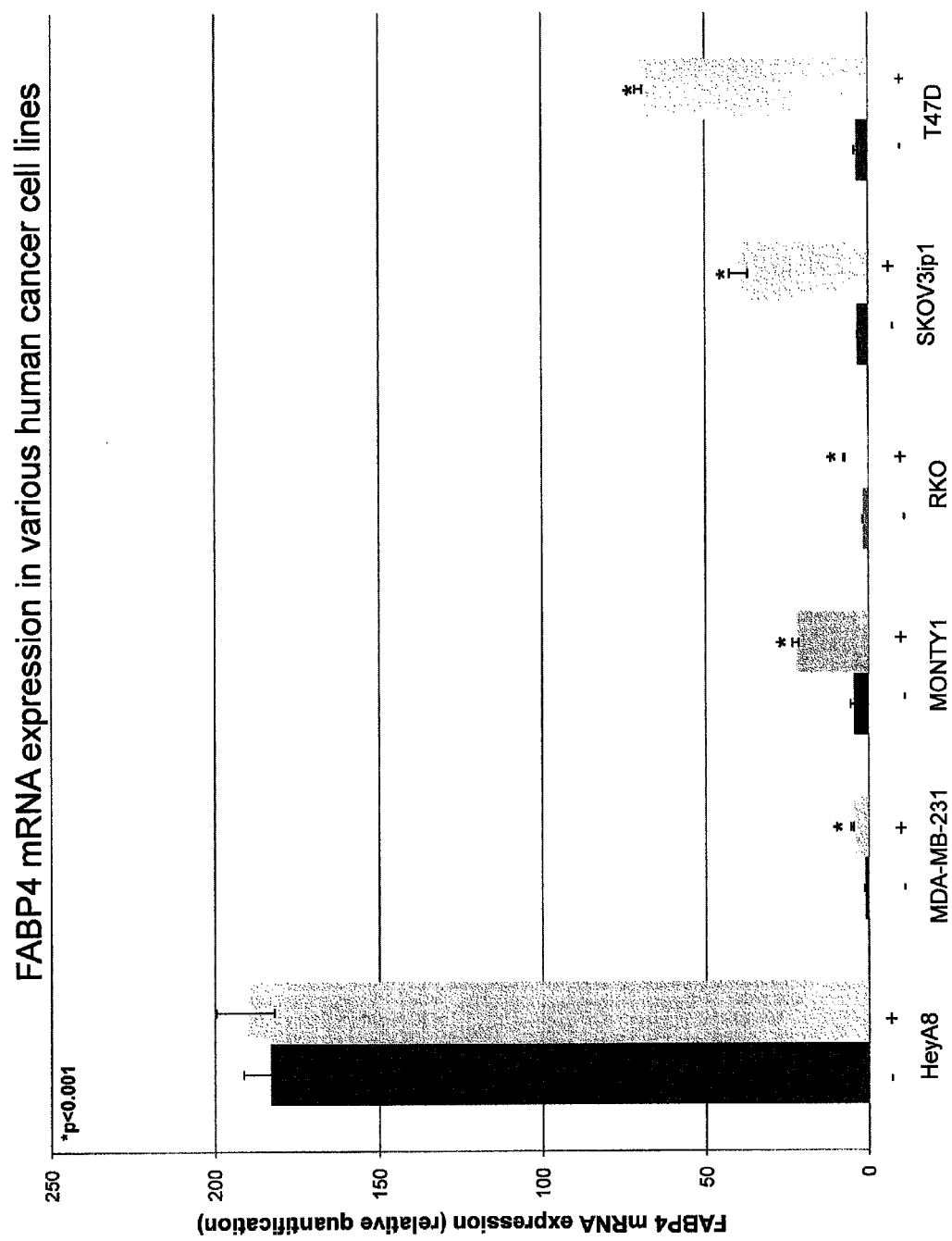
FIG. 18 Characterization of fatty acid binding protein 4 (FABP4) mRNA expression in cocultures. Quantitative RT-PCR for FABP4 in ovarian (HeyA8, SKOV3ip1 and MONTY-1), colon (RKO), and breast cancer cells (MDA-MB-231 and T47D) cocultured with primary human omental adipocytes. Bars report mean fold change relative to glyceraldehyde 3-phosphate dehydrogenase expression (GAPDH) ±s.e.m.
Figure 19:
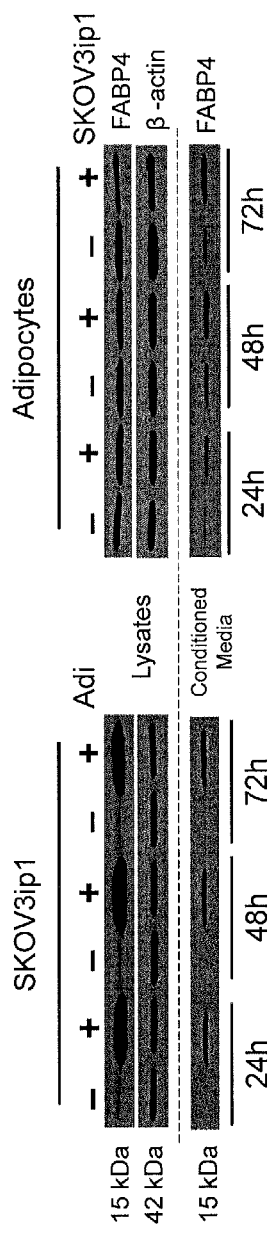
FIG. 19 Immunoblot for FABP4 protein in human ovarian cancer cells and human adipocytes (adi) co-culture. Human ovarian cancer cells (SKOV3ip1, HeyA8, OVCAR5) were cultured alone (−) or cocultured with human primary adipocytes (adi) (+) for 24-72 h. The cells were separated, conditioned medium were collected and proteins were harvested for immunoblot analysis of FABP4 expression.
Figure 19:
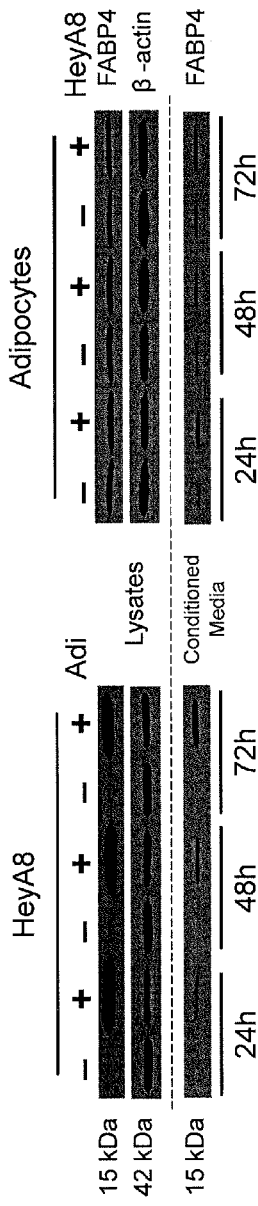
Figure 19:
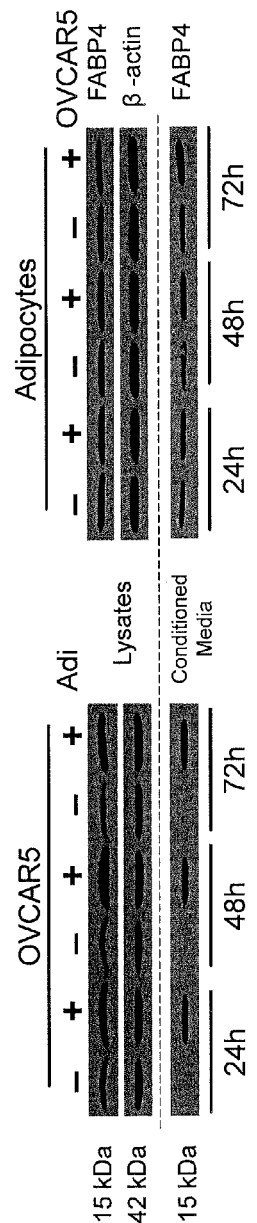

The protein with the third largest change in expression between the primary tumor and its metastases was FABP4. FABP4 reversibly binds long-chain fatty acids and is highly expressed by adipocytes (Hotamisligil et al., 1996; Furuhashi and Hotamisligil, 2008). In primary ovarian tumors, FABP4 expression was low, however, in all omental metastases, an upregulation of FABP4 expression was shown, which we validated by immunoblotting (FIG. 10 *a,d,e*). Immunoblotting for FABP4 in human ovarian cancer cells (SKOV3ip1, HeyA8, or OVCAR5 cells) cultured alone or cocultured with human primary adipocytes indicated that upon cocaluturing with adipocytes, FABP4 was present in the conditional media and its expression in ovarian cancer cells increased (FIG. 19). Immunohistochemical staining comparing primary ovarian tumor and corresponding omental metastatic tissues in twenty additional pairs revealed that FABP4 was strongly expressed in ovarian cancer cells at the adipocyte interface (FIG. 11a). In contrast, no FABP4 staining was detected in ovarian cancer cells distant from the adipocyte interface in omental metastatatic tissue, in tissue from the corresponding primary ovarian tumor or in the adjacent benign ovarian stroma (FIG. 11a). The upregulation of FABP4 in metastatic human ovarian cancer samples could be mimicked in vitro; cocultivation of SKOV3ip1 cells or HeyA8 cells with adipocytes induced FABP4 mRNA expression (FIGS. 17a-17d). Cocultivation of several cancer cell lines (ovarian, breast, and colon) with adipocytes induced FABP4 mRNA expression, suggesting this induction is not limited to ovarian cancer cells (FIG. 12a, FIG. 18).

Figure 12:
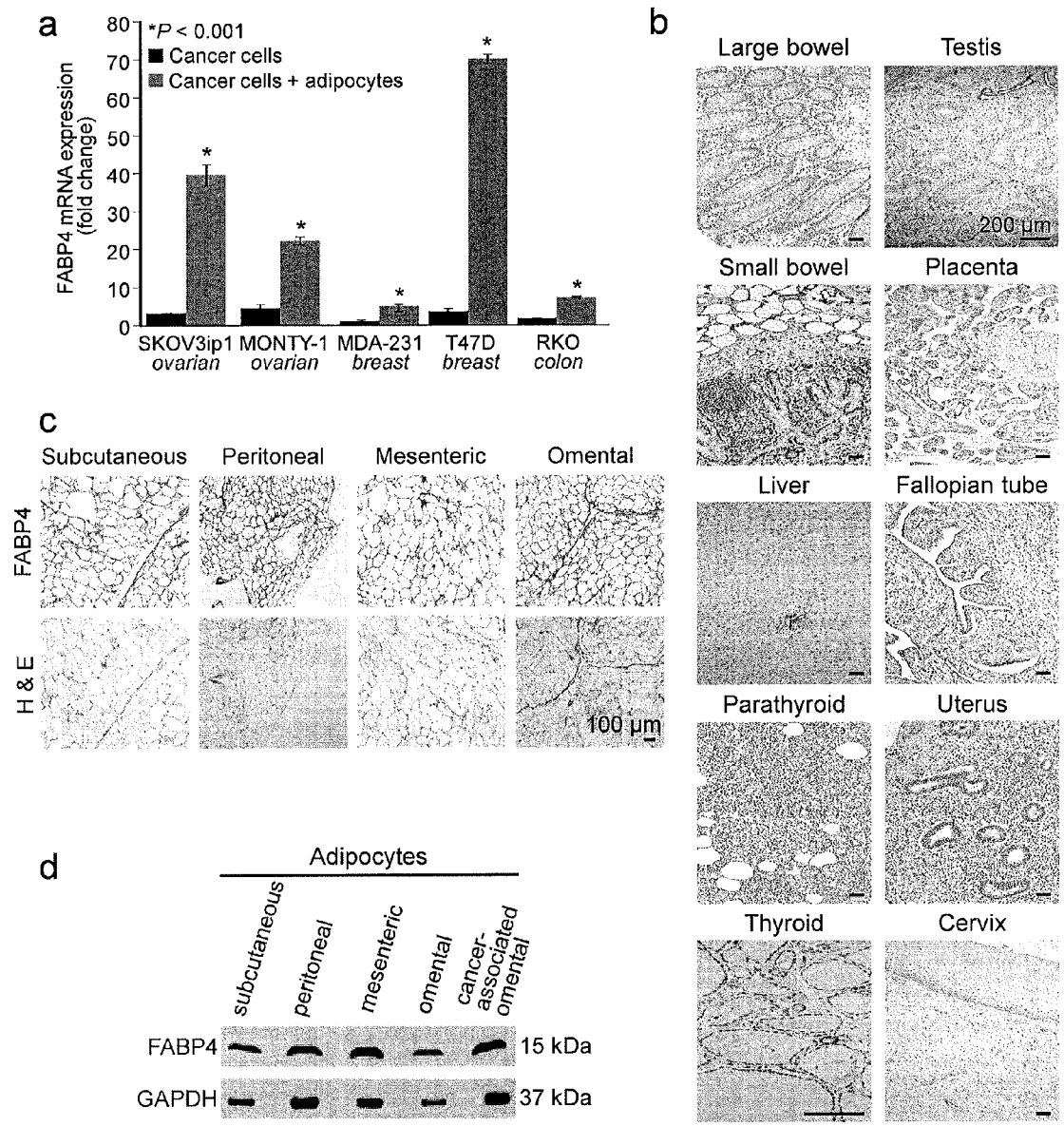
Figure 13:
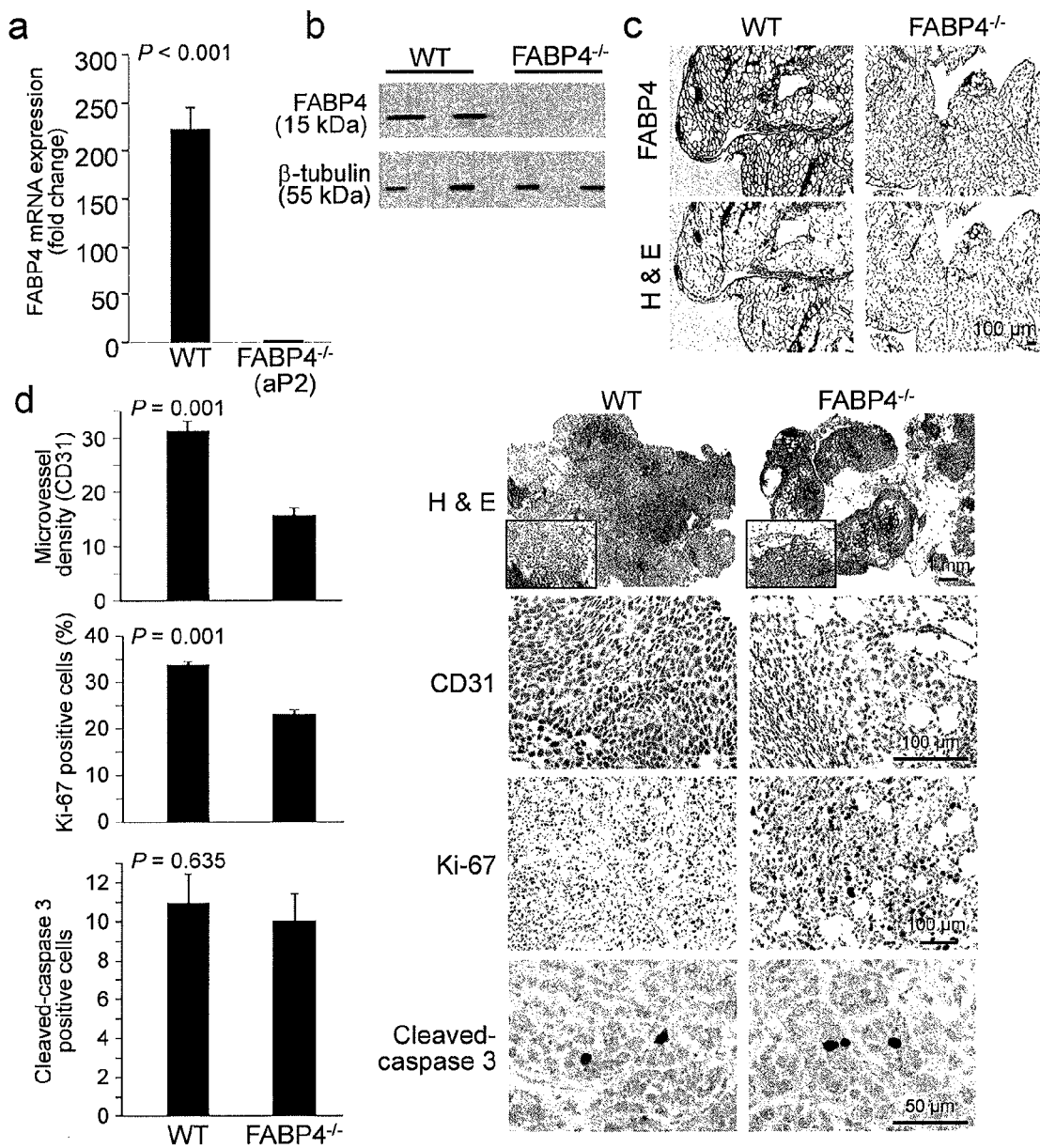
FIGS. 13a-13d Characterization of fatty acid binding protein 4 and tumor tissues from knockout and wild-type mice. (a,b) Fatty acid binding protein 4 (FABP4), aP2, expression in visceral adipocytes from FABP4 knockout (FABP4$^{-/-}$) and wild-type (WT) mice by quantitative RT-PCR (a) and immunoblotting (b). Bars report mean fold change relative to glyceraldehyde 3-phosphate dehydrogenase expression±s.e.m. (c) Immunohistochemical staining for FABP4 in omentum from FABP4$^{-/-}$ and WT mice (100×). (d) ID8 mouse ovarian cancer cells were injected intraperitoneally into FABP4$^{-/-}$ or WT mice. Immunohistochemical staining of intraomental tumor sections from WT and FABP4$^{-/-}$ mice for markers of proliferation (Ki-67), microvessel density (CD31), and apoptosis (cleaved-caspase 3). Staining quantification is on the left and representative images are on the right (hematoxylin and eosin (H & E), 20× and 200× insets; CD31, 200×; Ki-67, 100×; and cleaved-caspase 3, 400×). Bars report means (n=5-9 mice/group)±s.e.m.
Figure 14A:
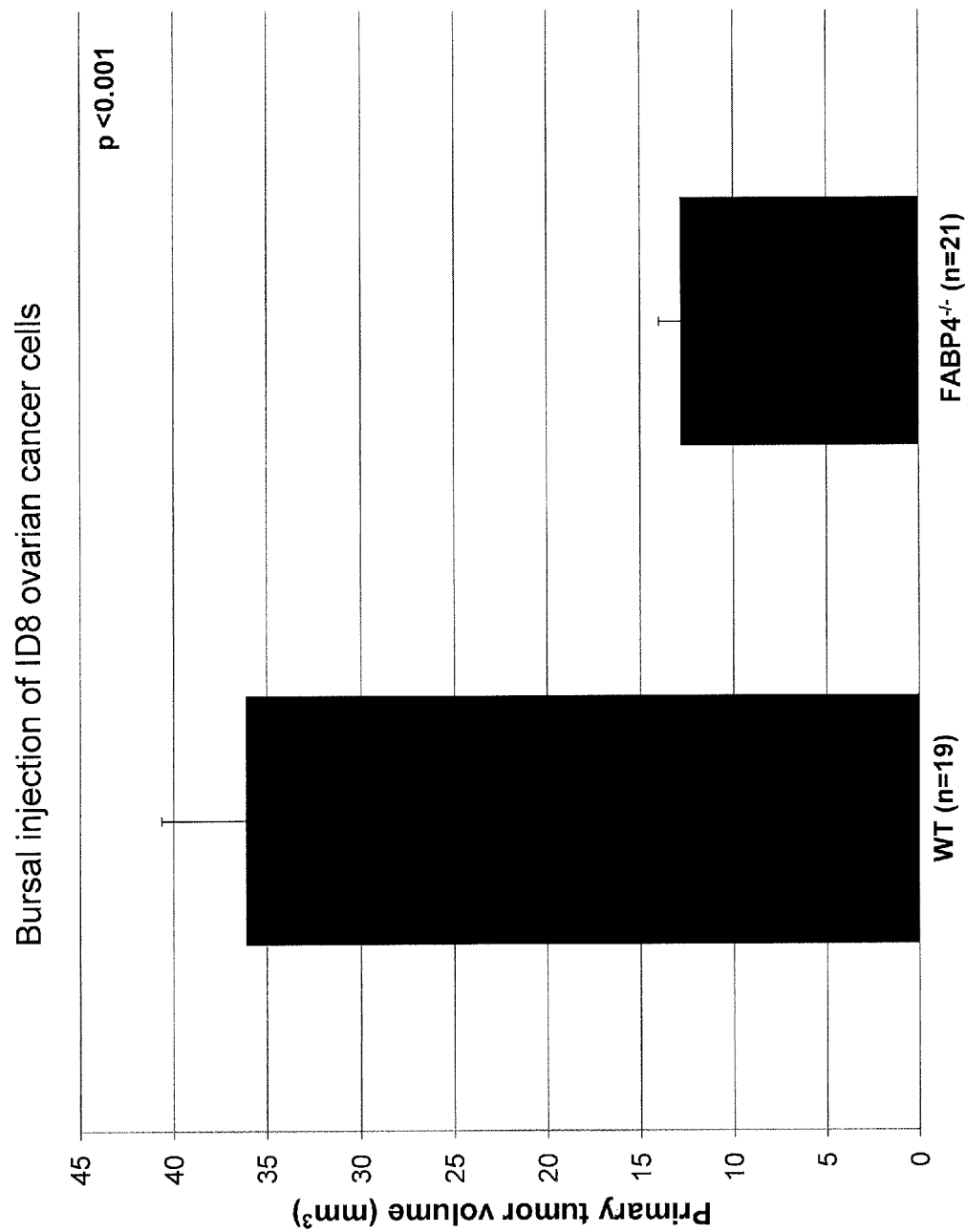
FIGS. 14a-14f Tumor burden in FABP4$^{-/-}$ (n=21) or WT (n=19) mice. A million ID8 mouse ovarian cancer cells were injected under the mice ovarian bursa. 90 days after injection, primary tumor volume (a), primary tumor weight (b), number of metastases (c), metastatic tumor weight (d), and ascites volume (e) were assessed. Bars report means±s.e.m. in (a)-(e). (f) shows the representative images of mice injected with ID 8 mouse ovarian cancer cells under the bursa of the right ovary (syngeneic orthotopic model). Inset is a H&E staining of the tumor sections removed from WT mice and FABP4$^{-/-}$ mice.
Figure 14B:
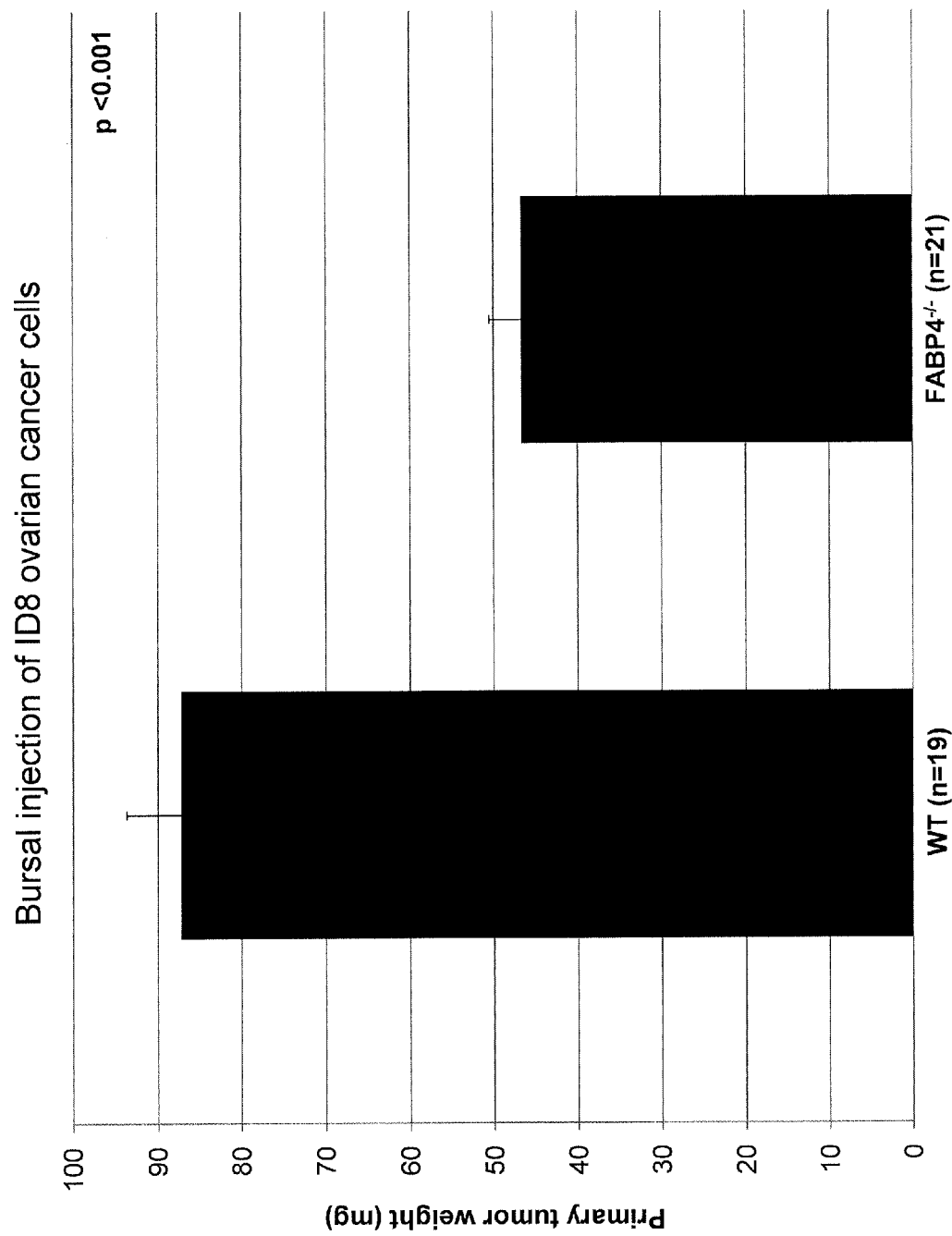
Figure 14C:
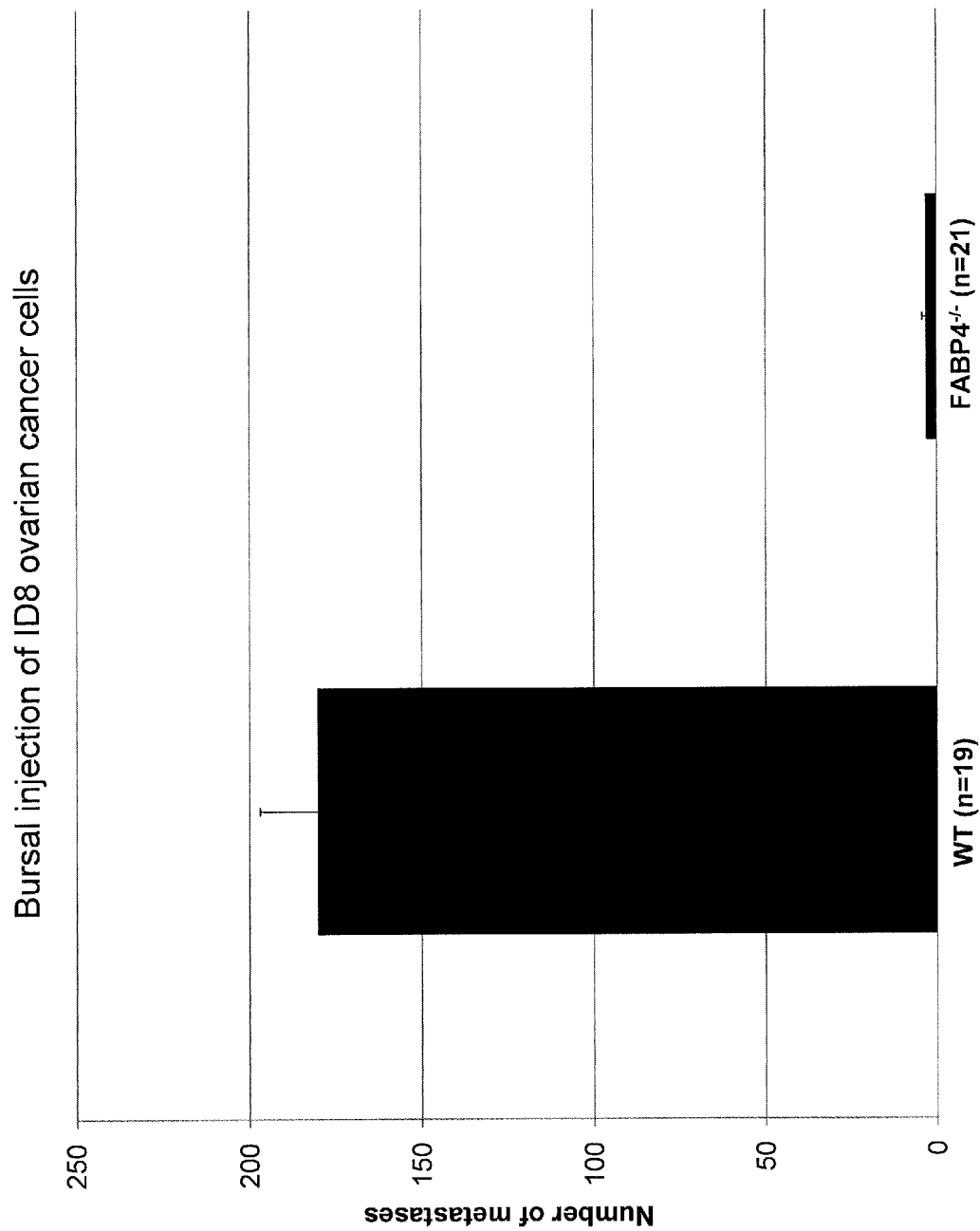
Figure 14D:
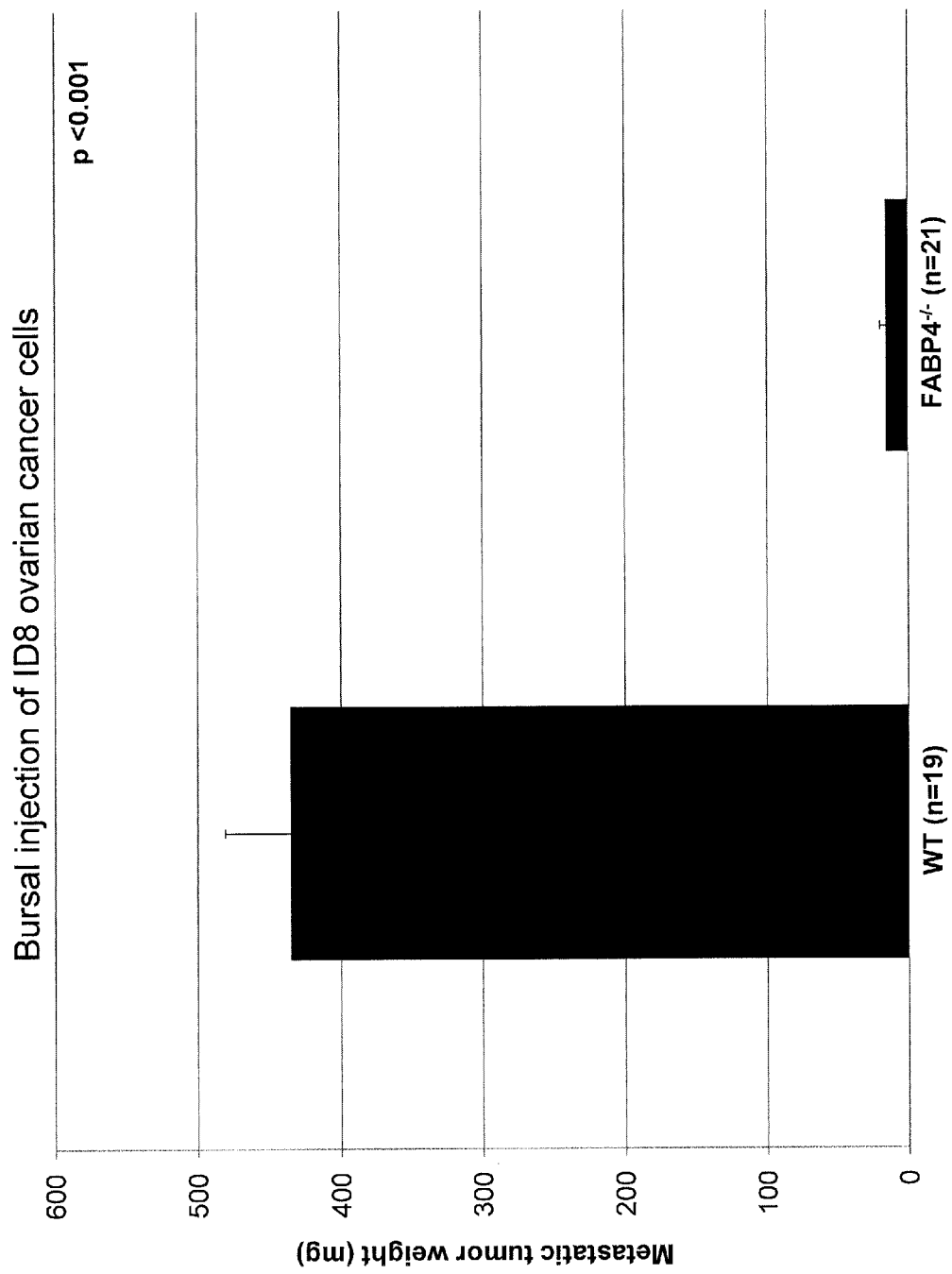
Figure 14E:
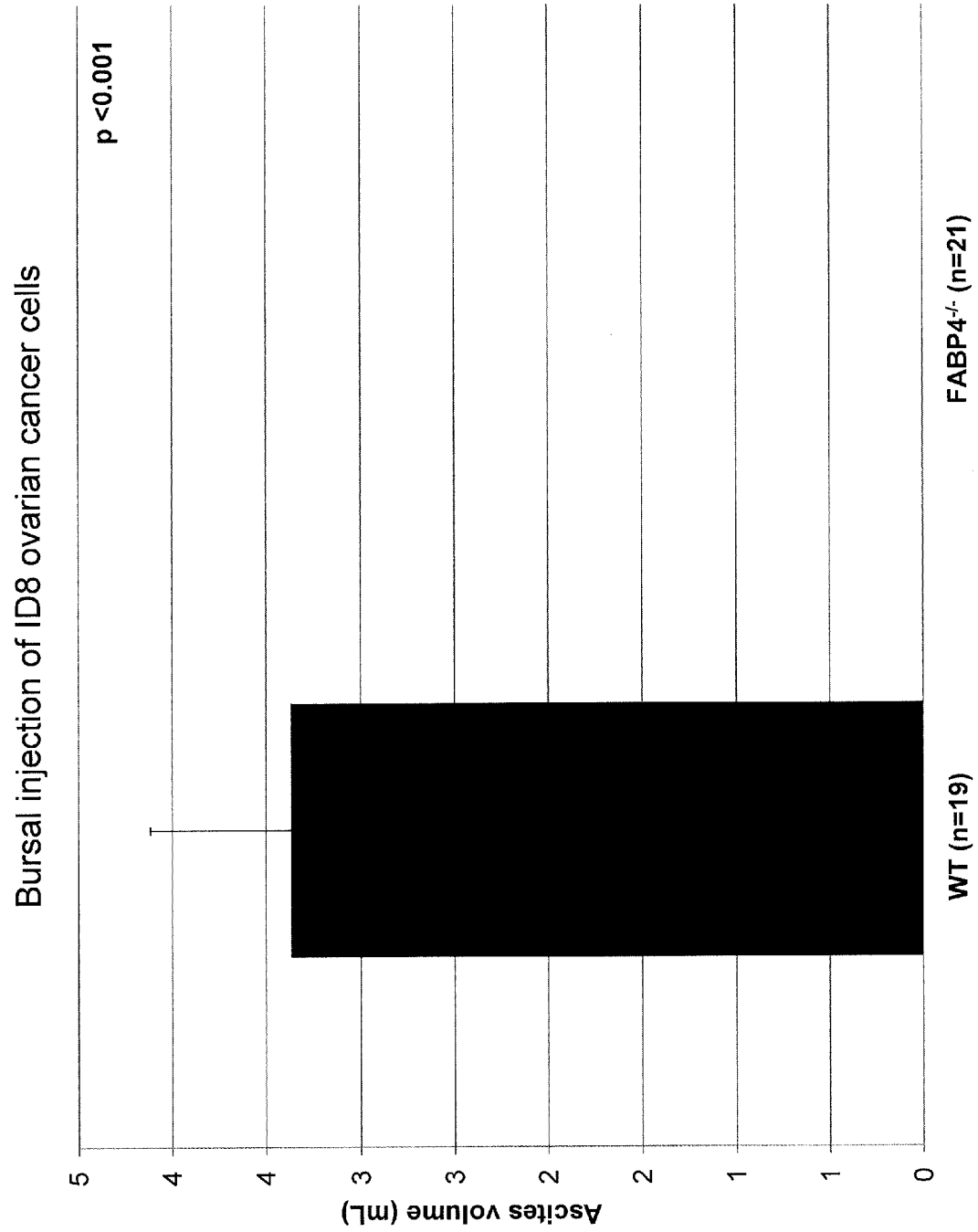
Figure 14F:
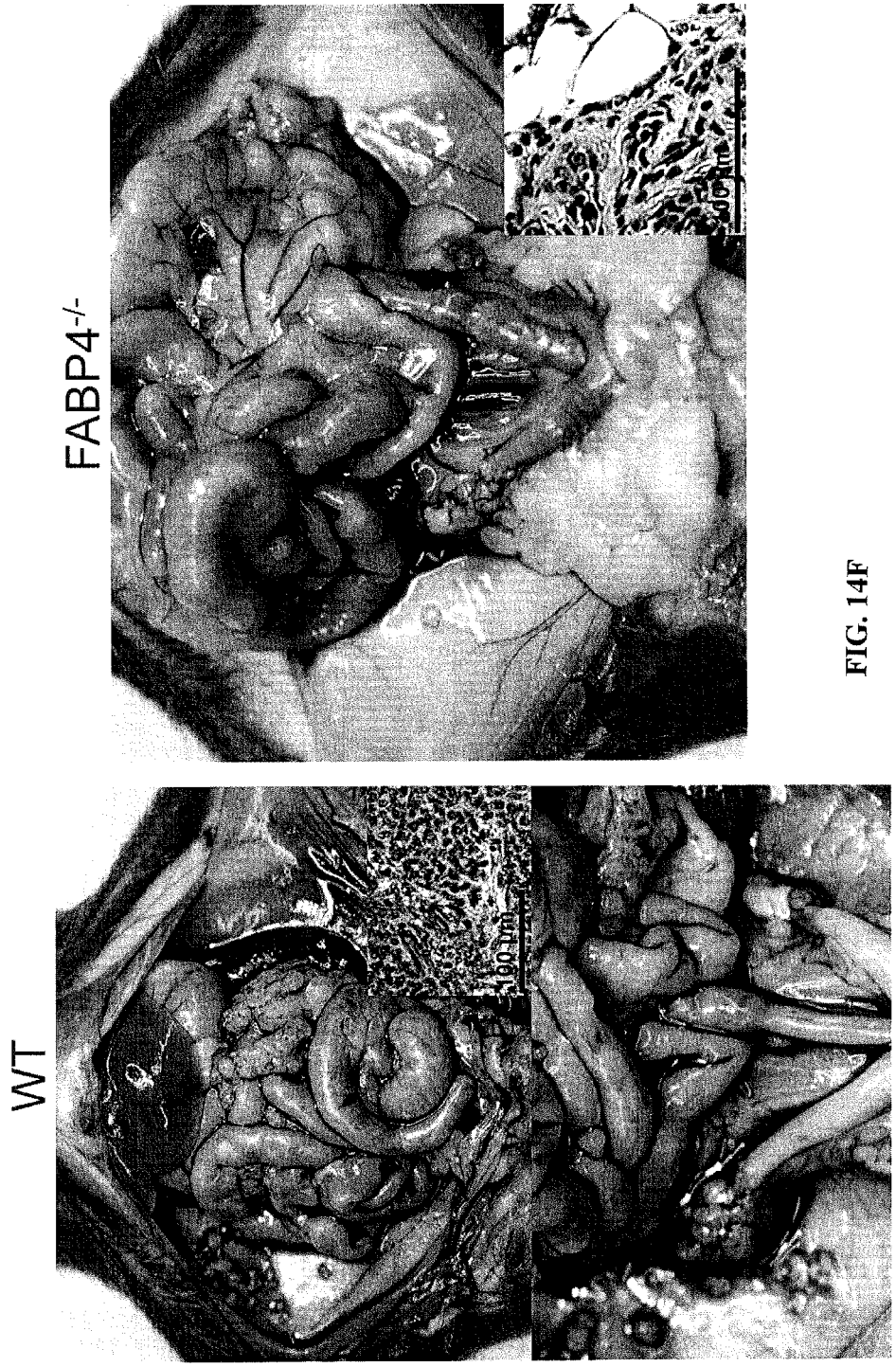
Figure 20:
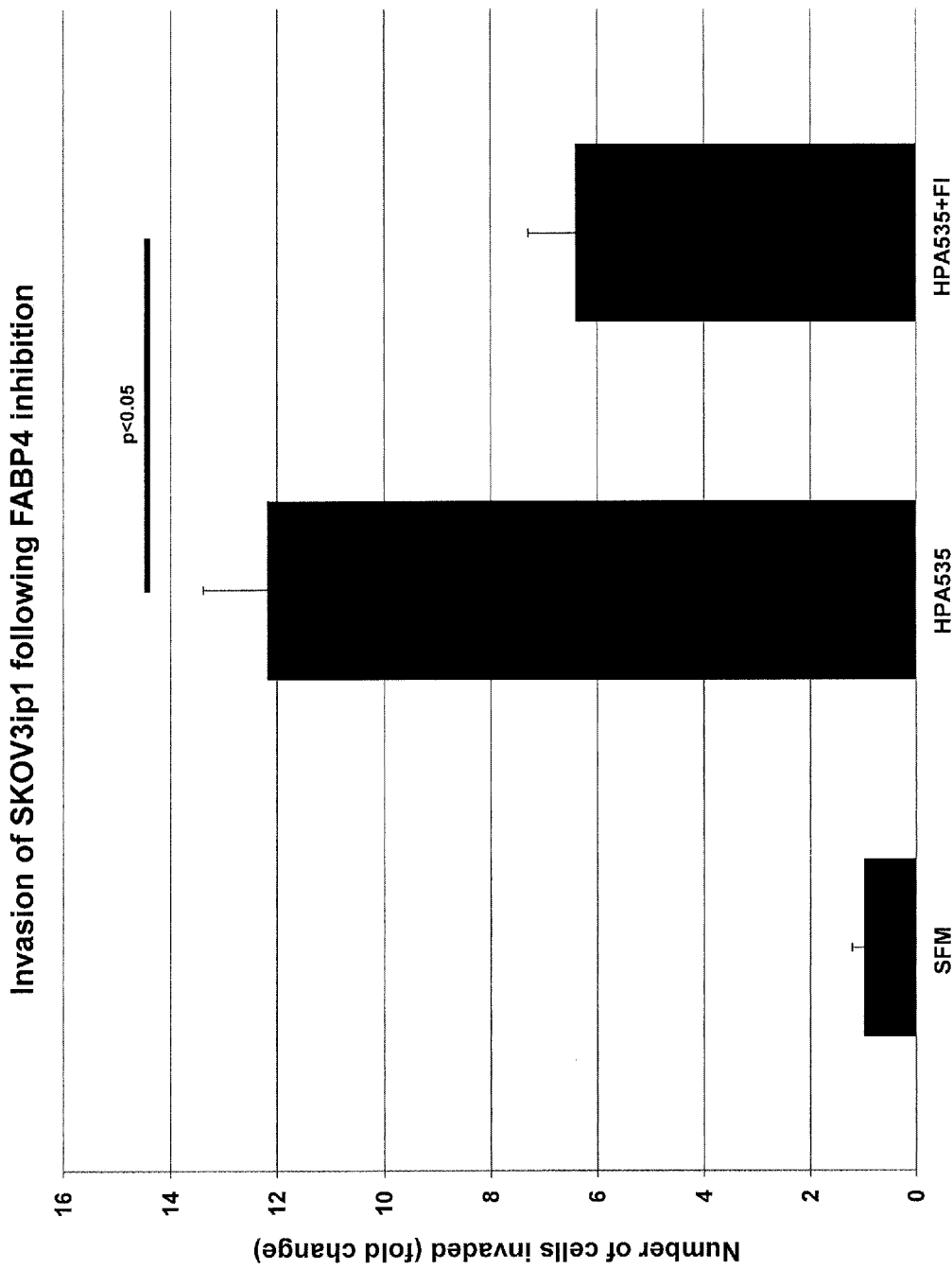
FIG. 20 Invasion of SKOV3ip1 following FABP4 inhibition. SKOV3ip1 incubated 24 h with Adipocytes HPA 535 or Adipocytes HPA535 pre-treated with the FABP4 inhibitor HTS01037 (FI) or serum free medium (SFM).

FABP4 staining of normal tissue from human organs showed FABP4 was expressed in endothelial cells and adipocytes from different anatomic locations (subcutaneous, peritoneal, mesenteric, omental and cancer-associated omental tissues) independent of the tissue origin (FIG. 12b-d). FABP4 has been shown to regulate lipolysis (Scheja, L. et al. 2007), and its actions can be blocked by small-molecule inhibitors (Furuhasi, M. et al. 2007). When a FABP4 inhibitor (Hertzel et al., 2009) was added to the coculture of ovarian cancer cells and adipocytes, lipid accumulation in the cancer cells (FIG. 11b) and adipocyte-mediated invasion (FIG. 11c, FIG. 20) was drastically reduced. However, using the inhibitor did not clarify whether FABP4 expression in adipocytes or cancer cells is important for its tumor-promoting functions. Therefore, ovarian cancer tumor growth in aP2-knockout (aP2$^{-/-}$, denoted as FABP4$^{-/-}$) mice was assessed. FABP4$^{-/-}$ mice have reduced insulin resistance following environmentally— (Hotamisligil et al., 1996) or genetically-induced (Uysal et al., 2000) obesity, however the effect of FABP4 deficiency on cancer growth or metastasis was undetermined. After confirming the absence or presence of FABP4 mRNA and protein expression in adipose tissue from FABP4$^{-/-}$ and wild-type (WT) mice (FIG. 13a-c), ID8 mouse ovarian cancer cells were injected either intraperitoneally or orthotopically under the ovarian bursa. In the intraperitoneal model, a significant reduction in tumor burden in the absence of FABP4 was observed (FIG. 11d). This was paralleled by a reduction in microvessel density (CD31) and tumor cell proliferation (Ki-67), with no change in caspase-3 activation in tumors from FABP4$^{-/-}$ mice (FIG. 13d), suggesting host FABP4 is important for tumor cell growth without affecting apoptosis. Notably, in the more relevant orthotopic model, very few metastases were detected in FABP4$^{-/-}$ mice (4±2 (FABP4$^{-/-}$) versus 181±25 (WT) metastatic nodules; FIG. 11e). Consistent with these findings, a substantial reduction in tumor burden, including primary tumor volume and weight, metastases number, metastatic tumor weight, and ascites volume in FABP4$^{-/-}$ deficient mice versus WT mice was observed (FIGS. 14a-14f).

Figure 15:
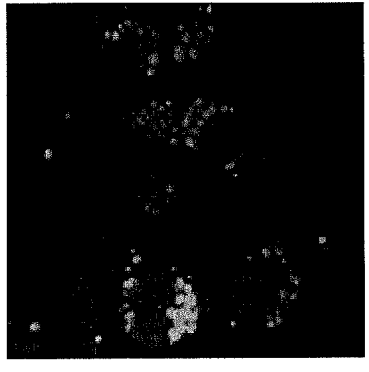
FIG. 15. FABP4 deficiency prevents lipid accumulation in mouse ovarian cancer cells. Top panel shows in vitro images generated by confocal microscopy of intracellular lipid accumulation in ID 8 cells cocultured with digested from mouse adipose tissue. ID 8 cells were cocultured with adipocytes digested from mouse adipose tissue. Adipocytes were washed away after 36 h and the cells were stained with Bodipy. Bottom panel shows in vivo images generated by confocal microscopy of frozen sections of ID8 tumors in FABP4$^{-/-}$ or WT mice, respectively.
Figure 15:
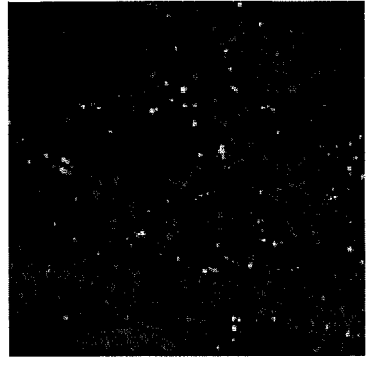

To directly test the role of FABP4 in the host adipocytes, ID8 cells were cultured with adipocytes from FABP4$^{-/-}$ and WT mice. Lipid content was reduced in ID8 cells cultured with FABP4$^{-/-}$ adipocytes as compared to those cultured with WT adipocytes (FIG. 11f). In vivo images of stained frozen sections of ID 8 tumors also demonstrated a reduction of lipid content in FABP4$^{-/-}$ mice in comparison with WT mice (FIG. 15). These data identify FABP4 as a key mediator of ovarian cancer cell-adipocyte interactions in the host and potentially the cancer cells, by increasing lipid availability and supporting metastasis (FIG. 11g).

Figure 16A:
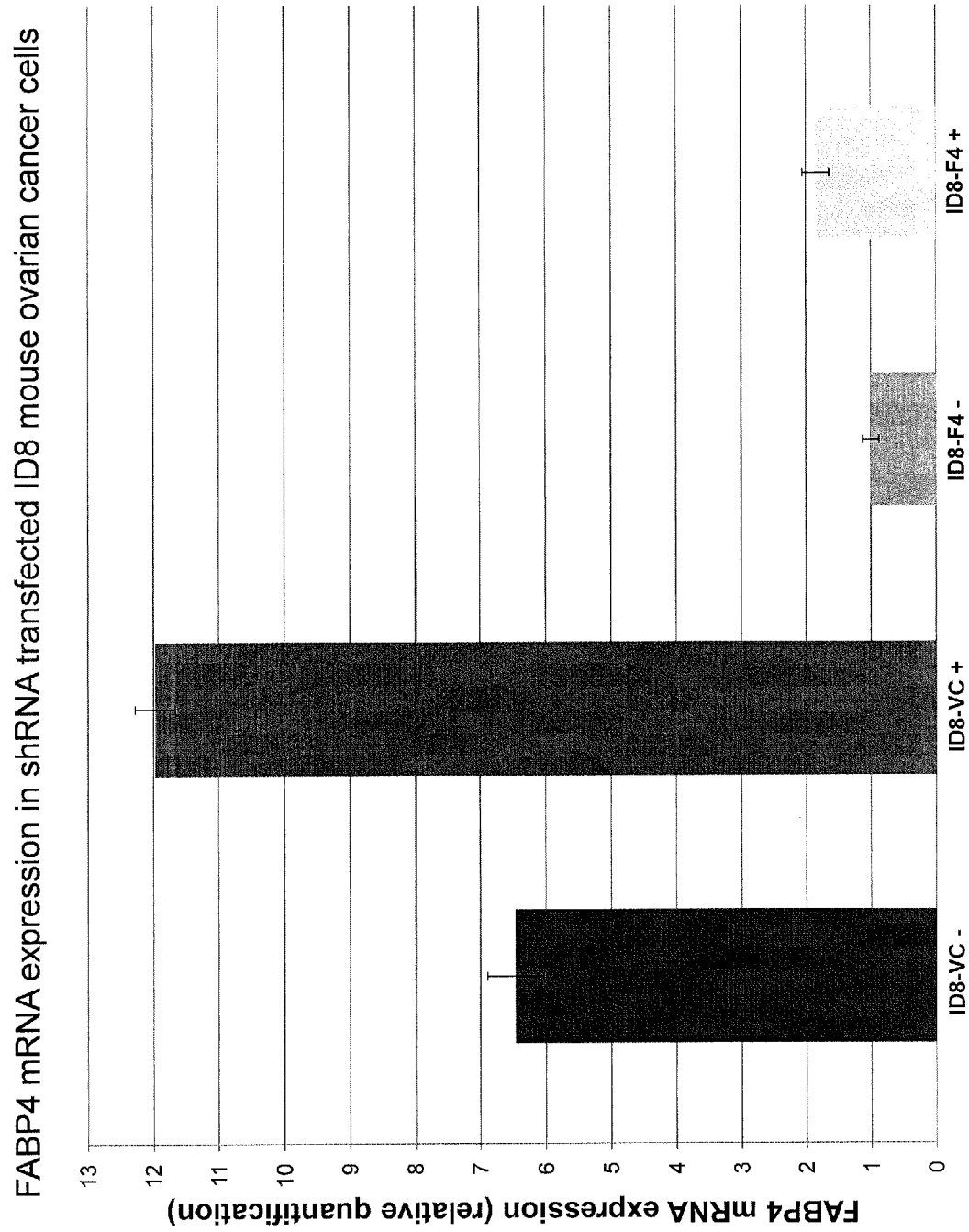
FIGS. 16a-16d Effects of FABP4 downregulation. (a) FABP4 mRNA expression in ID8 mouse ovarian cancer cells transfected with FABP4 small hairpin RNA (shRNA) (F4) or vector control shRNA (VC) in the presence (+) or absence (−) of mouse adipocytes. Bars report means±s.e.m. (b) Tumor burden in mice 10 weeks after intraperitoneal injection of ID8 mouse ovarian cancer cells transfected with 5 million shRNA (F4 or VC). (c) Metastatic tumor burden in mice 10 weeks after intraperitoneal injection of ID8 mouse ovarian cancer cells transfected with 5 million shRNA (F4 or VC). (d) mRNA expression of FABP4 in tumors collected 10 weeks after intraperitonel injection of ID 8 mouse ovarian cancer cells transferred with FABP4 shRNA or vector control shRNA. FABP4 mRNA expression was measured by quantitative RT-PCR.
Figure 16B:
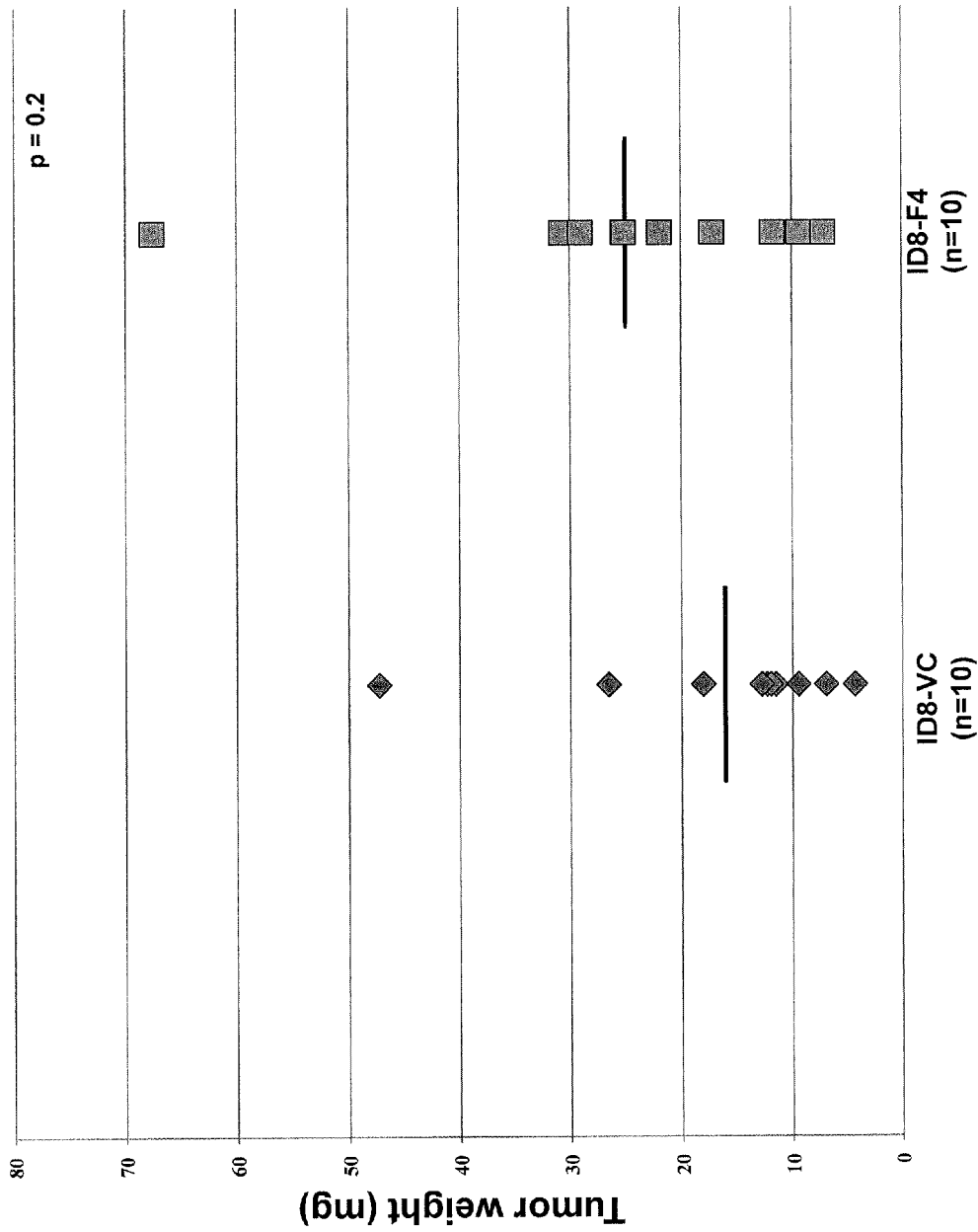
Figure 16C:
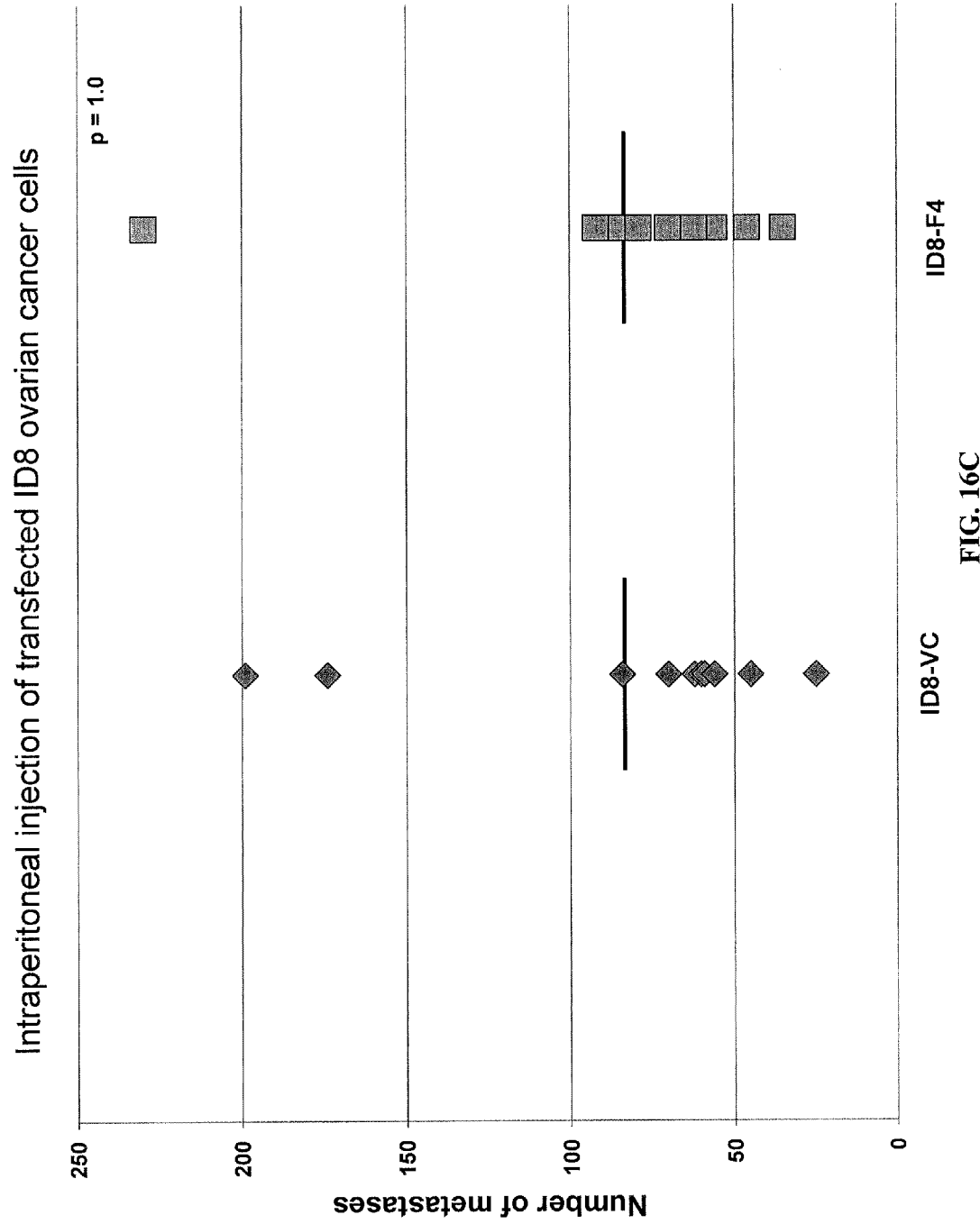
Figure 16D:
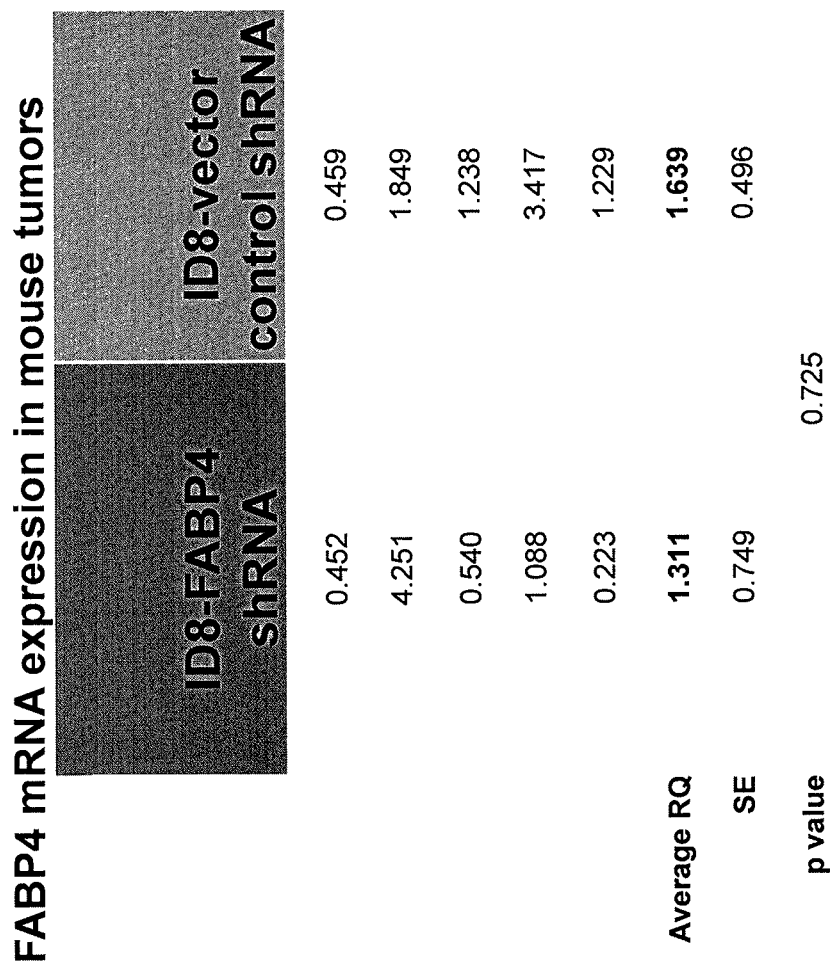
Figure 17A:
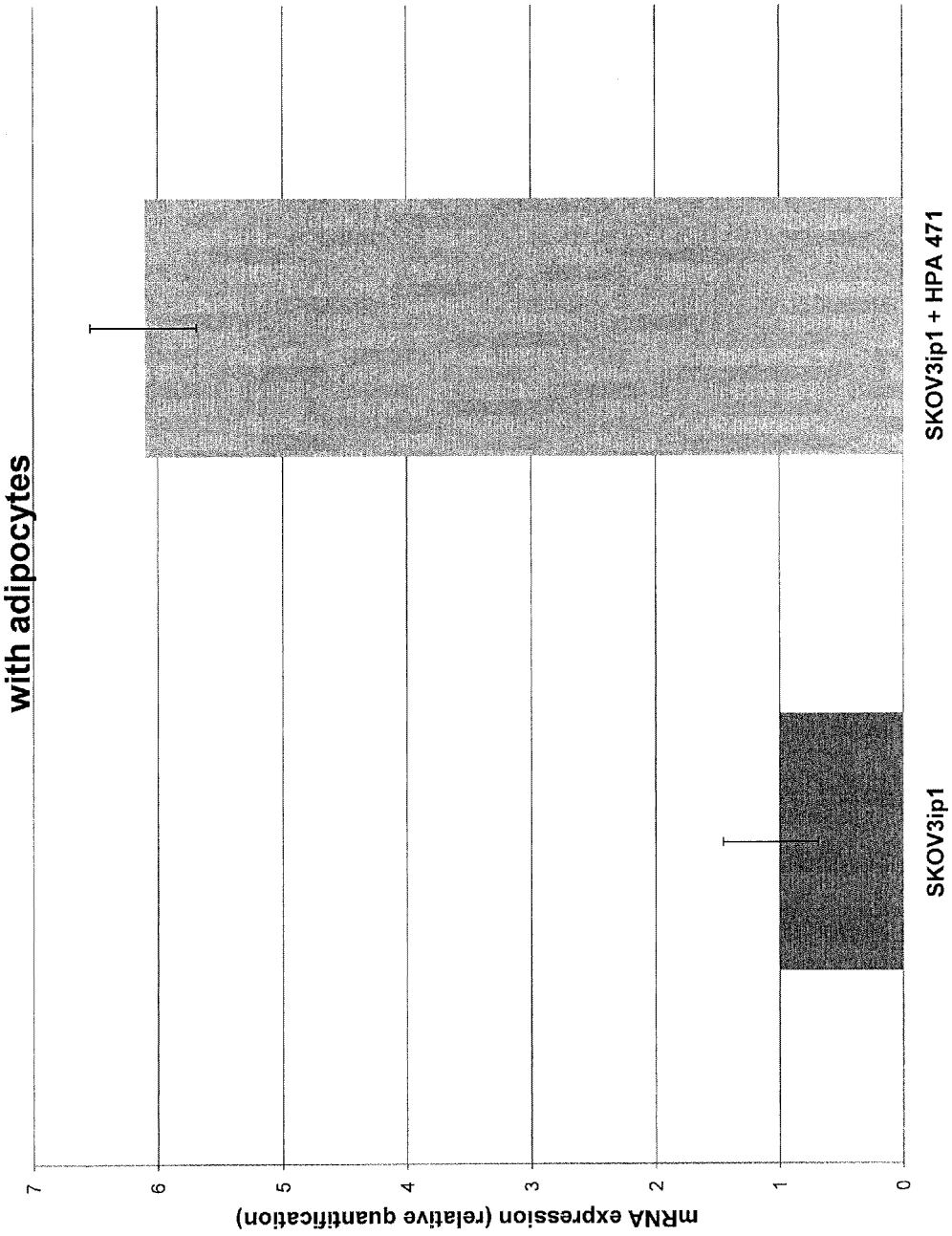
FIGS. 17a-17d Characterization of FABP4 expression in cocultures. (a) Quantitative RT-PCR for FABP4 mRNA expression in sorted SKOV3ip1 cells cocultured with adipocytes HPA 471 (1:5 in serum-free medium). These data are normalized to GAPDH. Prior to sorting, SKOV3ip1 cells were labeled in suspension with CMFDA (green). (b) Quantitative RT-PCR for FABP4 mRNA expression in unsorted SKOV3ip1 cells cocultured with adipocytes HPA 478 (1:5 in serum-free medium) and collected 24 h after washing and spinning to remove adipocytes. These data are normalized to GAPDH. (c) Quantitative RT-PCR for FABP4 mRNA expression in unsorted HeyA8 cells cocultured with adipocytes HPA 478 (1:5 in serum-free medium) and collected 24 h after washing and spinning to remove adipocytes. These data are normalized to GAPDH. (d) Quantitative RT-PCR for FABP4 mRNA expression in sorted ID8 cells cocultured with primary mouse adipocytes. Prior to sorting, ID8 cells were labeled in suspension with CMFDA (green). These data are normalized to GAPDH. Bars report means±s.e.m in (a)-(d).
Figure 17B:
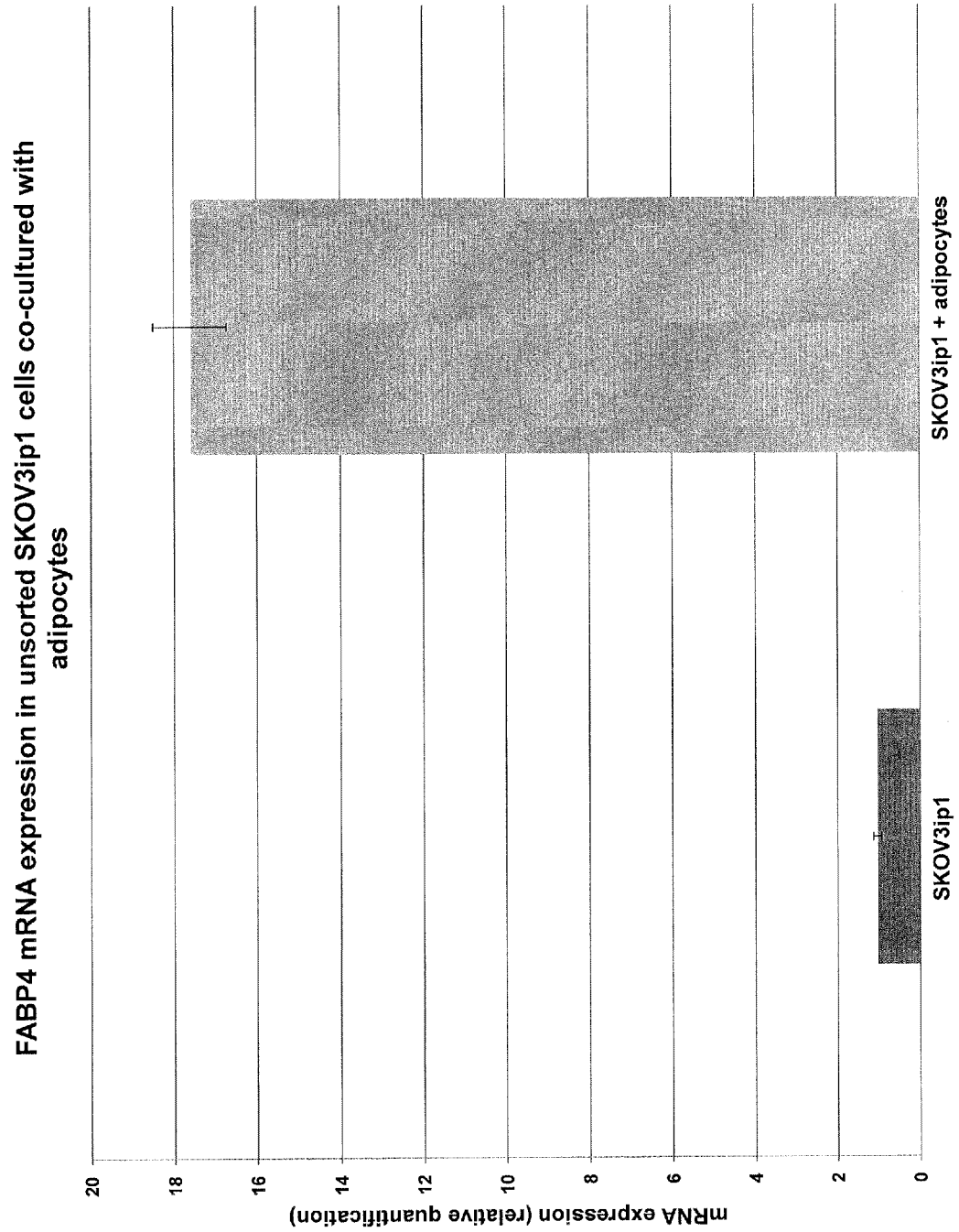
Figure 17C:
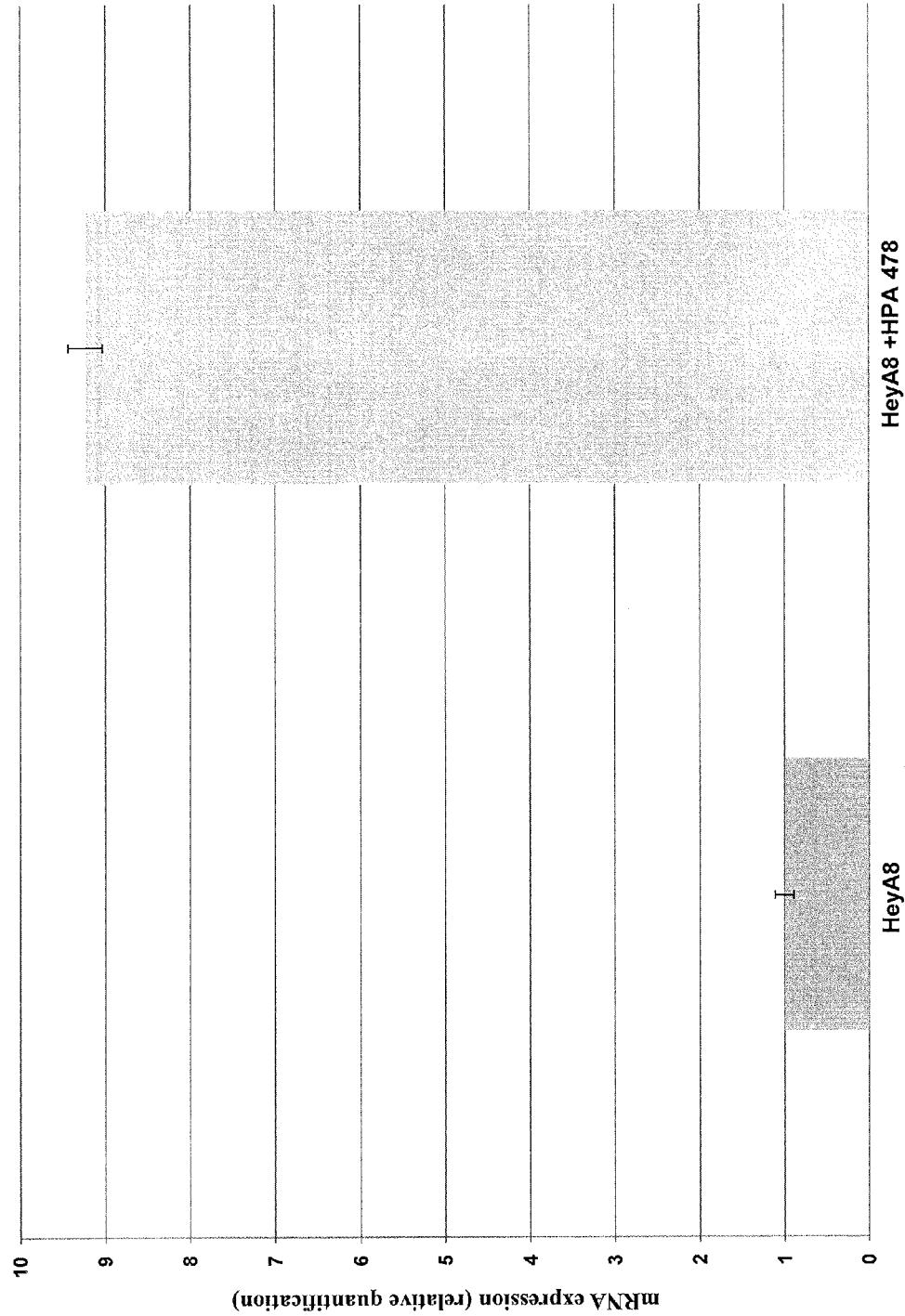
Figure 17D:
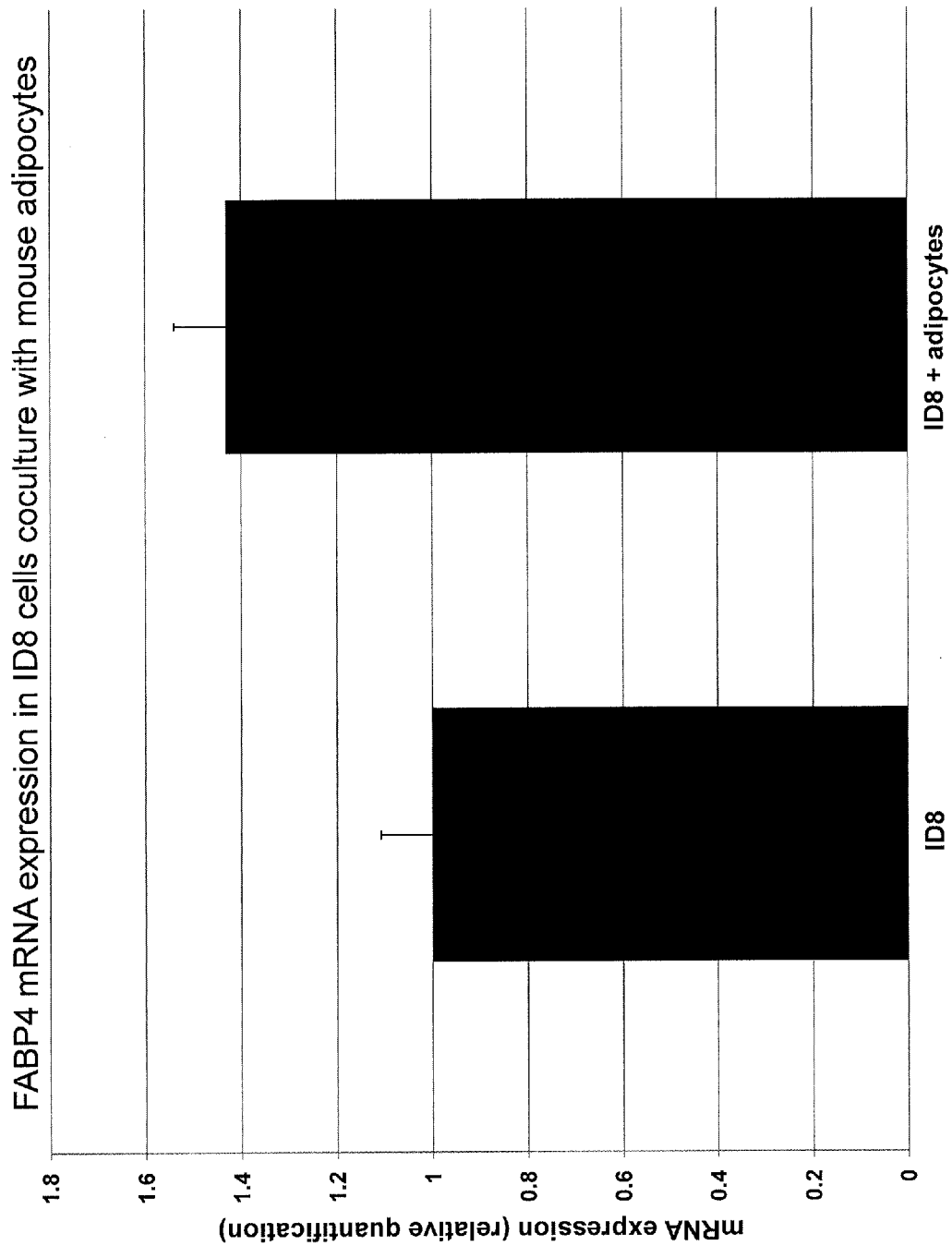

To further test the role of FABP4 in tumor growth and metastasis, the effects of FABP4 downregulation on tumor burden were investigated (FIGS. 16a-16d). The mRNA expression level of FABP4 ID8 was decreased in mouse ovarian cancer cells transfected with FABP4 shRNA (FIG. 16a). In the intraperitoneal model, the tumor burden in mice injected with shRNA-transfected ID8 mice was substantially lowered compared with the control group (FIGS. 16b-16c).

Figure 21:
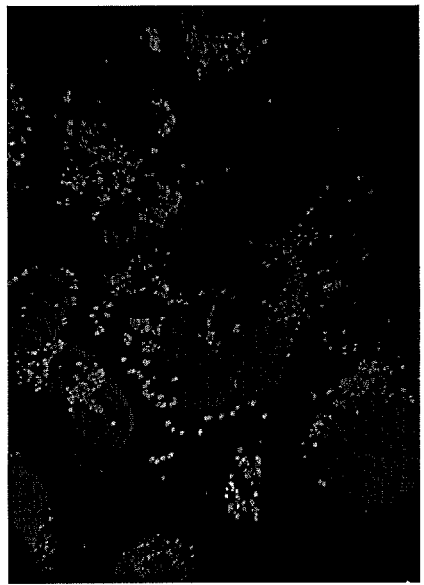
FIG. 21 Inhibition of FABP4 prevents lipid uptake in SKOV3ip1. SKOV3ip1 cells were cultured alone or with collagenase-digested adipocytes from human omentum and subcutaneous adipose tissue in the presence or absence of the FABP4 inhibitor HTS01037 (FABP4-I) for 36 h. The adipocytes were removed and the SKOV3ip1 cancer cells were incubated with Bodipy 493/503 which stains neutral lipids and counterstains the nuclei.
Figure 21:
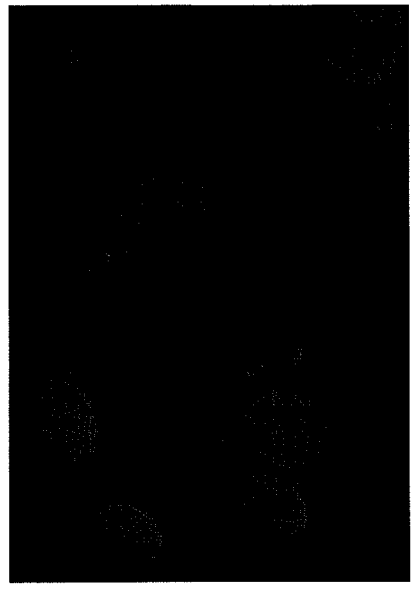
Figure 21:
Figure 21:
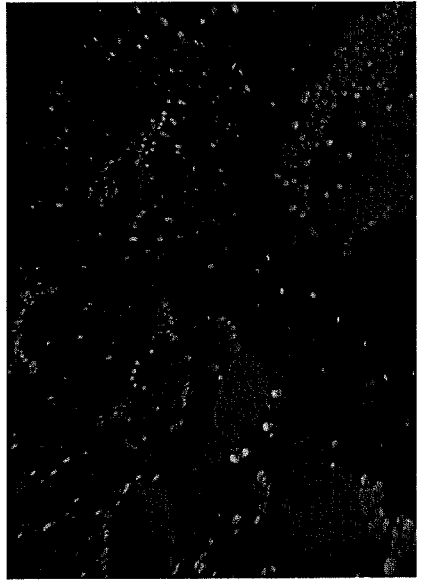
Figure 22:
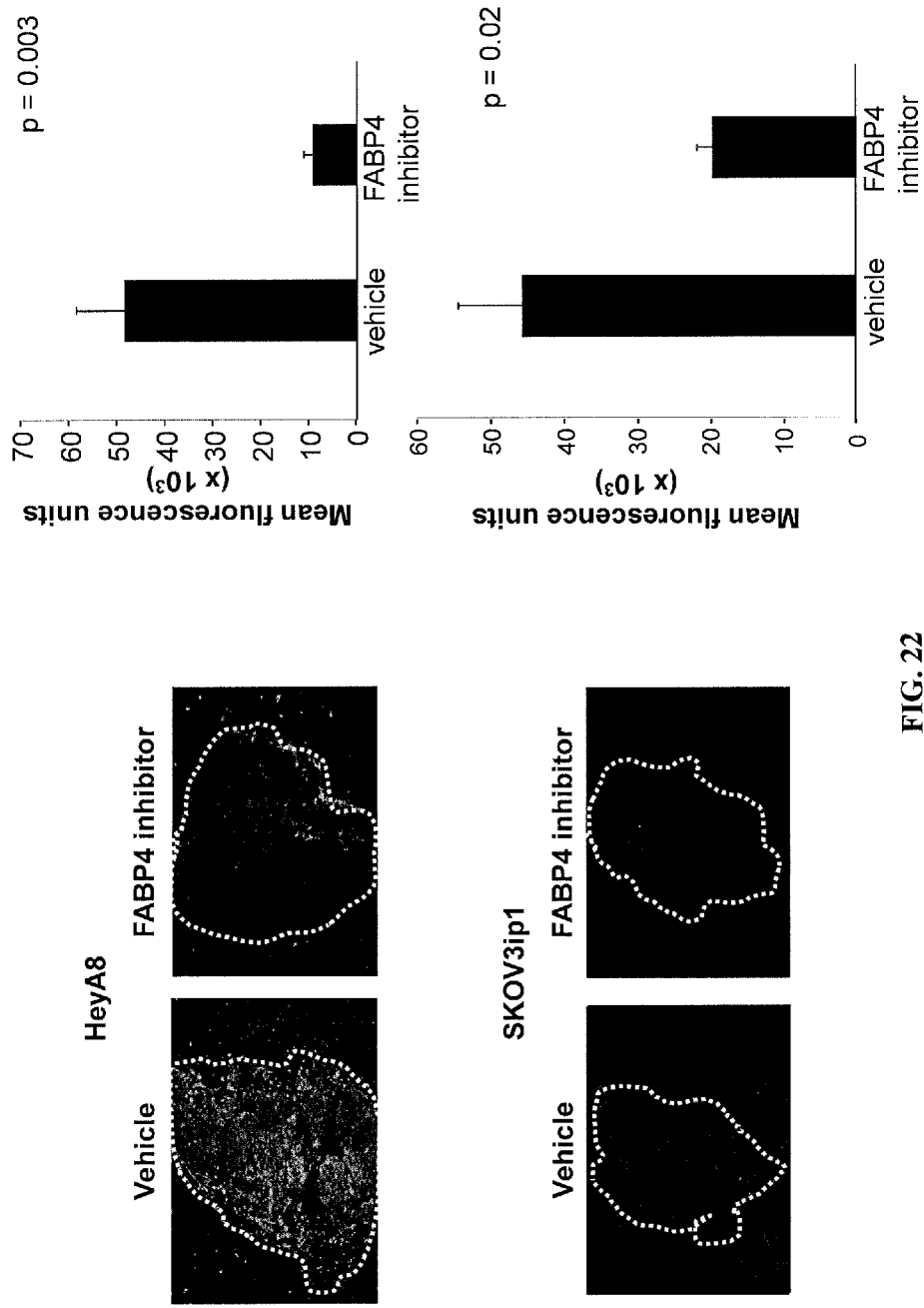
FIG. 22 FABP4 inhibition ex vivo reduces human ovarian cancer cell proliferation on section of human omentum. Small sections of human omentum were placed in low adhesive plates with the human ovarian cancer cells (HeyA8 or SKOV3ip1) that were fluorescently labeled in the presence or absence of FABP4 inhibitor (BMS309403) for 24 h. Representative images (left) and quantified fluorescence (right) were shown. Bars report means±s.e.m.
Figure 23A:
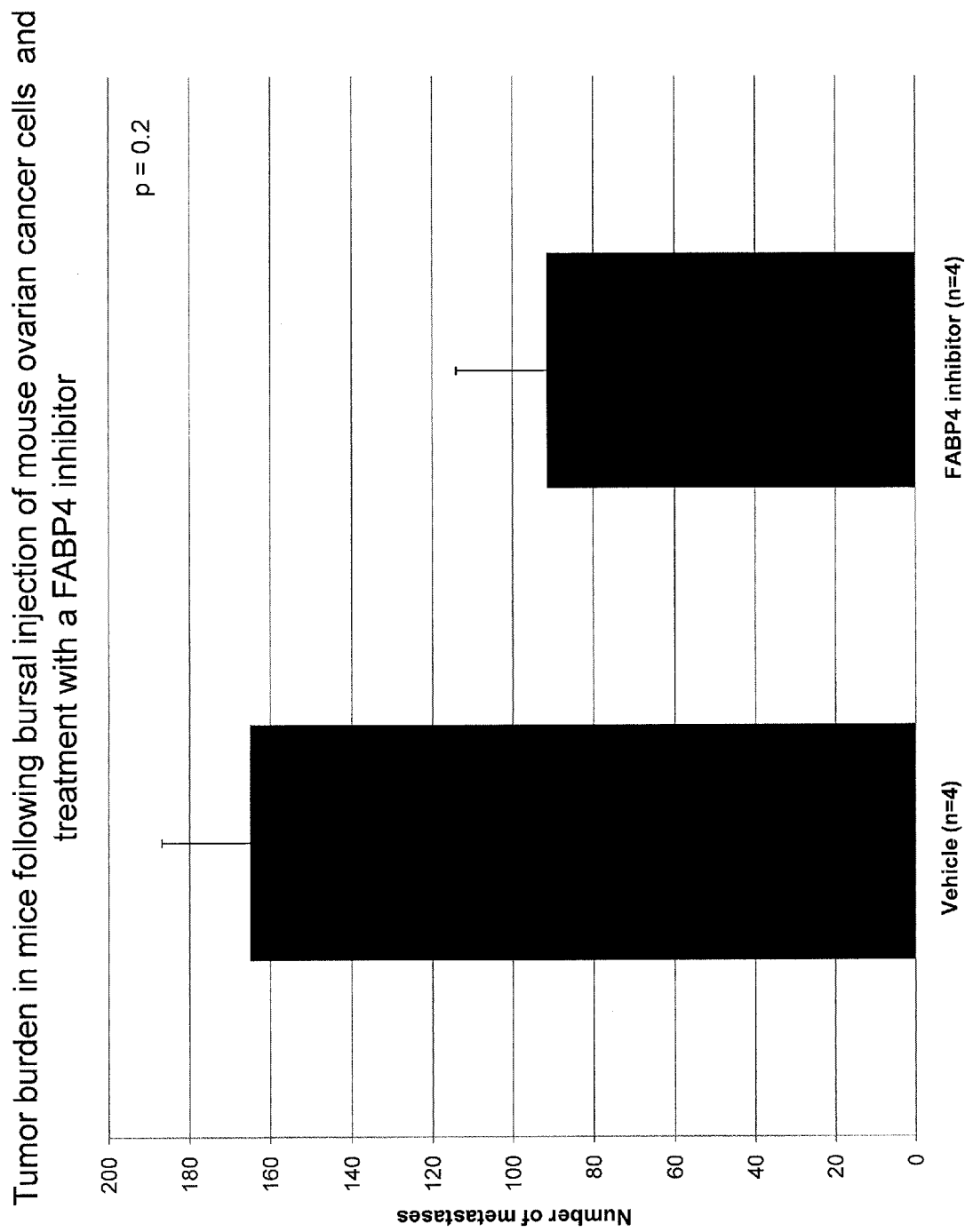
FIGS. 23a-23b Tumor burden in mice following bursal injection of mouse ovarian cancer cells and treatment with a FABP4 inhibitor. (a) Immune competent mice were injected with 1 million ID8 cells under the ovarian bursa. 60 days after ID8 cell injection, mice were treated with the FABP4 inhibitor (BMS309403) at 20 mg/kg body weight or control vehicle daily by oral gavage. Number of metastases (a) and metastatic tumor weight (b) were assessed 30 d after the FABP4 inhibitor or control vehicle treatment. Bars report means±s.e.m. in (a)-(b).
Figure 23B:
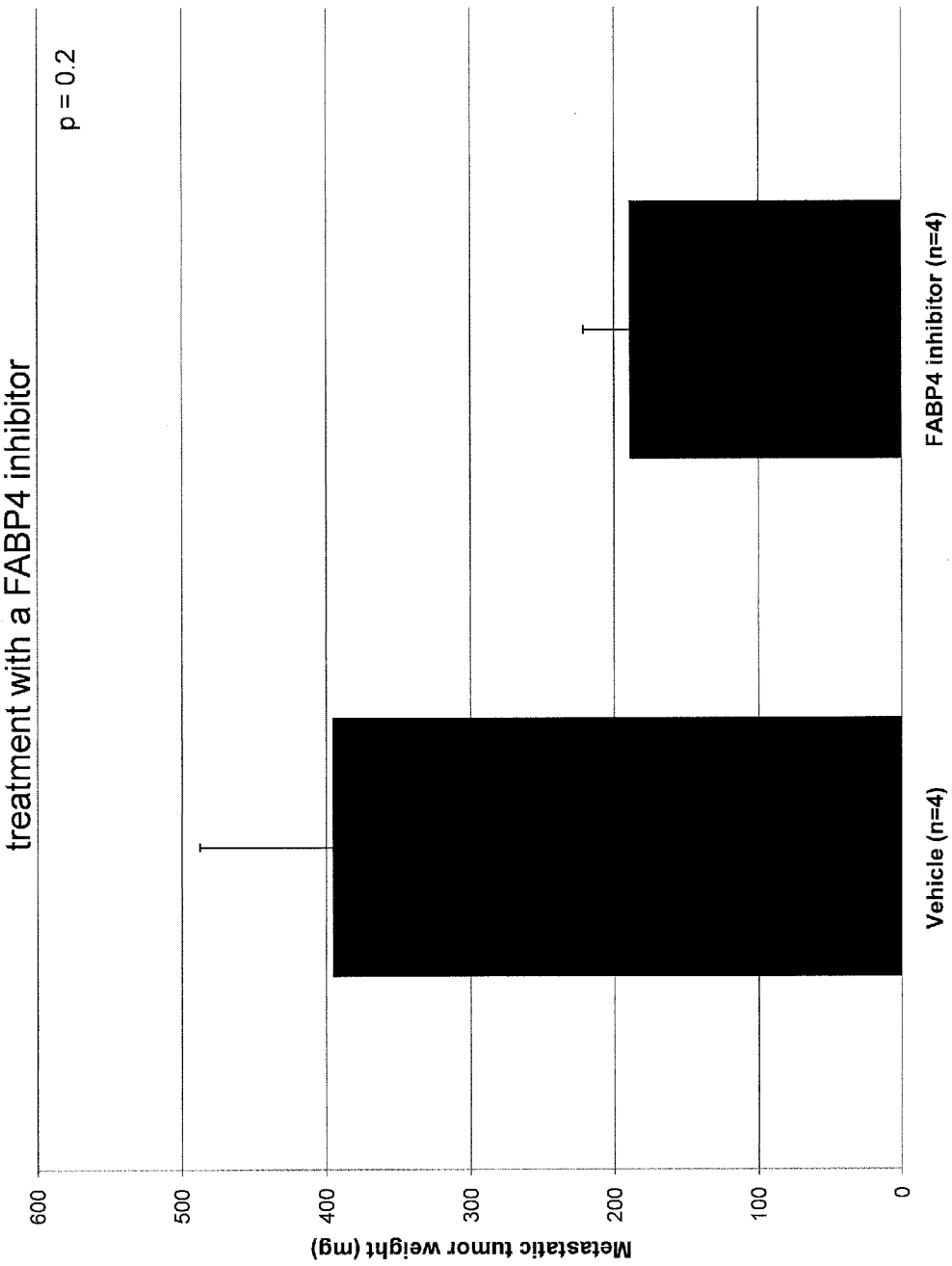

Taken together these data identify FABP4 as an excellent target to reduce metastasis of intra-abdominally disseminating tumors, like ovarian, gastric, and colon cancer, to adipose tissue. For instance, inhibiting FABP4 by the FABP4 inhibitor HTS01037 prevents lipid uptake in SKOV3ip1 cells cocultured with human omentum adipocytes (FIG. 21). BMS309403, another FABP4 inhibitor, also reduces human ovarian cancer cell proliferation on sections of human omentum (FIG. 22). Tumor burden in mice injected with ovarian cancers cells was also significantly reduced after the mice were treated with FABP4 inhibitor BMS309403 (FIGS. 23a-23b).

These findings identify adipocytes as major mediators in ovarian cancer metastasis to the omentum. Adipocytes promote the initial homing of tumor cells to the omentum through adipokine secretion. Subsequently, adipocytes provide fatty acids to the cancer cells, fueling rapid tumor growth. This mechanism may not be limited to ovarian cancer cells and provides a rationale for growth of other malignant cell types that metastasize both abdominally and in an adipocyte-rich environment (for example, in breast tissue). This concept is supported by several recent reports that suggest the tumor microenvironment promotes growth of breast cancer cells and together provide a rationale for the development of targeted therapies that hinder cancer metabolism fueled by the microenvironment (Martinez-Outschoorn, U. E. et al. 2010, Pavlides, S. et al. 2009). Current research on lipid metabolism in tumor cells primarily focuses on de novo fatty acid synthesis in oncogene-transformed tumor cells via glycolysis and glutaminolysis (Levine and Puzio-Kuter, 2010; DeBernardis et al., 2008). However, these data suggests that tumor lipid metabolism is regulated not only by genetic and epigenetic changes in the tumor cells but also by the availability of lipids in the microenvironment. Indeed, lipid metabolism and, more specifically, fatty acid metabolism contribute to tumorigenesis (Liu, Y. 2006, Zaugg, K. et al. 2011, Pike, L. S. et al. 2011, Hernlund, E. et al. 2008). Finally, FABP4, a mediator of lipid trafficking in adipocytes and potentially tumor cells, provides a therapeutic target to effectively impede intraabdominal metastasis and growth.

Adipocyte extraction Adipocytes were extracted from omental, subcutaneous, peritoneal, bowel mesenteric and normal adjacent omental (adjacent to omental tumor, denoted as cancer-associated) tissues. Tissue specimens were obtained from female subjects undergoing surgical procedures for benign conditions or tumor debulking for ovarian cancer treatment at the University of Chicago Medical Center. Informed consent was obtained from each subject before surgery, and the study was approved by the Institutional Review Board at the University of Chicago. Adipose tissue was transported in saline and minced in DMEM/F12 medium containing 0.2% (wt/vol) collagenase type 1 and 0.1% (wt/vol) bovine serum albumin (BSA). Minced adipose tissue was incubated at 37° C. on a rotary shaker at 80 r.p.m. for 1 h. Undigested tissue was removed after filtration through a 250-μm mesh filter, and mature adipocytes were collected by centrifugation at 200 g ((Rodbell, 1964). There was no contamination from other cell types (FIG. 2a). Adipocytes were used in experiments by their packed cell volume or counted using a hemocytometer and maintained in DMEM/F12 medium containing 0.1% BSA, denoted as SFM. This method was also used to isolate visceral adipocytes from mice.

In vivo and in vitro homing assays. For in vivo homing experiments, CMPTX-labeled SKOV3ip1 ovarian cancer cells (4×10$^6$) were pretreated (30 min) with inhibitory antibodies (R & D Systems, Minneapolis, Minn.) to CXCR1 (MAB330), IL-6R (MAB227) or mouse IgG control (MAB002). Mice were pretreated with 100 μg per kg body weight TIMP-1-specific (R& D Systems AF970) or goat IgG (R& D Systems AB108C) antibodies 30 min before cancer cell injection. Labeled SKOV3ip1 cells were injected intraperitoneally into female athymic nude mice. The omentum was removed 20 min later, digested in 1% (vol/vol) NP-40, and fluorescence was measured using a plate reader. In vitro homing was assessed by preparing a Matrigel plug in chamber slides. The plugs consisted of growth-factor-reduced Matrigel and human omental adipocytes in SFM containing an inhibitory antibody or a goat IgG control, in triplicate. Inhibitory antibodies (R&D Systems) to the following proteins were used at the following concentrations: IL-6 (AB206NA) and IL-8 (AB208NA), 50 ng ml$^{-1}$; MCP-1 (AB279NA), 100 μml$^{-1}$; MMP-9 (EMD Chemicals, Gibbstown, N.J., IM09L), 6 μg ml$^{-1}$; TIMP$^{-1}$, 100 ng ml$^{-1}$. CMFDA-labeled SKOV3ip1 cells (3×10$^6$) were added to a culture dish containing the plugs in 6 ml SFM. The plate was then incubated at 37° C. for 30 min. Plugs were removed, and fluorescence was measured using a plate reader. In vitro adhesion to equal portions (wt/wt) of full human omentum was carried out in low adhesion plates. Omentum was preincubated a TIMP-1 inhibitory antibody or a control goat IgG antibody (100 μg ml$^{-1}$). CMFDA-labeled SKOV3ip1 cells (4×10$^6$) were pretreated (30 min) with inhibitory antibodies to CXCR1, IL-6R or mouse IgG control. Cancer cells were added to the full omentum (separate wells for each treatment) and allowed to adhere for 20 min at 50 r.p.m. and 37° C. on a rotary shaker. Omentum was then digested in 1% NP-40, and fluorescence was measured using a plate reader.

Lipid visualization. Lipids were visualized in cancer cells cultured with adipocytes for 24-48 h, followed by removal of the adipocytes. SKOV3ip1 were then fixed in 10% formalin and stained with Bodipy 493/503 and Hoechst 33342 or fixed in 2% glutaraldehyde and 4% paraformaldehyde in 0.1 M sodium cacodylate for transmission electron microscopy (2600×). In lipid transfer experiments omental adipocytes were incubated with a fluorescent dodecanoic acid analog (Fatty acid uptake assay, Molecular Devices, Sunnyvale, Calif.), for 4 h. The adipocytes were washed in 1× Hank's balanced salt solution (HBSS) containing 0.2% fatty-acid free BSA to remove extracellular fatty acids. SKOV3ip1 cells were incubated with these labeled adipocytes, alone, or with the fatty acid analog for 24 h. Adipocytes and extracellular fatty acids were washed away with HBSS containing 0.2% fatty-acid free BSA and total fluorescence per well in triplicate was quantified. Images were acquired on a Zeiss LSM 510 laser scanning confocal microscope (630× oil) and processed using LSM image software. Quantification of Bodipy neutral lipid dye was performed using Imaris software (Bitplane Inc., South Windor, Conn.) and normalized to number of nuclei in field (5-10 fields/condition).

Fatty acid β-oxidation. β-oxidation of fatty acids was assessed using a previously described method (Moon, A et al. 1987), with minor modifications. Cancer cells were incubated with and without adipocytes (by packed cell volume, 1:3) for 24 h, in triplicate. Adipocytes were washed away, and the medium was changed to Krebs-Ringer's buffer containing 22 μm sodium palmitate, 7.48 μM fatty-acid-free BSA and 5 μCi [9,10(n)-$^3$H] palmitic acid per ml and incubated at 37° C. for 0-3 h. Etomoxir (10 μm, Sigma-Aldrich) and 1-carnitine (1 mM, Sigma-Aldrich) were added to wells as negative and positive controls, respectively. At the completion of each incubation period, the supernatant from each well was transferred to a microfuge tube containing 5% trichloroacetic acid to stop the reaction. Samples were centrifuged at 16,000 g, and the supernatant was transferred to a tube containing 1 N sodium hydroxide. Samples were then applied to a column (90 μM, Spectrum Labs) containing 0.5 g ml$^{-1}$ Dowex-1X8 ion-exchange resin and eluted with 1 ml deionized water. $^3$H$_2$O was quantified by scintillation counting. Radioactive $^3$H$_2$O secreted into the medium was normalized to the cellular protein content in each well.

Reverse Phase Protein Array (RPPA). Solid tumor nodules from the ovary and the omentum of 22 postmenopausal subjects, macroscopically and microscopically devoid of adipose tissue, were collected at cytoreductive surgery and snap frozen. Clinicopathologic information was collected prospectively (Kaur et al., 2009). Tissue sections were examined and verified histopathologically to be stage IIIC-IV serous-papillary adenocarcinomas by gynecologic pathologists. Triplicate sets of samples were dissected from the underlying stroma and used for analysis. Tissue samples were homogenized and spotted on nitrocellulose-coated FAST slides (Schleicher & Schuell BioScience) using an Aushon 2470 robotic printer (Aushon Biosystems). Validated primary antibodies were used to probe each slide. The slides were analyzed using Microvigene software (VigeneTech), as previously reported (Carey et al., 2010; Hennessy et al., 2010). The estimated protein concentrations were normalized by a median polish method and corrected for protein loading using the average expression levels.

Cell lines and reagents. SKOV3ip1, HeyA8 (from Dr. Gordon Mills, M.D. Anderson Cancer Center, Houston, Tex.), IOSE29 (from Dr. Nelly Auersperg, University of British Columbia, Vancouver, British Columbia, Canada) were grown as previously described (Kenny et al., 2007). T47D (from Dr. Charles Clevenger, Northwestern University, Chicago, Ill.), SNU-1, MDA-MB-231, and RKO (ATCC, Manassas, Va.) were cultured in Dulbecco's modified Eagle's medium (DMEM, T47D), RPMI 1640 (SNU-1 and MDA-MB-231) or Eagle's minimum essential medium (RKO) containing 10% fetal bovine serum (FBS), 100 U/ml penicillin, and 100 μg/ml streptomycin. The human ovarian cancer (OvCa) cell line, MONTY-1, was isolated from omental metastases, used at an early passage, and maintained in DMEM containing 10% FBS, 100 U/ml penicillin, and 100 μg/ml streptomycin. ID8 cells (Roby et al., 2000) (from Kathy Roby, University of Kansas Medical Center, Kansas City, Kans.) were maintained in DMEM containing 4% FBS, 5 mg/L insulin and transferrin, 5 μg/L sodium selenite, 100 U/ml penicillin, and 100 μg/ml streptomycin (Roby et al., 2000). Human peritoneal fibroblasts (HPF) were isolated as described (Kenny et al., 2007), immortalized using hTERT and maintained in DMEM containing 10% FBS and 200 μg/ml G418. The fatty acid binding protein (FABP4) inhibitor (Hertzel et al., 2009) was kindly provided by Dr. David Bernlohr (University of Minnesota, Minneapolis, Minn.) and used in experiments at 10 μM. CMTPX (C34552), CMFDA (C2925), Bodipy 493/503 (D3922), Hoechst 33342, Calcein AM (C1430), Alexa Fuor 488 goat anti-rabbit IgG, and collagenase type I were purchased from Invitrogen (Carlsbad, Calif.). Growth factor-reduced Matrigel and collagen type 1 were obtained from Becton Dickinson (Rockville, Md.). IL-6, IL-8, MCP-1, TIMP-1, CXCR1 and IL-6 receptor neutralizing antibodies and the goat and mouse IgG controls were obtained from R&D Systems (Minneapolis, Minn.). Acetyl CoA carboxylase and phosphorylated (p) acetyl CoA carboxylase (ser79) antibodies were purchased from Millipore (Billerica, Mass.). FABP 4 and CD31 antibodies from Abcam (Cambridge, Mass.) and Sigma-Aldrich (Atlas; St. Louis, Mo.) were utilized. Antibodies against hormone-sensitive lipase (HSL), p-HSL (ser660), AMP kinase (AMPK), p-AMPK (thr172, immunoblotting), p-Stat3 (ser727), p-p38 MAP kinase (MAPK) (thr180/tyr182), p38 MAPK, goat anti-rabbit IgG, GAPDH (14C10), and horse anti-mouse IgG were purchased from Cell Signaling (Danvers, Mass.). β-actin and β-tubulin antibodies, oil red o, etomoxir, L-carnitine, propranolol, and isoproterenol were purchased from Sigma-Aldrich (St. Louis, Mo.). The MMP-9 inhibitory antibody and 14-22 amide were purchased from EMD Chemicals (Gibbstown, N.J.). The Ki-67 antibody was obtained from Thermo Fisher Scientific (Neomarker; Waltham, Mass.). Antibodies against Stat3 and phospho-AMPK (thr172, immunofluorescence) were acquired from Santa Cruz (Santa Cruz, Calif.).

Animal experiments. All animal experiments were approved by the Institutional Animal Care and Use Committee, University of Chicago. Xenograft animal experiments and in vivo homing were conducted in female immune-compromised athymic nude mice. SKOV3ip1 cells alone (1×10$^6$), adipocytes alone (100 μl packed cell volume (PCV)), or SKOV3ip1 and adipocytes were injected subcutaneously with growth factor-reduced Matrigel (50 μl) into the flanks and shoulder of the mice. Tumor volumes were measured as described (Zou et al., 2007) over 24 d and tumor weight determined at the end of the experiment. Syngeneic animal experiments were conducted in immune-competent FABP4 deficient mice (FABP4$^{-/-}$) and wild-type (C57Bl6 background) littermates (Hotamisligil et al., 1996) by injecting ID8 mouse OvCa cells (5×10$^6$) intraperitoneally (Roby, K. F. et al. 2006, Robinson-Smith, T. M. et al. 2007) in the xenograft model or under the ovarian bursa (1×10$^6$) in the orthotopic model of OvC (Drew, A. et al. 2006, Greenaway, J. 2008). Tumors were allowed to grow for 10 weeks and 90 d respectively. Metastatic tumor weight and number of metastatic nodules were determined at the end of each experiment and tumor tissue fixed in 10% formalin.

Migration and Invasion assays. Transwell migration and invasion assays were conducted as described (Kenny et al., 2007; Kaur et al., 2009). Briefly, cells (80,000) were added to the upper chamber and allowed to migrate for 12 h or invade into collagen-coated (15 μg) membranes for 24 h at 37° C.

toward adipocytes (PCV) in DMEM/F12 containing 0.1% (BSA) denoted as serum-free medium (SFM, 1:3) in triplicate. Cells were fixed in 4% paraformaldehyde, stained with Giemsa, and cells in the upper chamber removed with cotton swabs to quantify the number of migrated and invaded cells in 5 fields per well in triplicate.

Cytokine arrays. Screening for 62 adipokines secreted from primary human omental adipocytes was performed by hybridizing 24 h conditioned medium with antibody-coated membranes (Human adipokine array, RayBiotech, Norcross, Ga.) according to the manufacturer's instructions. A biotin-conjugated antibody was used as a secondary antibody followed by detection with HRP-conjugated streptavidin.

Proliferation. In vitro proliferation was measured in cancer cells incubated with and without adipocytes over four days using a nucleic-acid binding fluorescent dye (Cyquant, Invitrogen, MA), as reported (Sawada et al., 2007).

Free fatty acid and glycerol detection. Primary human omental adipocytes were cultured with SKOV3ip1 cells in SFM (1:5, PCV adipocytes: SFM) and incubated at 37° C. for 24 h. Conditioned medium was collected and used in a colorimetric assay to detect free fatty acid and glycerol content, according to the manufacturer's specifications (Lipolysis assay, Zenbio, Research Triangle, NC). Isoproterenol treatment (1 µm) of adipocytes was used as a positive control.

Protein kinase A (PKA) activity. SKOV3ip1 were cocultured (1 h) with primary adipocytes or pretreated with isoproterenol (100 nM, positive control) or 14-22 amide (10 µM, negative control). Cells were lysed and protein kinase A (PKA) activity was assessed by phosphorylation of a substrate-coated plate followed by biotinylation and colorimetric detection according to the manufacturer's protocol (PKA activity assay kit, EMD Chemicals, Gibbstown, N.J.).

Quantitative real-time PCR. Primary human omental adipocytes were added to CMFDA-labeled SKOV3ip1 cells in SFM (1:5, PCV adipocytes:SFM) and incubated for 24 h. The adipocytes were removed and the cancer cells were subjected to FACS sorting to remove any remaining adipocytes. RNA was extracted from mouse and human adipocytes, human cancer cells and human IOSE cells using TRIzol (Invitrogen, Carlsbad, Calif.) and transcribed into cDNA using a high capacity cDNA kit (Applied Biosystems, Carlsbad, Calif.). Real-time quantitative reverse transcription-PCR (RT-PCR) was performed as described (Sawada et al., 2008) using the following probes (Applied Biosystems, Carlsbad, Calif.): acyl-coenzyme A oxidase (ACOX1, Hs01074241_m1), CXCR1 (IL-8 receptor, Hs00174146 ml), carnitine palmitoyltransferase 1a (CPT1a, Hs00912681_m1), fatty acid binding protein 4 (FABP4; human, Hs00609791_m1; mouse, Mm00445878_m1), perilipin 1 (PLIN1, Hs00160173_m1) and glyceraldehyde-3-phosphate dehydrogenase (GAPDH; human, Hs00266705_g1; mouse, Mm99999915_g1). Relative mRNA gene expression was calculated using the $2^{-\Delta\Delta Ct}$ method as described (Shell et al., 2007). RT-PCR was performed using the following primers at 1 µM; IL-6R (Tada, M. et al. 1994) (forward, CATTGCCATTGTTCTGAGGTTC; reverse, AGTAGTCTGTATTGCTGATGTC), gp130 (Path, G. et al. 2001) (forward, CATGCTTTGGGTGGAATGGAC; reverse, CATCAACAGGAAGTTGGTCCC), and GAPDH (Naif, H. M. et al. 1998) (forward, ATGGAGAAG-GCTGGGGCTC; reverse, AAGTTGTCATGGATGAC-CTTG). PCR cycles were carried out as reported.

Immunoblotting. In coculture experiments, primary human omental adipocytes were added to CMFDA-labeled SKOV3ip1 cells in SFM (1:5, PCV adipocytes:SFM) and incubated for 24 h. The adipocytes were removed and the SKOV3ip1 cells were subjected to FACS sorting to remove any remaining adipocytes in experiments involving FABP4 expression. Primary antibodies were used at the following dilutions: β-actin and total Stat3, 1:5000; FABP4, 1:4000; GAPDH, 1:2000; p-HSL, total HSL, p-ACC, total ACC, p-AMPK, total AMPK, p-Stat3, total p38 MAPK and β-tubulin, 1:1000; p-p38 MAPK, 1:500. Western Blots was performed as described (Kenny et al., 2008).

Immunohistochemistry. Primary human ovarian tumors and omental metastatic tissue (n=20), and mouse omentum (normal and tumor tissue) were fixed in 10% aqueous-buffered formalin, paraffin-embedded, sectioned (3-4 µm), mounted on slides, and stained as described (Zillhardt et al., 2010). Briefly, antigen retrieval was performed with a pressure cooker and 10 mM citrate buffer at pH 6 (FABP4 and CD31) or in 10 mM Tris base, 1 mM EDTA at a pH of 9 (Ki-67 and cleaved-caspase 3). Tissue sections were stained using the following primary antibody dilutions: FABP4 (human tissue) 1:25; FABP4 (mouse tissue) 1:100; CD31, 1:50; Ki-67, 1:300; cleaved-caspase 3, 1:25. Antibody binding was visualized with anti-rabbit polymer labeled HRP-bound secondary reagent (DAKO Envision+ System-HRP, Code K4002). Scoring of FABP4 protein expression in tissue sections was performed by two pathologists (KG, RBG) as follows: 0=negative; 1=weak; 2=strong. Microvessel density was measured by counting five random fields (400×, n=8-9). Ki-67 was counted in 250 tumor cells and scored as percent positive (n=8-9). Cleaved-caspase 3 positive cells were counted in five random fields (400×, n=5).

SKOV3ip1 cells were plated onto glass coverslips and cocultured with primary human omental adipocytes using a modified ceiling culture as described (Zhang, H. H. et al. 2000). Briefly, 50 µl adipocytes (PCV) were plated in 2 ml DMEM/F12 containing 20% FBS. Coverslips with and without SKOV3ip1 cells were set on the surface in contact with adipocytes for 3 d to allow the adipocytes to attach. Coverslips were dried for 1 h and fixed in ice-cold acetone prior to incubation with p-AMPK (1:100) and p-HSL (1:400) antibodies. The secondary antibody, Alexa Fluor 488 goat anti-rabbit IgG, was used at 1:300. Coverslips were counterstained with Hoescht 33342 (1:2000). Images were acquired on a Zeiss LSM 510 laser scanning confocal microscope (630× oil).

Statistical Analysis. The mean and the standard error of the mean (s.e.m) are reported. Data was compared using two-tailed and paired Student's t-tests. Differences were considered significant if P<0.05.

References

The following references, to the extent that they provide exemplary procedural or other details supplementary to those set forth herein, are specifically incorporated herein by reference.

Landen, C., Birrer, M. J., & Sood, A. K. Early events in the pathogenesis of epithelial ovarian cancer. J Clin Oncol 26, 995-1005 (2008).

Cho, K. R. & Shih, I.-M. Ovarian cancer. Annu Rev Pathol 4, 287-313 (2009).

Lengyel, E. Ovarian cancer development and metastasis. Am J Pathol 177, 1053-1064 (2010).

Rodbell, M. Metabolism of isolated fat cells. The Journal of Biological Chemistry 239, 375-380 (1964).

Kenny, H. A., Kaur, S., Coussens, L., & Lengyel, E. The initial steps of ovarian cancer cell metastasis are mediated by MMP-2 cleavage of vitronectin and fibronectin. J Clin Invest 118, 1367-1379 (2008).

Merritt, W. et al. Effect of interleukin-8 gene silencing with liposome-encapsulated small interfering RNA on ovarian cancer cell growth. J. Natl. Cancer Inst. 100, 359-372 (2008).

Manabe, Y., Toda, S., Miyazaki, K., & Sugihara, H. Mature adipocytes, but not preadipocytes, promote the growth of breast carcinoma cells in collagen gel matrix culture through cancer-stromal cell interactions. J Pathology 201, 221-228 (2003).

Tokuda, Y. et al. Prostate cancer cell growth is modulated by adipocyte-cancer cell interaction. BJU International 91, 716-720 (2003).

Hardy, S., St-Onge, G. G., Joly, E., Langelier, Y., & Prentki, M. Oleate promotes the proliferation of breast cancer cells via the G protein-coupled receptor GPR40. J Biol Chem 280, 13285-13291 (2005).

Gazi, E. et al. Direct evidence of lipid translocation between adipocytes and prostate cancer cells with imaging FTIR microspectroscopy. Journal of Lipid Research (2007).

Kaur, S. et al. b3-integrin expression on tumor cells inhibits tumor progression, reduces metastasis, and is associated with a favorable prognosis in patients with ovarian cancer. Am J Pathol 175, 2184-2196 (2009).

Elliott, B. E., Tam, S. P., Dexter, D., & Chen, Z. Q. Capacity of adipose tissue to promote growth and metastasis of a murine mammary carcinoma: Effect of estrogen and progesterone. Int J Cancer 51, 416-424 (1992).

Wakil, S. J. & Abu-Elheiga, L. A. Fatty acid metabolism: Target for metabolic syndrome. Journal of Lipid Research 50, S138-S143 (2009).

Sengenès, C. et al. Involvement of a cGMP pathway in the natriuretic peptide-mediated hormone sensitive lipase phosphorylation in human adipocytes. J Biol Chem 278, 48617-48626 (2003).

Brasaemle, D. L., Subramanian, V., Garcia, A., Marcinkiewicz, A., & Rothenberg, A. Perilipin A and the control of triacylglycerol metabolism. Mol Cell Biochem 326, 15-21 (2009).

Gagnon, A. M. et al. Thyroid-stimulating hormones stimulates lipolysis in adipocytes in culture and raises serum free fatty acid levels in vivo. Metabolism clinical and experimental 59, 547-553 (2010).

Wang, W. & Guan, K.-L. AMP-activated protein kinase and cancer. Acta Physiol 55-63 (2010).

Carey, M. S. et al. Functional proteomic analysis of advanced serous ovarian cancer using reverse phase protein array: TGF-b pathway signaling indicates response to primary chemotherapy. Clin Cancer Res 16, 2852-2860 (2010).

Munday, M. R., Campbell, D. G., Carling, D., & Hardie, D. G. Identification by amino acid sequencing of three major regulatory phosphorylation sites on rat acetyl-CoA carboxylase. Eur J Biochem 175, 331-338 (1988).

Hotamisligil, G. S. et al. Uncoupling of obesity from insulin resistance through a targeted mutation in aP2, the adipocyte fatty acid binding protein. Science 274, 1377-1379 (1996).

Furuhashi, M. & Hotamisligil, G. S. Fatty acid binding proteins: Role in metabolic diseases and potential as drug targets. Nature Reviews Drug Discovery 7, 489-503 (2008).

Hertzel, A. V. et al. Identification and characterization of a small molecule inhibitor of fatty acid binding proteins. J Med Chem 52, 6024-6031 (2009).

Uysal, K. T., Scheja, L., Wiesbrock, S. M., Bonner-Wier, S., & Hotamisligil, G. S. Improved glucose and lipid metabolism in genetically obese mice lacking aP2. Endocrinology 141, 3388-3396 (2000).

Levine, A. J. & Puzio-Kuter, A. M. The control of the metabolic switch in cancers by oncogenes and tumor suppressor genes. Science 330, 1340-1344 (2010).

DeBernardis, R. J., Lum, J. J., Hatzivassiliou, G., & Thompson, C. B. The biology of cancer: Metabolic programming fuels cell growth and proliferation. Cell Metabolism 7, 11-20 (2008).

Moon, A. & Rhead, W. J. Complementation analysis of fatty acid oxidation disorders. J Clin Invest 79, 59-64 (1987).

Hennessy, B. T. et al. A technical assessment of the utility of reverse phase protein arrays for the study of the functional proteome in non-microdissected human breast cancers. Clinical Proteomics 6, 129-151 (2010).

Kenny, H. A., Krausz, T., Yamada, S. D., & Lengyel, E. Use of a novel 3D culture model to elucidate the role of mesothelial cells, fibroblasts and extra-cellular matrices on adhesion and invasion of ovarian cancer cells. Int J Cancer 121, 1463-1472 (2007).

Roby, K. F. et al. Development of a syngeneic mouse model for events related to ovarian cancer. Carcinogenesis 21, 585-591 (2000).

Zou, H. et al. An orally available small-molecule inhibitor of c-Met PF-2341066, exhibits cytoreductive antitumor efficacy through antiporliferative and antiangiogenic mechanisms. Cancer Res 67, 4408-4417 (2007).

Hotamisligil, G. S. et al. Uncoupling of obesity from insulin resistance through a targeted mutation in aP2, the adipocyte fatty acid binding protein. Science 274, 1377-1379 (1996).

Kaur, S. et al. b3-integrin expression on tumor cells inhibits tumor progression, reduces metastasis, and is associated with a favorable prognosis in patients with ovarian cancer. Am J Pathol 175, 2184-2196 (2009).

Sawada, K. et al. C-Met overexpression is a prognostic factor in ovarian cancer and an effective target for inhibition of peritoneal dissemination and invasion. Cancer Res 67, 1670-1680 (2007).

Sawada, K. et al. Loss of E-cadherin promotes ovarian cancer metastasis via alpha 5-integrin, which is a therapeutic target. Cancer Res 68, 2329-2339 (2008).

Shell, S. et al. Let-7 expression defines two differentiation stages of cancer. Proc Natl Acad Sci USA 104, 11400-11405 (2007).

Kenny, H. A., Kaur, S., Coussens, L., & Lengyel, E. The initial steps of ovarian cancer cell metastasis are mediated by MMP-2 cleavage of vitronectin and fibronectin. J Clin Invest 118, 1367-1379 (2008).

Zillhardt, M., Christensen, J., & Lengyel, E. An orally available small molecule inhibitor of c-Met, PF-2341066, reduces tumor burden in a pre-clinical model of ovarian cancer metastasis. Neoplasia 12, 1-10 (2010).

Fire et al., Potent and specific genetic interference by double-stranded RNA in *Caenorhabditis elegans*. Nature, 391 (6669): 806-811 (1998).

Nilsson, M. B., Langley, R. R. & Fidler, I. J. Interleukin-6 secreted by human ovarian carcinoma cells is a potent proangiogenic cytokine. *Cancer Res.* 65, 10794-10800 (2005).

Dirat, B. et al. Cancer-associated adipocytes exhibit an activated phenotype and contribute to breast cancer invasion. *Cancer Res.* 71, 2455-2465 (2011).

Gonzalez-Yanes, C. & Sanchez-Margalet, V. Signalling mechanisms regulating lipolysis. *Cellular Signaling* 18, 401-408 (2006).

Sengenès, C. et al. Involvement of a cGMP pathway in the natriuretic peptide-mediated hormone sensitive lipase phosphorylation in human adipocytes. *J. Biol. Chem.* 278, 48617-48626 (2003).

Scheja, L. et al. Altered insulin secretion associated with reduced lipolytic efficiency in aP2$^{-/-}$ mice. *Diabetes* 48, 1987-1994 (1999)

Furuhashi, M. et al. Treatment of diabetes and atherosclerosis by inhibiting fatty-acid-binding protein aP2. *Nature* 447, 959-965 (2007).

Martinez-Outschoorn, U. E. et al. The autophagic tumor stroma model of cancer or "battery-operated tumor growth" a simple solution to the autophagy paradox. *Cell Cycle* 9, 4297-4306 (2010).

Pavlides, S. et al. The reverse Warburg effect: aerobic glycolysis in cancer associated fibroblasts and the tumor stroma. *Cell Cycle* 8, 3984-4001 (2009).

Liu, Y. Fatty acid oxidation is a dominant bioenergetic pathway in prostate cancer. *Prostate Cancer Prostatic Dis.* 9, 230-234 (2006).

Zaugg, K. et al. Carnitine palmitoyltransferase 1C promotes cell survival and tumor growth under conditions of metabolic stress. *Genes Dev.* 25, 1041-1051 (2011).

Hemlund, E. et al. Potentiation of chemotherapeutic drugs by energy metabolism inhibitors 2-deoxyglucose and etomoxir. *Int. J. Cancer* 123, 476-483 (2008).

Pike, L. S., Smift, A. L., Croteau, N. J., Ferrick, D. A. & Wu, M. Inhibition of fatty acid oxidation by etomoxir impairs NADPH production and increases reactive oxygen species resulting in ATP depletion and cell death in human glioblastoma cells. *Biochim. Biophys. Acta* 1807, 726-734 (2011).

Hennessy, B. T. et al. A technical assessment of the utility of reverse phase protein arrays for the study of the functional proteome in non-microdissected human breast cancers. *Clin. Proteomics* 6, 129-151 (2010).

---

What is claimed is:

1. A method of inhibiting ovarian cancer comprising administering to a subject having or suspected of having cancer an effective amount of a fatty acid binding protein (FABP) inhibitor, wherein the FABP inhibitor is a carbazole butanoic acid, aryl sulfonamide, sulfonylthiophene, 4-hydroxypyrimidine, 2,3-dimethylindole, benzoylbenzene, biphenyl-alkanoic acid, 2-oxazole-alkanoic acid, tetrahydropyrimidone, pyridone, pyrazinone, aryl carboxylic acid, tetrazole, triazolopyrimidinone, indole, or BMS480404.

2. The method of claim 1, wherein the FABP inhibitor is a FABP 4 inhibitor.

3. The method of claim 2, wherein the FABP4 inhibitor is BMS309403; pyrazole, 4-{[2-(methoxycarbonyl)-5-(2-thienyl)-3-thienyl]amino}-4-oxo-2-butenoic acid; or ((2'-(5-ethyl-3,4-diphenyl-1H-pyrazol-1-yl)(1,1'-biphenyl)-3-yl)oxy)-acetic acid.

4. The method of claim 1, wherein the FABP inhibitor is a FABP5 inhibitor.

5. The method of claim 1, wherein the FABP inhibitor inhibits the activity of more than one FABP.

6. The method of claim 1, wherein the FABP inhibitor is administered intravascularly, intraperitoneally, or orally.

7. The method of claim 1, further comprising administering a second anti-cancer therapy.

8. A method of delaying the occurrence of cancer comprising administering to a subject an effective amount of a fatty acid binding protein (FABP) inhibitor, wherein the FABP inhibitor is a carbazole butanoic acid, aryl sulfonamide, sulfonylthiophene, 4-hydroxypyrimidine, 2,3-dimethylindole, benzoylbenzene, biphenyl-alkanoic acid, 2-oxazole-alkanoic acid, tetrahydropyrimidone, pyridone, pyrazinone, aryl carboxylic acid, tetrazole, triazolopyrimidinone, indole or BMS480404, wherein the subject may develop or is at increased risk of developing ovarian cancer.

9. A method of inhibiting ovarian cancer metastasis comprising administering to a patient having or at risk of developing ovarian cancer an effective amount of a fatty acid binding protein 4 (FABP4) inhibitor, wherein the FABP4 inhibitor is a carbazole butanoic acid, aryl sulfonamide, sulfonylthiophene, 4-hydroxypyrimidine, 2,3-dimethylindole, benzoylbenzene, biphenyl- alkanoic acid, 2-oxazole-alkanoic acid, tetrahydropyrimidone, pyridone, pyrazinone, aryl carboxylic acid, tetrazole, triazolopyrimidinone, or indole.

10. A method of inhibiting ovarian cancer cell growth comprising administering to a ovarian cancer patient an effective amount of a fatty acid binding protein (FABP) inhibitor, wherein the FABP inhibitor is a carbazole butanoic acid, aryl sulfonamide, sulfonylthiophene, 4-hydroxypyrimidine, 2,3-dimethylindole, benzoylbenzene, biphenyl-alkanoic acid, 2-oxazole-alkanoic acid, tetrahydropyrimidone, pyridone, pyrazinone, aryl carboxylic acid, tetrazole, triazolopyrimidinone, indole or BMS480404.

11. The method of claim 10, wherein the FABP inhibitor is a FABP4 inhibitor.

12. The method of claim 10, wherein the FABP inhibitor is a FABP5 inhibitor.

13. The method of claim 10, wherein the FABP inhibitor inhibits the activity of more than one FABP.

* * * * *

UNITED STATES PATENT AND TRADEMARK OFFICE
CERTIFICATE OF CORRECTION

PATENT NO. : 8,748,470 B2
APPLICATION NO. : 13/422712
DATED : June 10, 2014
INVENTOR(S) : Lengyel et al.

It is certified that error appears in the above-identified patent and that said Letters Patent is hereby corrected as shown below:

In the Specification

On Column 1, Line 8, the paragraph should read as follows:
-- This invention was made with government support under grant number CA111882 awarded by the National Institutes of Health. The government has certain rights in the invention. --

Signed and Sealed this
Thirtieth Day of August, 2022

Katherine Kelly Vidal
*Director of the United States Patent and Trademark Office*

SEQUENCE LISTING

<160> NUMBER OF SEQ ID NOS: 2

<210> SEQ ID NO 1
<211> LENGTH: 58
<212> TYPE: DNA
<213> ORGANISM: Artificial Sequence
<220> FEATURE:
<223> OTHER INFORMATION: Synthetic primer

<400> SEQUENCE: 1

```
ccggctggat ggaaatttgc atcaactcga gttgatgcaa atttccatcc agttttg      58
```

<210> SEQ ID NO 2
<211> LENGTH: 838
<212> TYPE: DNA
<213> ORGANISM: Homo sapiens

<400> SEQUENCE: 2

```
gggtcacagc accctcctga aaactgcagc ttccttctca ccttgaagaa taatcctaga     60
aaactcacaa aatgtgtgat gcttttgtag gtacctggaa acttgtctcc agtgaaaact    120
ttgatgatta tatgaaagaa gtaggagtgg gctttgccac caggaaagtg gctggcatgg    180
ccaaacctaa catgatcatc agtgtgaatg gggatgtgat caccattaaa tctgaaagta    240
cctttaaaaa tactgagatt tccttcatac tgggccagga atttgacgaa gtcactgcag    300
atgacaggaa agtcaagagc accataacct tagatggggg tgtcctggta catgtgcaga    360
aatgggatgg aaaatcaacc accataaaga gaaacgaga ggatgataaa ctggtggtgg     420
aatgcgtcat gaaaggcgtc acttccacga gagtttatga gagagcataa gccaagggac    480
gttgacctgg actgaagttc gcattgaact ctacaacatt ctgtgggata tattgttcaa    540
aaagatattg ttgttttcca tgatttagca agcaactaat tttctcccaa gctgatttta    600
ttcaatatgg ttacgttggt taaataaact ttttttagat ttagaaggtg atgtaatgat    660
gtattcattg tgcttatgat gtattcttag tcataactga gtgaaggaaa tgggaaattt    720
gcattatttc tttgttctga tatgaataat aacatatttc ataataattc aaggtaaaaa    780
gggatatcta tggatttccc taggtaggag ataacaagta tgtaccatta ctgaatat       838
```